(12) United States Patent
Tahar et al.

(10) Patent No.: US 10,946,219 B2
(45) Date of Patent: Mar. 16, 2021

(54) FIXED FIELD ALTERNATING GRADIENT ION ACCELERATOR FOR VARIABLE ENERGY EXTRACTION

(71) Applicant: The Trustees of Columbia University in the City of New York, New York, NY (US)

(72) Inventors: Malek Haj Tahar, New York, NY (US); Gerhard Randers-Pehrson, Ossining, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 204 days.

(21) Appl. No.: 16/122,190

(22) Filed: Sep. 5, 2018

(65) Prior Publication Data

US 2019/0070438 A1    Mar. 7, 2019

Related U.S. Application Data

(60) Provisional application No. 62/554,275, filed on Sep. 5, 2017.

(51) Int. Cl.
*H05H 7/04* (2006.01)
*A61N 5/10* (2006.01)
(Continued)

(52) U.S. Cl.
CPC .............. *A61N 5/1077* (2013.01); *H05H 7/04* (2013.01); *H05H 7/12* (2013.01); *H05H 9/00* (2013.01);
(Continued)

(58) Field of Classification Search
CPC ......... A61N 5/1077; A61N 2005/1087; H05H 13/085; H05H 9/00; H05H 7/04; H05H 7/12; H05H 7/08; H05H 7/10
See application file for complete search history.

(56) References Cited

U.S. PATENT DOCUMENTS 8,173,983 B1 *   5/2012   Sahadevan ........... A61N 5/1084
                                                       250/494.1
9,583,302 B2 *   2/2017   Figueroa Saavedra .....................
                                                       A61N 5/1042
(Continued)

OTHER PUBLICATIONS

Berg, J.S., et al., "Cost-effective design for a neutrino factory", "Phys. Rev. ST Accel. Beams", Jan. 24, 2006, vol. 9, No. 011001, Publisher: The American Physical Society, Published in: DOI: 10.1103/PhysRevSTAB.9.011001.
(Continued)

*Primary Examiner* — Amy Cohen Johnson
*Assistant Examiner* — Jianzi Chen
(74) *Attorney, Agent, or Firm* — Wolter Van Dyke Davis, PLLC; Eugene J. Molinelli

(57) ABSTRACT

A method and apparatus for use as a compact medical ion accelerator includes a charged particle linear accelerator module and a pair of fixed field magnet assemblies. The linear accelerator module accelerates a pulse of charged particles as a beam aligned along a first ray. The pair of assemblies controls the orbits of the pulse by turning the pulse 360 degrees within a first plane. The magnet assemblies are disposed on opposite sides of the linear accelerator with mirrored symmetry relative to a line that is perpendicular to the first ray and passes through a reference point in the first plane. Each assembly includes a pair of magnets for which a strength of a magnetic field varies non-linearly along a radial direction; and a superconducting magnet for which a strength of a magnetic field varies along a radial direction. The superconducting magnet is disposed between the pair of magnets.

11 Claims, 40 Drawing Sheets

(51) Int. Cl.
H05H 7/12 (2006.01)
H05H 13/08 (2006.01)
H05H 9/00 (2006.01)
H05H 7/08 (2006.01)
H05H 7/10 (2006.01)

(52) U.S. Cl.
CPC ... *H05H 13/085* (2013.01); *A61N 2005/1087* (2013.01); *A61N 2005/1095* (2013.01); *H05H 7/08* (2013.01); *H05H 7/10* (2013.01); *H05H 2007/125* (2013.01)

(56) References Cited

U.S. PATENT DOCUMENTS

| | | | | |
|---|---|---|---|---|
| 2005/0200322 | A1* | 9/2005 | Kulish | H05H 9/00 315/505 |
| 2011/0260729 | A1* | 10/2011 | Carlone | A61N 5/1049 324/318 |
| 2012/0313003 | A1* | 12/2012 | Trbojevic | G21K 5/04 250/396 ML |
| 2014/0243576 | A1* | 8/2014 | Kakutani | H05H 13/04 600/1 |
| 2016/0361566 | A1* | 12/2016 | Larkin | A61N 5/1045 |

OTHER PUBLICATIONS

Bogoliubov, N.N. et al., "Asymptotic methods in the theory of nonlinear oscillations", 1961, pp. 386-395, Publisher: Gordon and Breach, Published in: New York, NY, US.

Garland, J. M., et al., "Normal-conducting scaling fixed field alternating gradient accelerator for proton therapy", "Physical Review Accelerators and Beams", Sep. 29, 2015, vol. 18, No. 094701, Publisher: Published by The American Physical Society, Published in: DOI: 10.1103/PhysRevSTAB.18.094701.

Ishi, Y., et al., "Status of KURRI Facility presented at the FFAG 2016 workshop, Imperial college, London, UK", Sep. 6, 2016, pp. 1-63, Published in: https://indico.cern.ch/event1543264/contributions/2295846/attachments/1333675/2005286/FFAG16_LONDON_ishi.pdf.

Kolomensky, A. A., et al., "Theory of Cyclic Accelerators", 1966, pp. 77-81, Publisher: North-Holland publishing company, Published in: Holland.

Machida, Shinji, et al., "Commissioning of 150MeV FFAG Synchrotron", 2004, p. 2643 Publisher: Proceedings of EPAC 2004, Published in: Lucerne, Switzerland.

Machida, Shinji, "Scaling Fixed-Field Alternating Gradient Accelerators with a Small Orbit Excursion", Oct. 14, 2009, No. 103, 164801 (2009), Publisher: Physical Review Letters, Published in: DOI: 10.1103/PhysRevLett.103.164801.

Meot F, "Zgoubi Users Guide", "Report C-A/AP/#470", Oct. 25, 2012, Publisher: BNL-98726-2012-IR, Published in: https://www.bnl.gov/isd/documents/79375.pdf.

Machida, Shinji, "Scaling Fixed-Field Alternating-Gradient Accelerators with Reverse Bend and Spiral Edge Angle", Aug. 10, 2017, No. 119, 064802, Publisher: Physical Review Letters, Published in: DOI: 10.1103/PhysRevLett.119.064802.

Misu, T., et al., "Design study of compact medical fixed-field alternating-gradient accelerators", "Accelerators and Beams", Sep. 21, 2004, vol. 7, No. 094701, Publisher: Physical Review Special Topics, Published in: DOI: 10.1103/PhysRevSTAB.7.094701.

Pyeon, Cheol, et al., "First Injection of Spallation Neutrons Generated by High-Energy Protons into the Kyoto University Critical Assembly", Aug. 21, 2009, pp. 1091-1093, vol. 46, No. 12, Publisher: Journal of Nuclear Science and Technology, Published in: https://doi.org/10.1080/18811248.2009.9711620.

Schippers, J. M., "Beam-Transport Systems for Particle Therapy", 2017, pp. 241-252, vol. 1, Publisher: CERN Yellow Reports: School Proceedings, Published in: doi:http://dx.doi_org/1023730/CYRSP-2017-001.241.

Sheehy, S. L., et al., "Characterisation of the Kurri 150 MeV FFAG and Plans for High Intensity Experiments", Nov. 2014, pp. 89-93, No. paper MOPAB27, Publisher: presented at the 57th ICFA Advanced Beam Dynamics Workshop on High Intensity, High Brightness and High Power Hadron Beams, Published in: East Lansing, MI, USA.

Sheehy, S. L., et al., "Progress on simulation of fixed field alternating gradient accelerators, 6th International Particle Accelerator Conference", 2015, Publisher: MOPJE077, IPAC'15, Virginia, USA, Published in: http://accelconf.web.cern.ch/AccelConf/IPAC2015/papers/mopje077.pdf.

Sheehy, S. L., et al., "Characterization techniques for fixed field alternating gradient accelerators and beam studies using the 150 MeV proton FFAG", Jul. 22, 2016, pp. 1-31, No. 073G01, Publisher: Progress of Theoretical and Experimental Physics, Published in: https://doi.org/10.1093/ptep/ptw086.

Symon, K R., et al., "Fixed-Field Alternating-Gradient Particle Accelerators", Sep. 15, 1956, p. 1837 vol. 103, No. 6, Publisher: Physical Review.

Tahar, M. Haj, et al., "Tune compensation in non-linear Fixed Field Alternating Gradient accelerators", Published in https: //arxiv.org/pdf/1710.08772.pdf.

Tygier, S., et al., "Medical therapy and imaging fixed-field alternating-gradient accelerator with realistic magnets", "Physical Review Accelerators and Beams", Oct. 16, 2017, vol. 20, No. 104702, Publisher: The American Physical Society, Published in: DOI: 10.1103/PhysRevAccelBeams.20.104702.

Villani, Cedric, "Landau damping Notes for a course given in Cotonou, Benin, and in CIRM, Luminy", Jul. 2010.

Enge, Harald A., "Focusing of Charged Particles (edited by A. Spetier)", 1967, pp. 238-243, vol. 2, Publisher: Academic Press, Published in: New York, NY, USA.

* cited by examiner

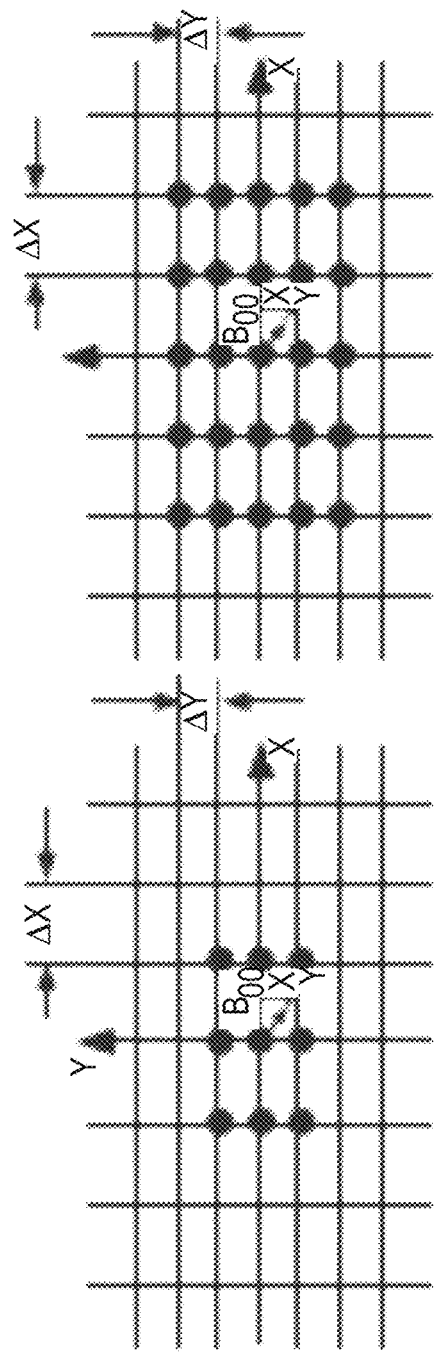
FIG. 8A
FIG. 8B
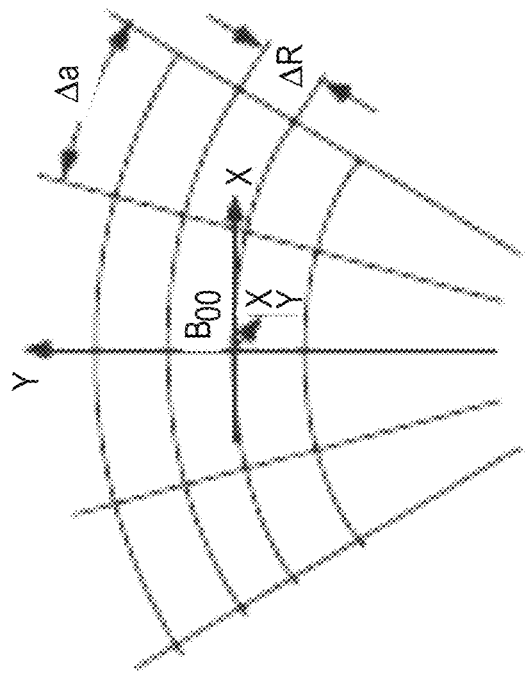
FIG. 8C

FIXED FIELD ALTERNATING GRADIENT ION ACCELERATOR FOR VARIABLE ENERGY EXTRACTION

CROSS REFERENCE TO RELATED APPLICATIONS

This application claims the benefit of provisional application 62/554,275, filed Sep. 5, 2018, the entire contents of which are incorporated herein.

BACKGROUND

Current treatments for some cancers include proton beam therapy to deposit high doses of energy in tissues several centimeters below the skin of a subject where some tumors lie. Compared with protons, heavier carbon ions deposit more energy in the tumor tissue, so they are considerably more destructive to the tumor. Heavier ions require fewer treatment sessions. For liver cancer, for example, a full dose requires 30 treatment days of proton therapy. With carbon, only four days are needed. Patients have been receiving treatment with carbon-ion beams in Japan, Germany, Italy, and China for years. Promising results have been obtained in Japan for treating pancreatic cancer with carbon ions.

The two most common accelerator designs for producing therapeutic proton or Carbon ion beams are synchrotrons and cyclotrons. But cyclotrons are designed to output proton beams of a single energy for which the orbit of the fastest beams have reached an output port of the cyclotron. Shortcomings of the cyclotron approach include a need for an energy degrader to reduce the proton beam energy from the maximum output. An even greater limitation is that cyclotrons cannot achieve the energy for a carbon ion therapy facility due to the weak focusing and isochronism problem.

Therefore, the need for energy variation for varying depth dose lead carbon ion therapy facilities to opt for a synchrotron. As the energy of the ions increases, a synchrotron varies its magnetic field strength in time by increasing currents to electromagnets in a carefully synchronized way (hence synchrotron) to keep the beam of ions in the same circular orbit at the bore hole of the accelerator. Synchrotron limitations include that the time varying magnetic field to control the ion orbits is less reliable, is complicated to operate, and the device is large in size. Furthermore, the beam size acceptance is small. That is, the angle error of the input beam to be accelerated is tight because of a dispersion problem. For example, ions entering the accelerator off the optimum angle increase their deviation from the center beam with each orbit.

SUMMARY

Applicants have identified a need for a design of a strong focusing fixed field machine with variable energy extraction and large beam acceptance. Strong focusing allows the device to reach a high energy needed for a carbon ion therapy facility (~400 MeV per atomic mass unit, amu, also called a nucleon herein) and a high beam current (number of nucleons). Fixed field magnets were chosen because such magnets are easier to operate, and allow the use of superconducting magnets, which reach higher magnetic field strength (thus controlling the orbits of more energetic particles in smaller spaces). These approaches provide an accelerator that is more compact in size and more reliable. The proposed design also provides variable energy extraction, no beam degrader, and less activation problems. The design also provides large beam acceptance by shaping the magnetic field using fixed field alternating gradient (FFAG) magnetics (to produce fixed field accelerators, FFA) that can be scaled to accommodate increasing ion energies. Ion energies are related to another parameter called the magnetic rigidity which is defined as the radius of the circular path an ion follows multiplied by the field in the magnet. Magnetic rigidity is usually specified in Tesla*meters. Magnetic devices designed for bending the path of a moving charged particle can be characterized by the maximum and minimum magnetic rigidity that it can handle.

In a first set of embodiments, a system for use as a compact medical ion accelerator includes a charged particle linear accelerator module and a pair of fixed field magnet assemblies. The linear accelerator is configured to accelerate a pulse of charged particles as a beam aligned along a first ray. The pair of fixed field magnet assemblies is configured to control the orbits of the pulse in the device by turning a moving charged particle 360 degrees within a first plane. The pair of fixed field magnet assemblies are disposed on opposite sides of the linear accelerator along the first ray and the pair of fixed field magnet assemblies are arranged with mirrored symmetry to each assembly to the other relative to a line perpendicular to the first ray and through a reference point in the first plane not on the first ray. Each assembly includes a pair of magnets for which a strength on the first plane of a magnetic field perpendicular to the first plane varies non-linearly along a radial direction from the reference point; and a superconducting magnet for which a strength on the first plane of a magnetic field perpendicular to the first plane varies along a radial direction from the reference point. The pair of magnets are disposed in the first plane with mirror symmetry about a line parallel to the first ray and through the reference point. The superconducting magnet is disposed between the pair of magnets on the first plane.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 8A through FIG. 8C are diagrams that illustrate example meshes to simulate particle position and movement in a spatially varying magnetic field, according to various embodiments;

DETAILED DESCRIPTION

Figure 1A:
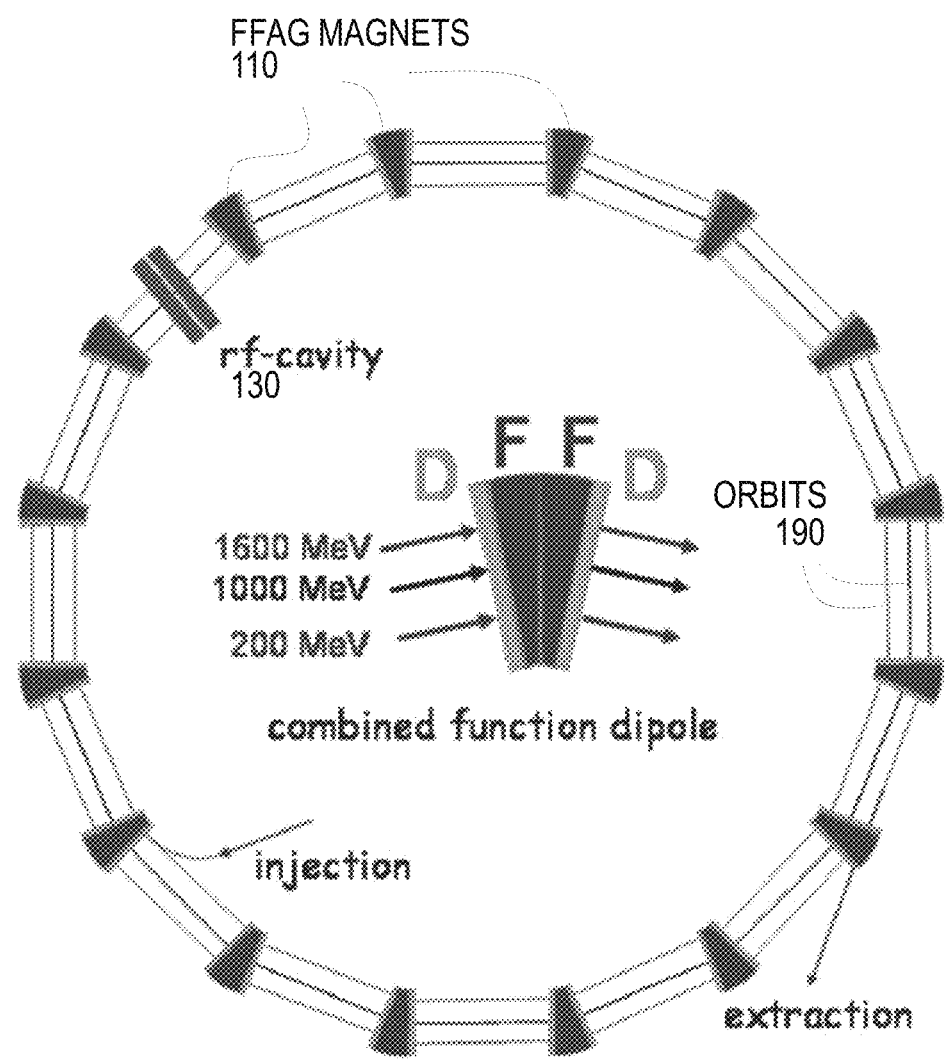
FIG. 1A is a block diagram that illustrates an orbital plane of an example fixed field alternating gradient (FFAG) charged particle accelerator.

A method and apparatus are described for a compact ion accelerator with variable energy extraction. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of accelerating protons (Hydrogen ions) from 22 million electron volts (MeV) per nucleon to 250 MeV/nucleon. The same footprint accelerator can also accelerate Carbon +4 ions (12 nucleons) from 5 MeV per nucleon to 64 MeV per nucleon. The kinetic energy of the ion is expressed in electron volts, the amount of kinetic energy imparted to one electron by a voltage difference of one volt. The reason for the difference in energies between protons and Carbon ions is that the Carbon ions each have a greater charge (e.g., +4) compared to the proton charge of +1, so the force exerted by the magnetic field is greater per ion. But because there are 12 nucleons, the force is less per nucleon, having only ⅓ the force per nucleon (+4/12 nucleons). In some embodiments, after accelerating the C+4 ion or H2+, another one or two electrons are stripped off, increasing the charge to C+5 or C+6 or 2 H+ and increasing the force per nucleon and allowing faster carbon ions or protons to be maintained in the accelerator. However, the invention is not limited to this context. In other embodiments, other magnets of greater or lesser strength are used, allowing other ions of greater or lesser charges to be maintained up to higher or lower energies in accelerators of the same or different size.

A microtron is a type of particle accelerator concept originating from the cyclotron in which the accelerating field is not applied through large D-shaped electrodes, but through a linear accelerator structure with curvature applied externally by magnetic fields. Early microtrons were designed to operate at constant electric field frequency and constant magnetic field (and thus do not necessarily use alternating gradient magnet arrangements) in the ultra-relativistic limit. Thus they are especially suited for very light elementary particles, namely electrons. In such early microtrons, due to the electrons' increasing momentum, the particle paths are different for each pass. The time needed for that is proportional to the pass number. The slow electrons need one electric field cycle in the linear accelerator, the faster electrons need an integer multiple of this cycle.

A Fixed-Field Alternating Gradient (FFAG) accelerator is a circular particle accelerator microtron concept on which development was started in the early 1950s, and that can be characterized by its time-independent magnetic fields (fixed-field, like in a cyclotron) and the use of strong focusing (alternating gradient, like in a synchrotron). As particles increase in kinetic energy, the radius of their orbit increases until the maximum energy is achieved and the particles exit the device. Because the orbits do not overlap, a continuous stream of particle can be accelerated. The radial increase of the magnetic field and thus the increase of the gradient, allows the device to reduce the orbit excursion considerably in comparison to cyclotrons. The magnet can be made superconducting or normal-conducting.

This concept is demonstrated in FIG. 1A. FIG. 1A is a block diagram that illustrates an orbital plane of an example fixed field alternating gradient (FFAG) charged particle accelerator. The curved trapezoidal figures are the footprint of the fixed field magnets 110, i.e., magnets that do not change their magnetic field strength with time. The magnetic field is directed perpendicular to the page and into the page for a positively charged ion, such as a proton or C+4, to move clockwise (or a negatively charged ion to move counterclockwise). In these embodiments, the magnets 110 serve only to maintain the particles in a focused beam that is forced to circulate in 360 degree turns, each 360 degree turn called an orbit 190. Because the magnets 110 are separated in space, the particles follow a straight path between magnets and then are turned, focused (F) and defocused (D) by encountering the spatially alternating magnetic field (in the pattern DFFD) at each magnet 110, then again go straight as they leave the field of the magnet 110. The particle thus experiences an alternating gradient magnetic field, hence the name. The magnets have greater strength at greater radius so that they can turn a greater energy particle the same angular amount. In a cyclotron, there is no alternation of the gradient and the magnetic field increases radially in order to keep the revolution time of the particles constant. Thus, a cyclotron is a weak focusing accelerator in comparison to a FFAG accelerator.

In FIG. 1A, the particles are accelerated in a radio frequency cavity (RF cavity 130) by the application of an electric field timed to attract the charged particles as they approach and to repel the charged particles as they recede from the RF cavity. After each acceleration, the particle has increased its momentum (and hence its energy) and thus takes more distance to turn the 360 degrees. Thus the next orbit 190 is further from the center of the orbits. Each successive orbit is further out as the kinetic energy of the ions increases. Thus the FFAG accelerator is designed to output particles of only a certain energy at the maximum radius, represented by the extraction ray. To sample lower energy particles, one would have to move the entire extraction mechanism radially inward to extract a lower energy beam or slow (degrade) the extracted beam at the maximum radius, which decreases energy efficiency (less energetic particles are extracted than were produced) and often has a cost in lowered beam current, also called beam intensity, due to fewer ions.

Figure 1B:
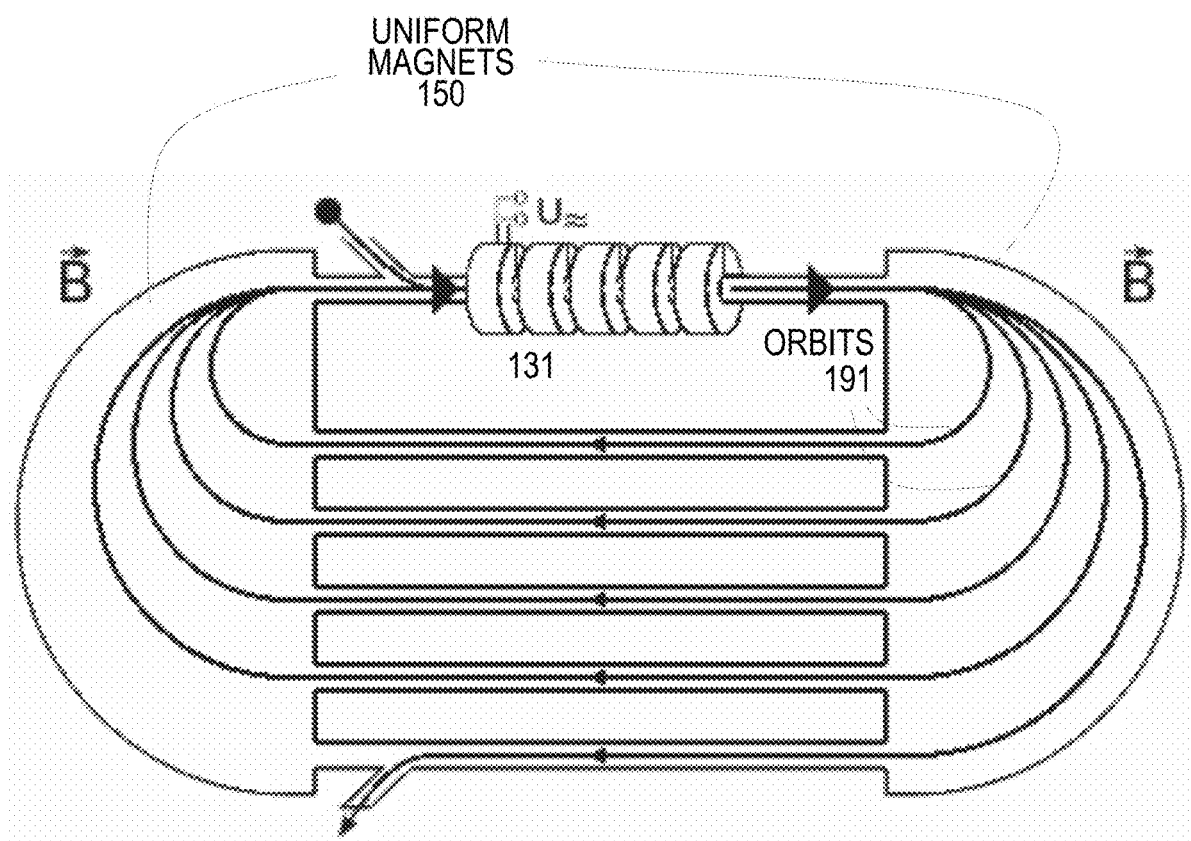
FIG. 1B is a block diagram that illustrates an orbital plane of an example single overlap racetrack microtron charged particle accelerator.

Particles in a racetrack microtron come from an external source. A racetrack microtron is a larger-scale microtron which uses two electromagnets instead of one. FIG. 1B is a block diagram that illustrates an orbital plane of an example racetrack microtron charged particle accelerator. Both electromagnets 150 supply a homogeneous magnetic field in a half-circle formed region, and the particles path between both magnets is not subject to a magnetic field and is therefore straight. Such straight portions of the orbits in the device are called straightaways or drift portions. One advantage of this is that the accelerator cavity 131 can be larger, enabling the use of different linear accelerator (linac) forms, and is not installed in a region with large magnetic fields. The linac is placed near the edge of the gap between the dee-shaped magnets 150. The remainder of the gap is used for focusing devices. The electron is readmitted to the linac after each revolution. This procedure can be repeated until the increasing radius of the particle's orbits 191 makes further acceleration impossible. The particle beam is then extracted by deflection into an experiment area or a further accelerator stage. In the illustrated design the magnetic fields are shaped to cause all orbits to follow the same path through the linac. Orbits in such a common path are said to overlap. In the illustrated embodiment there is a single overlap of orbits going through the linac, the return orbits do not overlap with each other.

Figure 2:
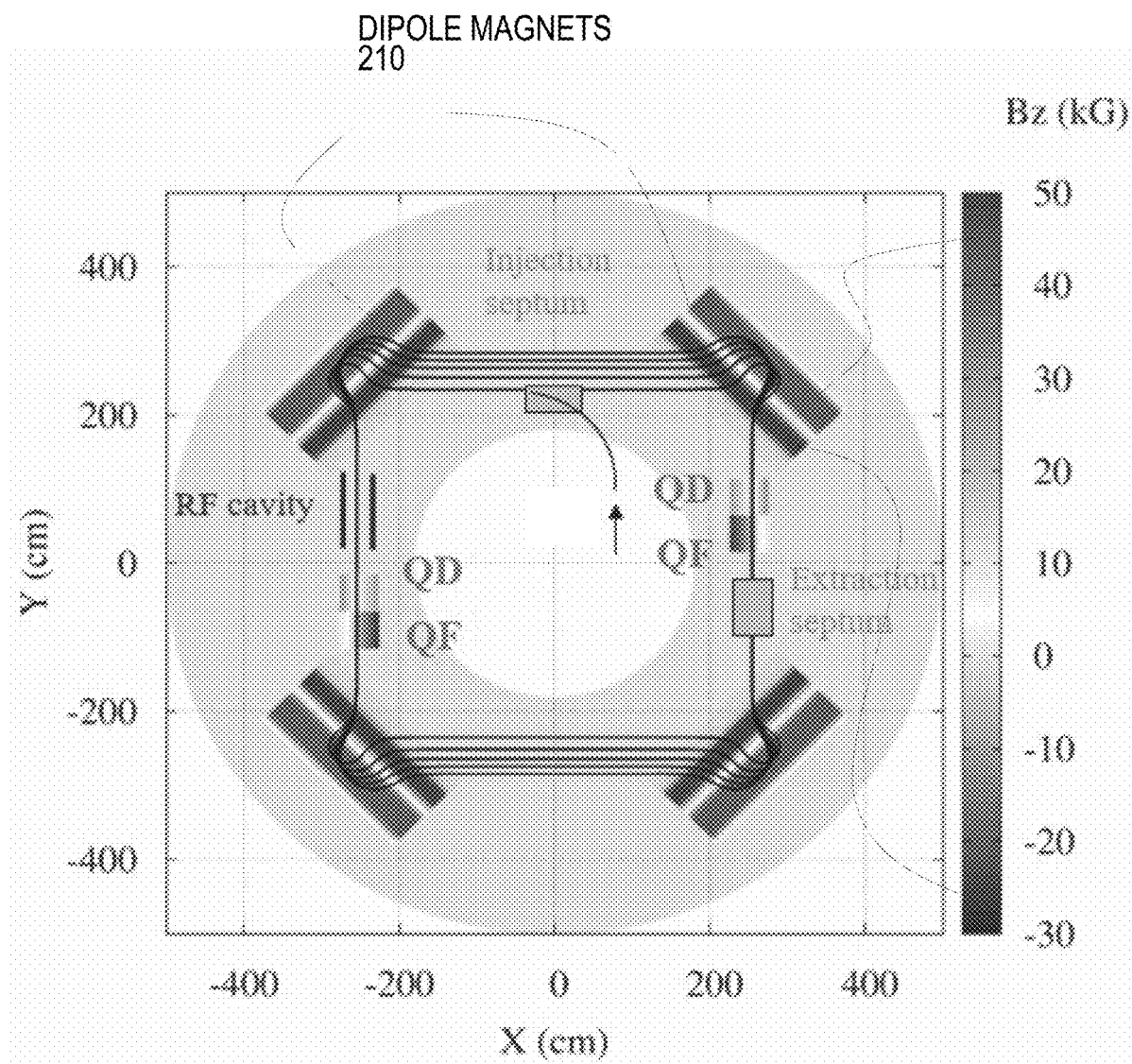
FIG. 2 is a block diagram that illustrates an orbital plane of an example double overlap racetrack microtron charged particle accelerator, according to an embodiment.

FIG. 2 is a block diagram that illustrates an orbital plane of an example racetrack microtron charged particle accelerator with two overlapping straightaway portions. In this embodiment, four dipole magnets 210 are used instead of two simple magnets to form two overlapping straightaways with all orbits following the same path, instead of just one overlapping straightaway used in earlier microtrons, as depicted in FIG. 1B. Thus, one straightaway with overlapping orbits can be used for the RF cavity, and the other overlapping portion for extraction. Insertion in this illustrated embodiment is with particles of the correct energy at the innermost orbit, e.g., in the section where the orbits do not overlap. FFAGs can be classified as linear or non-linear. Linear means that the magnetic field is a linear function of the radius from a center of the accelerator. Non-linear means that the magnetic field is a non-linear function of the radius from the center of the accelerator. Depending on the application, one type or another can be advantageous. FFAGs can also be classified as scaling or non-scaling. In a scaling FFAG, the number of betatron oscillations around a design orbit, due to momentum changes sending orbits further from the center in at least some portions of the accelerator, remains constant at all energies during the acceleration. In a non-scaling FFAG, the number of betatron oscillations varies with the energy. In FIG. 2, only dipole magnets are employed (with a linear field) which are useful for electrons, but cannot work for protons or heavy ions for fundamental reasons of stability. The orbits in this scheme are unstable and for this reason the quadrupole defocusing and focusing magnets, QD and QF, respectively, are used to trim the beams so that diverging particles are redirected to the proper direction. These QD and QF magnets are varied in time just like in a synchrotron accelerator, and add to the complexity of the system. Because of the time dependence of the field of the QD and QF magnets, e.g., the magnets must adjust their focusing strength to the energy of the particle, a continuous stream of particles is not supported; and pulses of length much less than one orbit ($<<2\pi$ radians or 360 degrees) are operated on at one time.

1. OVERVIEW

Figure 3A:
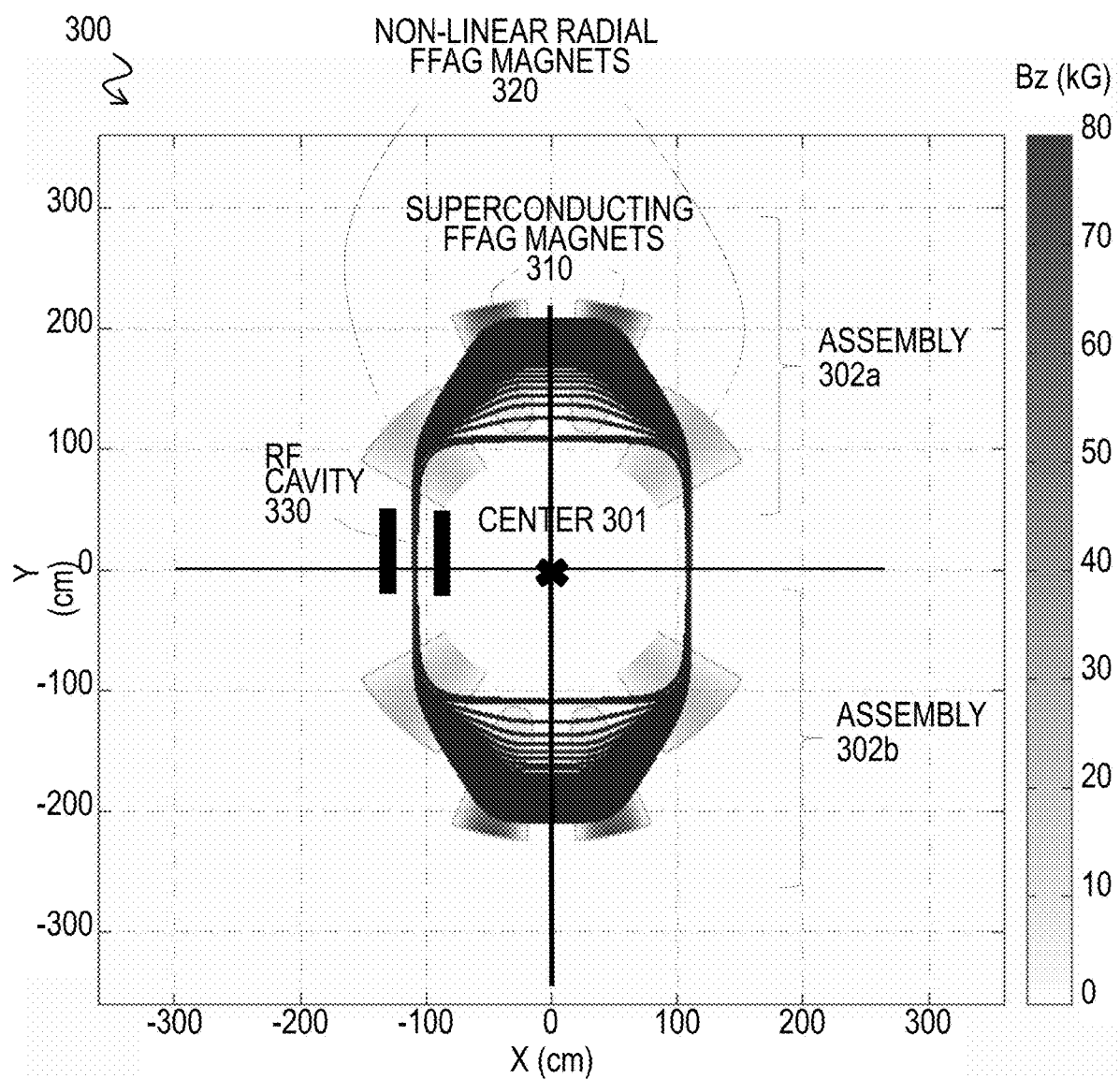
FIG. 3A is a block diagram that illustrates an orbital plane of an example double overlap racetrack superconducting magnet ion accelerator, according to an embodiment.

In several embodiments, a non-linear non-scaling FFAG is used. FIG. 3A is a block diagram that illustrates an orbital (X,Y) plane, also called horizontal plane, of an example double overlap racetrack superconducting magnet ion accelerator 300, according to an embodiment. This system 300 includes a charged particle linear accelerator module, such as RF cavity 330, and a pair of fixed field magnet assemblies 302a, 302b, either referenced as assembly 302. The linear accelerator 330 is configured to accelerate a pulse of charged particles as a beam aligned along a first ray, parallel to the y axis. A pulse of particles is aligned, as that term is used herein, if the centroid of the pulse is matched with the closed orbit of the accelerator, also called the design orbit, e.g., the average beam coordinates match with the designed radius and angle at any location. In the current design, this allows all the particles in the pulse that exit the RF cavity 330 to reenter the RF cavity 330 after one turn completion (called an orbit, herein). Thus, unlike conventional accelerators, the good field region of the RF cavity is reduced to that of the one ideal closed orbit, which greatly simplifies its design. Azimuth is an angle in the X,Y plane measured clockwise from the negative Y axis that passes through an entrance to RF cavity 330 and center 301. Radius is distance in the X,Y plane from the center 301. The Z axis is perpendicular to the X,Y plane.

The pair of fixed field magnet assemblies 302 is configured to control the orbits of the pulse in the device by turning a moving charged particle 360 degrees within a first plane (the X,Y orbital plane of FIG. 3A). The two assemblies 302a and 302b of the pair of fixed field magnet assemblies are disposed on opposite sides of the linear accelerator (e.g., RF cavity 330) along the first ray and the pair of fixed field magnet assemblies are arranged with mirrored symmetry to each other relative to a line (dashed line parallel with the x axis in FIG. 3A) perpendicular to the first ray and through a reference point (e.g., center point 301 in FIG. 3A) in the first plane not on the first ray.

Each assembly 302 includes a pair of FFAG shaped magnets 320 for which a strength Bz on the X,Y plane of a magnetic field perpendicular to the X,Y plane varies non-linearly along a radial direction from the reference point, which is not a dipole magnet; and one or more superconducting FFAG magnets 310 for which a strength Bz on the X,Y plane of a magnetic field perpendicular to the X,Y plane varies along a radial direction from the reference point. The one or more superconducting magnets 310 are disposed between the pair of magnets 320 on the X,Y plane, advantageously outside the influence of the magnetic fields of the magnets 320.

Figure 3B:
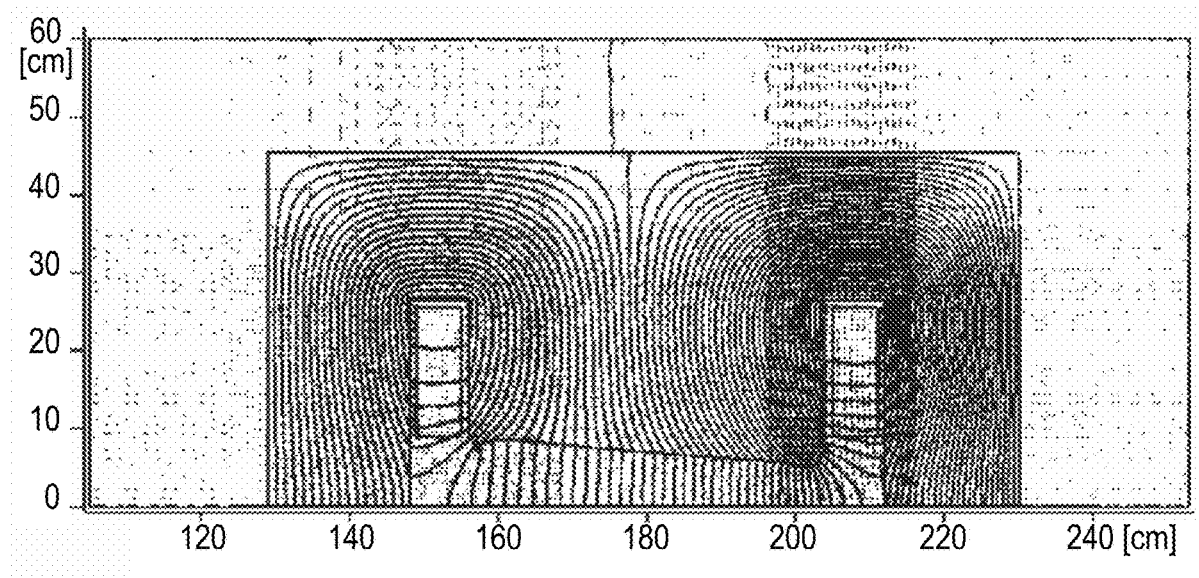
FIG. 3B is a block diagram that illustrates a cross section of an example permanent magnetic and magnetic field lines that achieves non-linear radial magnetic field that transforms between separate paths and a single path for separate orbits, that is used according to an embodiment.

FIG. 3B is a block diagram that illustrates a cross section of an example shaped permanent magnetic and magnetic field lines that achieves non-linear radial magnetic field that transforms between separate paths and an overlapping path for separate orbits. This is a permanent normal conducting (non-superconducting) magnet that can be used as each of the four FFAG magnets 320. In other embodiments, a superconducting magnet with the same field profile is used. The field strength in the permanent magnet is proportional to the gap between the metal poles and a non-linear magnetic gradient in the radial direction is achieved by implementing a non-linear change in the gap as the radial distance from the center of the device increases. For example, the field profile of the normal-conducting magnet is non-linear and scales as $R^k$, where R is the radius of the orbit and k is the average field index of the magnet (constant). Thus, the gap scales as $1/R^k$.

In this double overlap racetrack configuration, all orbits are aligned in the RF cavity 330, but separate into different radii, based on energy, after passing through one of the non-linear radial FFAG magnets 320. The curvature is then increased in superconducting magnet 310 to reduce the size of the system in the X direction perpendicular to the direction of acceleration by the RF cavity 330. The second non-linear radial FFAG magnet 320 then realigns the various orbits along the overlapping straightaway path, as the pulse leaves the assembly (e.g., 302a) and heads for the second assembly (e.g., 302b).

In some embodiments, each assembly comprises two sub-assemblies, each called a magnetic quadrant. Each magnetic quadrant turns the ion 90 degrees. The magnets of the first and the second magnetic quadrants are arranged with mirrored symmetry to each other relative to a line parallel to the first ray and through the reference point (e.g., center point 301 in FIG. 3A). This 90 degree bend is independent of the ion energy. Note that ions with higher energies will have orbits farther from the center of the machine in the direction of the injection path but will still exit the first assembly at 90 degrees. Note that, with this mirror configuration between the two magnetic quadrants, because the particles enter the second assembly at 90 degrees and at distance depending on their energy, they exit this quadrant on a ray anti-parallel to the injection path and equidistant from the center of the machine. This configuration guarantees that all orbits coalesce on overlapping racetrack straightaways on both the injection path and the return ray, independent of energy.

In some embodiments, the change of the revolution frequency with energy can be reduced which will enable fast acceleration schemes to be deployed (energy gains of the order of 10 s of keV).

Figure 3C:
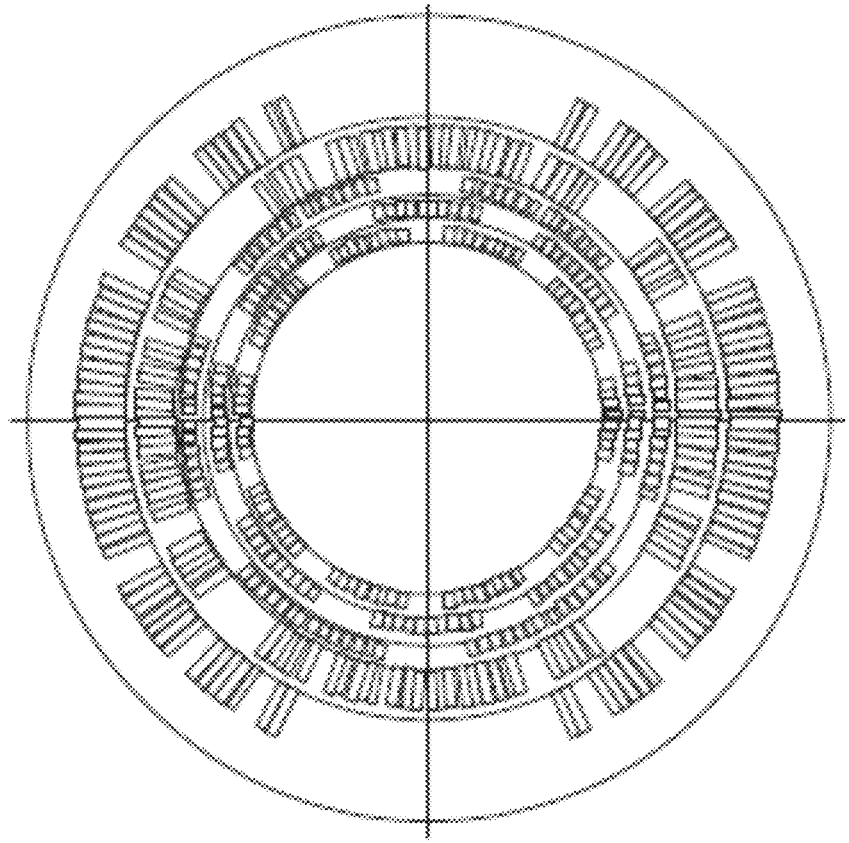
FIG. 3C is a block diagram that illustrates an example cross section of a superconducting magnet that serves as a component of one of the superconducting fixed field alternating gradient magnets of FIG. 3A, according to an embodiment.
Figure 3D:
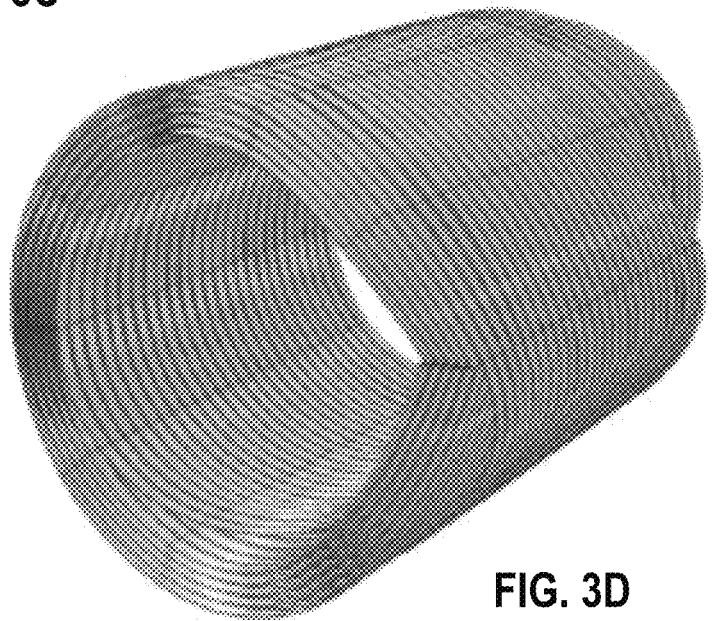
FIG. 3D is a perspective drawing that illustrates an example superconducting magnet that serves as one of the superconducting fixed field alternating gradient magnets of FIG. 3A, according to an embodiment.

FIG. 3C is a block diagram that illustrates an example cross section of a superconducting magnet that serves as a component of one of the superconducting FFAG magnets 310 of FIG. 3A. The current distributions are produced with a multi-layer coil each of which produces a pure multipole field component. FIG. 3D is a perspective drawing that illustrates an example superconducting magnet that serves as one of the superconducting FFAG magnets 310 of FIG. 3A.

Figure 3E:
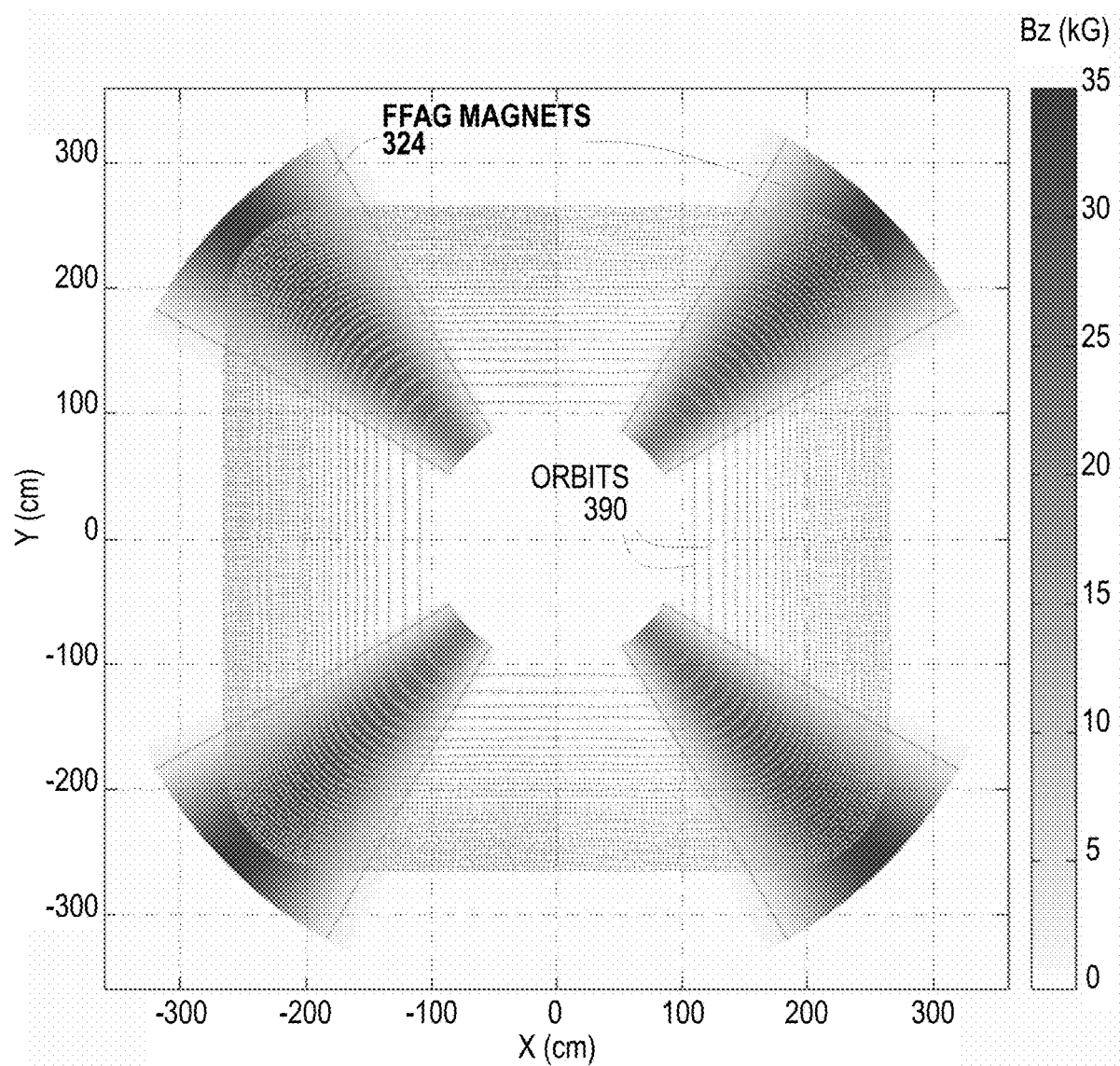
FIG. 3E is a block diagram that illustrates an orbital plane of an example intermediate design magnetic ion circulator, according to an embodiment.

The first step in designing the superconducting magnets consists in choosing the injection radius. This defines the size of the machine in the X direction (since all the orbits will overlap at the end). The second step is to start from a circular 4 sector machine where each sector consists of only one normal conducting FFAG magnet 324 as depicted in FIG. 3E. FIG. 3E is a block diagram that illustrates an orbital (X,Y) plane of an example intermediate design magnetic ion circulator, according to an embodiment. In the illustrated embodiment, the magnets are shaped so that the magnetic field increases as radius from the center of the device increases, thus each successive orbit expands outwardly less than the previous orbit expanded. This allows for a larger range of particle energies to be achieved before reaching the maximum design orbital radius for the device. The field of the magnet (normal conducting one in the 60 MeV/nucleon machine) is a superposition of non-linear terms along the radius R, e.g., $B(R)=B0+B1*R+B2*R^2$, where the only constraint is to achieve a large beam acceptance for all energies of interest.

Once this is achieved, the circular machine is transformed into a double overlap racetrack machine in which the design concept is to take the path of the injected orbit, and place the superconducting magnet relative to the injected path (the main constraint is that the fringe fields of the normal and superconducting magnets do not overlap). Then, the main constraint on the radial field profile of the superconducting magnet is that all orbits exit the superconducting magnet parallel to each other and with zero angle with respect to the X-axis for the design orbit.

Upstream of this superconducting magnet, is a normal conducting magnet shaped like that in FIG. 3B and used to cause the overlapping orbits on the incoming straightaway to separate into different radii based on energy. Next, by creating a mirror-symmetry of the two magnets around the dotted line parallel to the Y axis in FIG. 3A, and through the center point, this allows the orbits on the output side to overlap as well. Thus one magnet assembly 302 is complete. In some embodiments the two mirror image superconducting magnets 310 around the dotted line in FIG. 3A can be merged into a single superconducting magnet which has the same effect as both the superconducting magnets described above.

The second assembly 302b is a mirror image of the first assembly 302a using the same type magnets (or magnets with the same effect) about the dashed line parallel to the X axis in FIG. 3A and through the center point 301.

Figure 4:
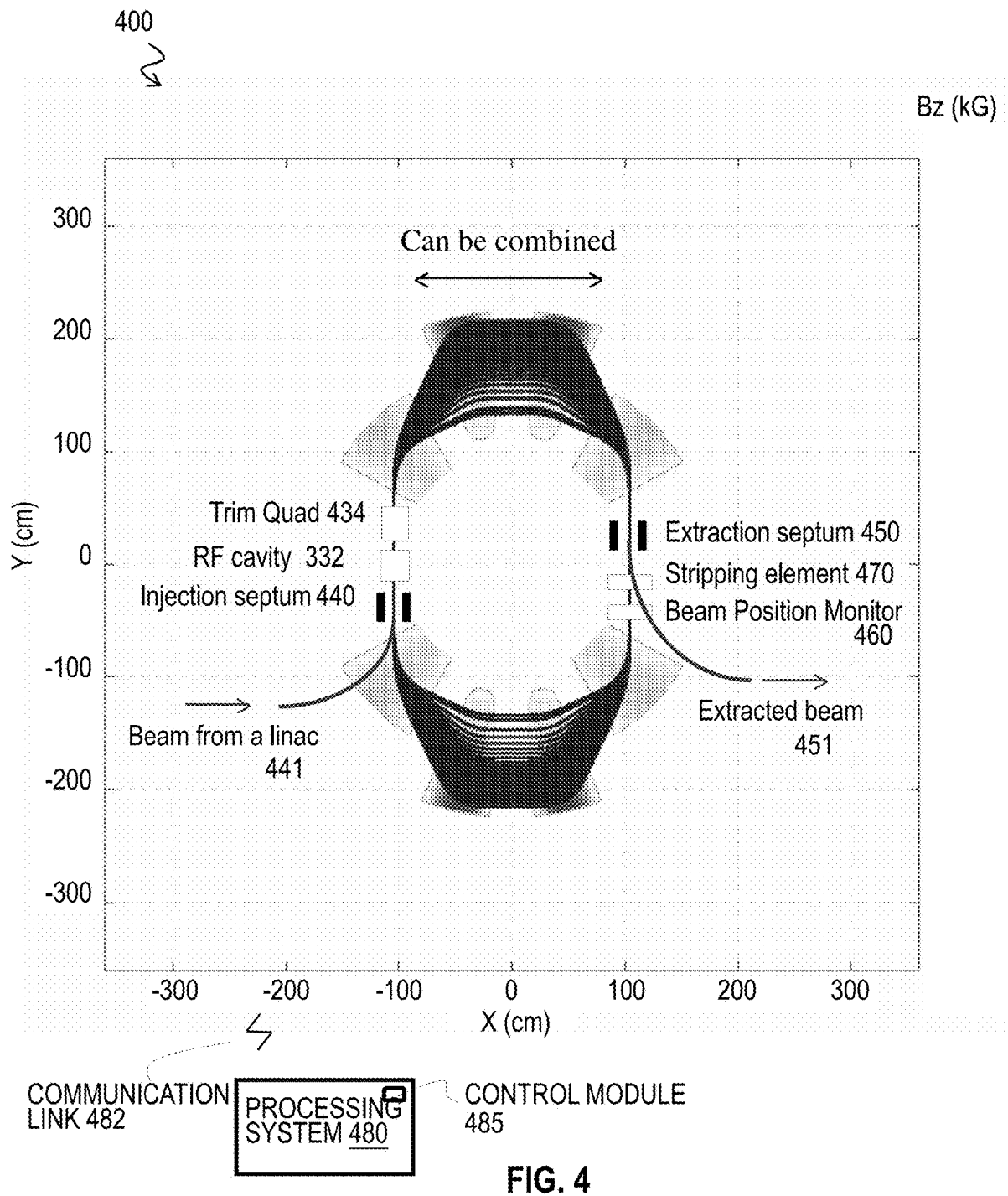
FIG. 4 is a block diagram that illustrates an orbital plane of an example double overlap racetrack superconducting magnet ion accelerator, according to another embodiment.

FIG. 4 is a block diagram that illustrates an orbital plane of an example racetrack superconducting magnet ion accelerator 400, according to another embodiment. This embodiment shows an embodiment 332 of the RF cavity, as well as an injection septum 440 and extraction septum 450 implied in the system 300 of FIG. 3A, but left off to avoid confounding the discussion above. The injection septum injects an ion beam 441 output by an external ion beam supply with the correct direction and at least the minimum energy to orbit in the system 300. One or several injectors can be employed to allow acceleration of several ion species, such as one for protons and one for carbon ions. An injector is another small scale accelerator that allows a particle to reach the injection energy for the system 400, e.g., at or above the minimum energy required to complete an orbit inside the device. This means that the final system will be a cascade of accelerators as is used commonly nowadays. The extraction septum extracts an ion beam 451 output by the system 400 after acceleration in the RF cavity 332 during one or more orbits. Note that, because all orbits overlap in the straightaways, the beam can be extracted using the same fixed septum 450 after any number of orbits up to the maximum number of orbits the system 300 can achieve, thereby giving variable energy output using a fixed ejection septum 450.

In the illustrated embodiment of FIG. 4, system 400 differs from system 300 by including one or more other components on either or both overlapping straightaways.

A trim quad 434 is one or more focusing or defocusing quadrupole magnets added to reduce the effects of resonance and other errors. As used here, resonance is a phenomenon that leads to unstable conditions of the particle motion. For instance, an angular deviation from the center ray of a beam pulse can be increased with each successive orbit when the number of beam oscillations in the horizontal or vertical plane obeys certain conditions, referred to as resonance lines. As used here, a number of oscillations are defined as the number of times a particle in the beam crosses the beam centroid after one full cycle (orbit) through the accelerator. When resonance conditions apply, at each acceleration in the RF cavity, this deviation is increased; eventually particles fall out of the beam pulse to collide with the vertical or horizontal sides of the system components. Some example embodiments described below simulate these resonances and the way to reduce the effect with the trim quad 434.

A beam position monitor 460 is included in some embodiments on either overlapping straightaway (e.g., the first ray or the second ray) to detect the position of the beam, e.g., by placing a beam detector in the path for one or more orbits of the test or delivery beam. The data collected from this device is used in some embodiments to tune the accelerator to provide the right operation of the trim quad 434 or RF cavity or other components of the system 400.

In some embodiments, a stripping element 470 is included. The stripping element is used to strip an electron from an ion in order to increase the charge of the ion. When the ion charge is increased, the magnets can contain the ion within the operational radius of the system 400 at higher energy, thus increasing the energy of the ion beam produced by the system 400. For example, in some embodiments the stripper is used for splitting a molecular hydrogen (H2+) beam into a beam of protons. In various embodiments, the stripper is disposed along the first ray or the second ray to dissociate particles in a molecular hydrogen beam into protons or to turn C+4 ions into C+5 or C+6 ions.

In some embodiments, one or more components, such as the injection septum 440, extraction septum 450, beam position monitor 460, trim quad, RF cavity 332 or stripping element 470, are controlled by a software or firmware control module 485 operating on a processing system 480, such as a computer system describe below with reference to FIG. 6 or a chip set describe below with reference to FIG. 7. The processing system 480 and the controlled component are in electronic communication by means of a wired or wireless communication link 482.

Figure 5:
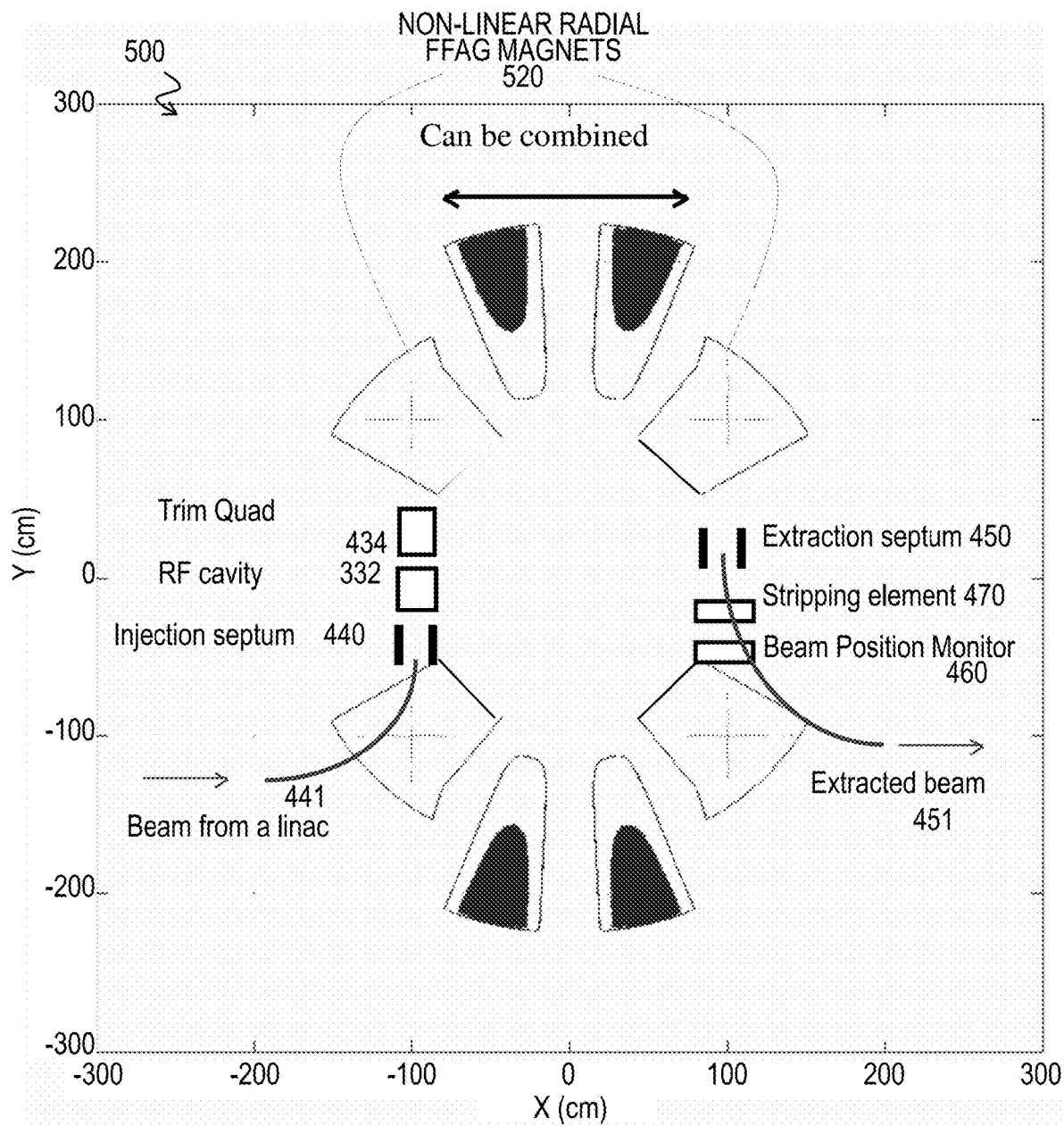
FIG. 5 is a block diagram that illustrates an orbital plane of an example double overlap racetrack superconducting magnet ion accelerator, according to another embodiment.

FIG. 5 is a block diagram that illustrates an orbital plane of an example double overlap racetrack superconducting magnet ion accelerator 500, according to another embodiment. In this embodiment one or more superconducting FFAG magnets or non-linear radial FFAG magnets are shaped to improve beam response characteristics, e.g., to maintain low dispersion at lower or higher energies. For example, the non-linear FFAG magnets 520 are differently shaped than the non-linear radial FFAG magnets 320 in system 300 and system 400. For example, the magnets 520 increase in angular width and edge angle with increasing radius.

Although processes, system components, and processors are depicted in FIG. 1A through FIG. 5 as integral blocks in a particular arrangement for purposes of illustration, in other embodiments one or more processes or components, or portions thereof, are arranged in a different manner, on the same or different hosts, in one or more databases, or are omitted, or one or more different processes or data structures are included on the same or different hosts. For example, in some embodiments the two superconducting magnets 310 in one assembly 302 are combined.

2. EXAMPLE EMBODIMENTS

Various example embodiments are described herein and their performances are simulated. One of the major concerns in ring accelerators (that does not exist in linear accelerators) is the crossing of the transverse resonances. Resonances, if not properly addressed, can lead to losses of the majority of ions in the beam. This is one of the main arguments why the microtron concept is not normally considered an attractive option for Carbon ions. Thus, it is desirable to come up with a ring accelerator concept in which the crossing of the transverse resonances is reduced or avoided. In a fixed field ring this can only be achieved by scaling FFAG type magnets (cyclotrons cannot achieve this). Scaling FFAG magnets have the property that their magnetic field is expressed as given in Equation 1a.

$$B = B_0 (R/R_0)^k \qquad (1a)$$

where B is the vertical (Z direction) component of the magnetic field in the median plane of the accelerator, R is the radial coordinate with respect to the center (e.g., 301) of the orbits, $B_0$ the reference field at $R=R_0$, and k is the average field index of the magnet.

In one embodiment, the vertical component of the field of the magnet is expressed as in Equation 1b.

$$B(R, \theta) = B_0 \left(\frac{R}{R_0}\right)^k F(\theta) \qquad (1b)$$

where $F(\theta)$ is a fringe field factor (also called a flutter function) that describes the azimuthal variation of the field of the magnet. For a four sector accelerator, it is sufficient to define one quarter of the entire orbit, which is $\pi/2$ radians of a full $2\pi$ orbit. In one embodiment, the flutter function is based on the Enge model and is given by Equation 2.

$$F(\theta) = \frac{1}{1 + e^{P_1(\theta)}} \times \frac{1}{1 + e^{P_2(\theta)}} \qquad (2)$$

Where the polynomials P describe the fringe field falloff at the edge of the magnet; and, the subscript 1 indicates the entrance of the magnet, and the subscript 2 indicates the exit of the magnet. In this embodiment, the polynomials are given by Equations 3 and 4.

$$P_1(\theta) = C_0 + C_1 \times (\theta - \theta_1) + C_2 \times (\theta - \theta_1)^2 + C_3 \times (\theta - \theta_1)^3; \theta_1 > 0 \qquad (3)$$

$$P_2(\theta) = C_0 + C_1 \times (\theta + \theta_2) + C_2 \times (\theta + \theta_2)^2 + C_3 \times (\theta + \theta_2)^3; \theta_2 > 0 \qquad (4)$$

The azimuthal spread, given by $\theta_1$ and $\theta_1$ can be varied to control the positioning of the magnets and the overall accelerator size, e.g., by maximizing a packing factor. Note that both polynomials have the same coefficients $C_i$ in order to impose symmetry on the fringe fields in this embodiment. In other embodiments the symmetry is not required; and, the coefficients may be different.

The effects of such fields on the trajectories of the ions in the accelerator can be simulated, e.g., with the ion ray-tracing code ZGOUBI, available at subfolder folder zgoubi of folder projects at world wide web domain sourceforge of super-domain net.

Step 1, Generate a median plane field map for a given lattice (a lattice refers to an accelerator with a specific configuration): the lattice is characterized by the flutter function F that is chosen in a way to represent a realistic field fall-off configuration (Enge model), the average field index k which can be varied, the width of the magnet, e.g., the field extent which is advantageously less than $\pi/2$, as well as the magnetic field $B_0$ defined at $R=R_0$ which determines the lower radius of the accelerator. The latter is optimized in order to provide enough space to place other elements such as the injection elements, the beam diagnostics and the linear accelerating device (linac).

Step 2. Use the tracking code ZGOUBI to track the particles in the field map. A 5×5 grid in the horizontal x,y plane, where y is in the radial direction and x is locally perpendicular to y, is centered on the node which is closest to the actual position of the particle. FIG. 8A through FIG. 8C are diagrams that illustrate example meshes to simulate particle position and movement in a spatially varying magnetic field, according to various embodiments. A 4th order interpolation polynomial is then used to determine the field and its derivatives using a 5×5 grid at the location of the particle at the center of the mesh. The field is expressed as given in Equation 5.

$$B(X, Y, 0) = \\ A_{00} + A_{10}X + A_{01}Y + A_{20}X^2 + A_{11}XY + A_{02}Y^2 + A_{30}X^3 + A_{21}X^2Y + \\ A_{12}XY^2 + A_{03}Y^3 + A_{40}X^4 + A_{31}X^3Y + A_{22}X^2Y^2 + A_{13}XY^3 + A_{04}Y^4 \quad (5)$$

The coefficients $A_{ij}$ are calculated by analytical expressions that minimize the quadratic sum S given by Equation 6.

$$S = \Sigma_{ij}(B(X,Y,0) - B_{ij})^2 \quad (6)$$

Where $B_{ij}$ the vertical component of the magnetic field at mesh point ij. The magnetic field at off vertical is calculated by assuming the mid-plane anti-symmetry and accommodating the Maxwell equations for the three components of the field.

Step 3. Use a fitting method to find the closed orbits for different energies. It is advantageous to verify that the tracking is symplectic. Symplecticity is a fundamental property in accelerators and results from the Liouville theorem which states that phase space is conserved for any fixed energy, e.g., for any given closed orbit. Another consequence of this is that the entropy is conserved and even beyond that, all the casimirs of the Vlasov equation are conserved. One way to verify the symplectic condition is to calculate the normalized emittance throughout the entire acceleration cycle or to compute the determinant of the one-turn transfer matrix of the accelerator. It is generally found that a time integration step size of 5 picoseconds, e.g., a longitudinal step size of approximately 1 millimeter, ensures good convergence of the numerical quantities as well as the symplecticity of the problem. FIG. 3E shows the results of the closed orbits calculation for several energies between injection and extraction in a 4-sector circular FFAG. We refer to each magnet as (m1).

Step 4. Ensure the stability of the particle trajectories in the transverse plane. For this, one constructs the one-turn transfer map of the lattice. This is achieved by tracking particles with small displacements from each closed orbit, e.g., from each different particle energy. The number of betatron oscillations per turn is thus computed for each energy from the transfer matrices. A second approach is also employed, in some embodiments. It involves performing a Discrete Fourier Transform on the position of the beam turn after turn and the tunes are identified as the frequencies with the highest amplitude peak (sometimes this is not true as the beam can be excited at other frequencies, therefore one performs cross-checks of the results with multi-particle simulations). This approach includes choosing the maximum amplitude to be the cell tune, i.e., the setting to keep the orbits of particles that are slightly off the design orbit close to the design orbit. The second approach is advantageous for two main reasons. One reason is that the tunes from the accelerated orbit can be calculated from this approach. In addition, the Beam Position Monitor (BPM) is usually used to record the particle phase space coordinates at different locations of the ring and for several turns which are then used to compute the tunes. The accuracy of the second approach is generally better than the first approach, in particular for non-linear systems. The calculated tunes are constant throughout the acceleration cycle for a given energy, i.e., a given closed orbit, and the phase advance per quadrant of the ring in FIG. 3E is limited to 180 degrees so that the tunes in both horizontal and vertical planes are less than 2, e.g., Qh or Qv<2.

Step 5. Transform the circular conventional FFAG into a racetrack configuration, with arbitrarily long overlapping straightaway (drift) portions, by replacing the 4-fold symmetry with a 2-fold symmetry machine. This is done by adding a second magnet (m2) for each sector and optimizing its field profile in order for the pair (m1+m2) to create a 90 degree bending angle for all energies. To achieve this, a fitting method is employed which consists of the following. Choose a location for the straights where the orbits overlap. This is always chosen to be the injection orbit. (An intermediate energy orbit can be chosen instead, in some embodiments. However, this will require reverse field in order to close the lower energy orbits). Then, for each closed orbit, track each particle through magnets (m1+m2). Magnet (m1) is fixed while the field of (m2) is varied with radius in order to guarantee that all particles exiting (m2) have a 90 degree bending angle. This is achieved using a fitting method as illustrated below. The keyword "FIT2" is employed in the "zgoubi.dat" input file. This is essentially a simplex method (Nelder-Mead method) which allows the adjustment of up to 20 variables in the input file. Essentially, any physical parameter defined in the input file can be adjusted (one can obviously also introduce a new physical parameter by adding a variable in the definition of the optical element in the tracking code). The parameter to vary is the angle T between the projection of the velocity in the X,Y plane and the X-axis. The requirement is that this angle be equal to zero for all energies. For this condition to occur, the field of (m2) is varied with radius, so it is varied for all energies. The result is dumped in an output file containing the magnetic field along the particle trajectories at all energies, thus allowing one to calculate the radial field profile of (m2) necessary to achieve the above mentioned condition. The content of this file is shown in FIG. 8D and FIG. 8E.

Figure 8D:
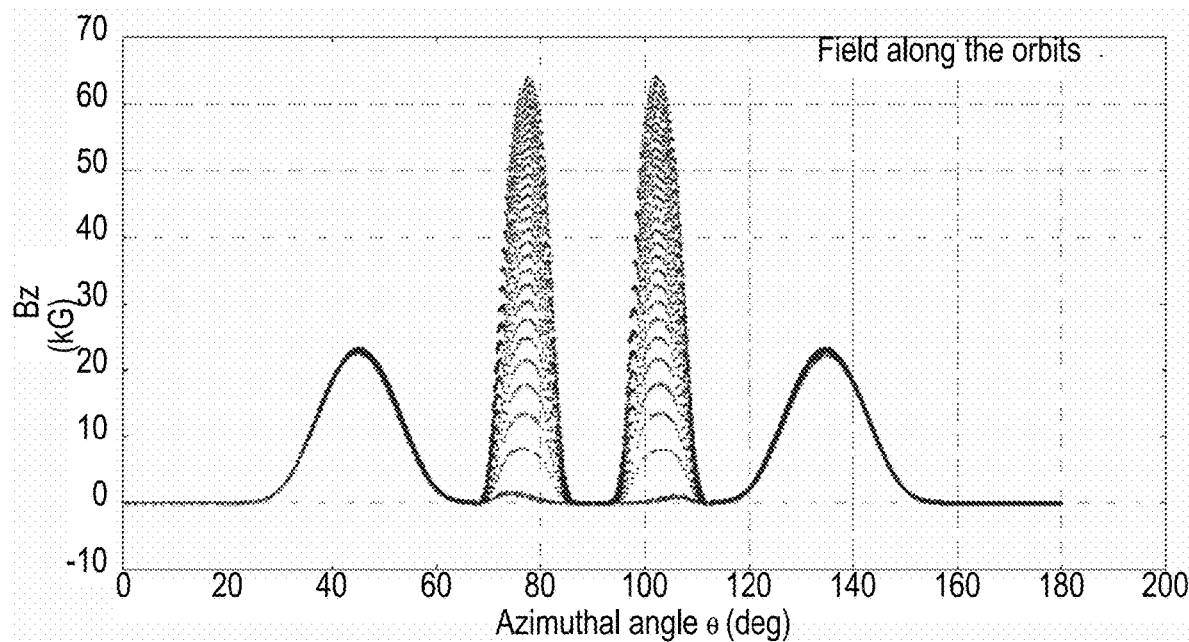
FIG. 8D shows magnetic field strength experienced along the orbit portion in one magnet assembly by carbon ions of kinetic energy from 5 MeV/nucleon to 60 MeV/nucleon, according to an embodiment.
Figure 8E:
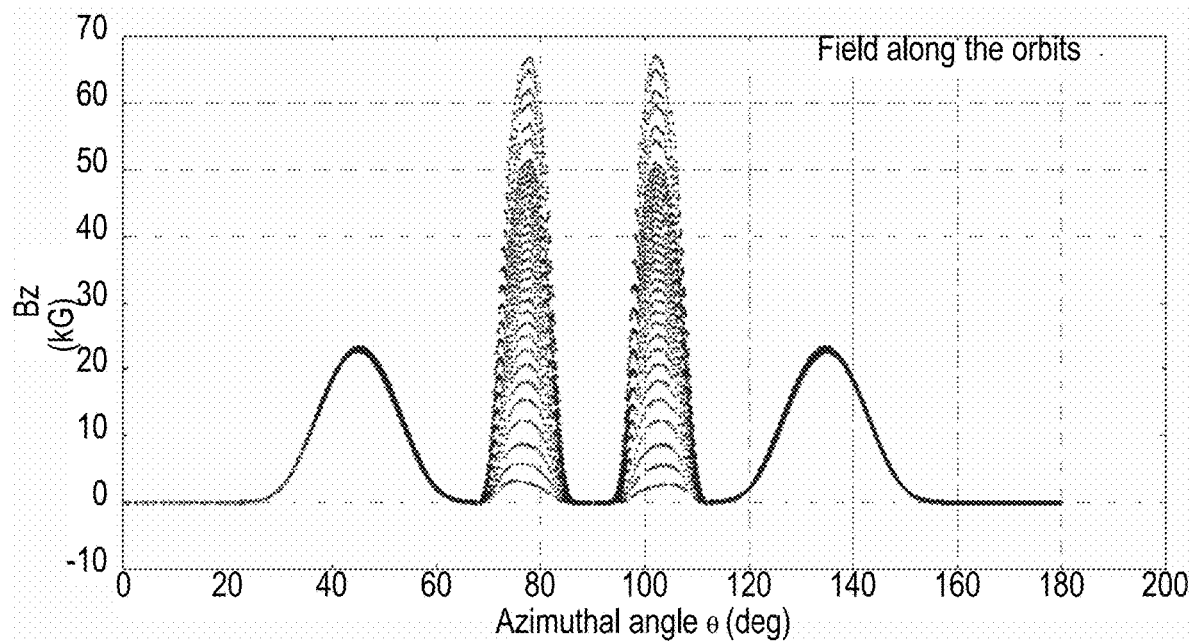
FIG. 8E shows magnetic field strength experienced along the orbit portion in one magnet assembly by protons of kinetic energy from 22 MeV/nucleon to 250 MeV/nucleon, according to an embodiment.

FIG. 8D shows magnetic field strength experienced along the orbit portion in one magnet assembly by carbon ions of kinetic energy from 5 MeV/nucleon to 60 MeV/nucleon, according to an embodiment. The horizontal axis indicates direction of beam relative to inserted beam direction in degrees, the vertical axis indicates magnetic flux density perpendicular to the orbit plane, Bz, in kilogauss (kG,1 kG=$10^3$ gauss=0.1 Tesla, T). As the ions increase energy on each revolution and pass through the RF cavity, the orbit slides further outward between angles from about 70 degrees to about 110 degrees, where the superconducting magnets provide sufficient flux, up to 70 kG, to have the desired effect on the orbit of the particles. At angles associated with the normal conducting magnets, centered on 45 degrees and 135 degrees, all kinetic energies essentially overlap and experience similar magnetic strengths. This reduces dramatically the size of the normal-conducting magnet and consequently the size of the ring. Similarly, FIG. 8E shows magnetic field strength experienced along the orbit portion in one magnet assembly by protons of kinetic energy from 22 MeV/nucleon to 250 MeV/nucleon, according to an embodiment. The field of the superconducting magnet can be reduced by combining the two central magnets together. This may have an impact on reducing the costs as well.

In an example embodiment, the values on the axes in FIG. 4 or FIG. 5 provide actual dimensions of the magnet assemblies in meters (m). A circular machine depicted in FIG. 3E, with an orbital diameter of about 6 m and a device footprint circumference of about 26 m, is transformed by including a second superconducting magnet with each permanent magnet into a double overlap racetrack FFAG shown in FIG. 4 with much smaller magnet sizes, an orbit diameter of about 4 m, and a device footprint circumference of only about 13 m. Strong focusing allows reaching high energy needed for carbon ion therapy facility (~400 MeV/nucleon) and high beam current. Fixed field magnets are easier to operate and allow higher magnetic field strengths to be reached; thus the device is more compact in size and more reliable. The overlapping orbits in the two straightaways allow variable energy extraction, and permit omitting a beam degrader thus leading to fewer activation problems. The device magnetic fields also allow large beam acceptance shape (in scaling FFAG). The footprint of the proton therapy machine will be the same as the carbon ion therapy machine. In such a machine, protons can reach energies up to 250 MeV and the closed orbits are the same in the two overlapping straightaway sections as in the Carbon ion therapy devices, which is simplifies both insertion and extraction for multiple different ions.

Figure 9:
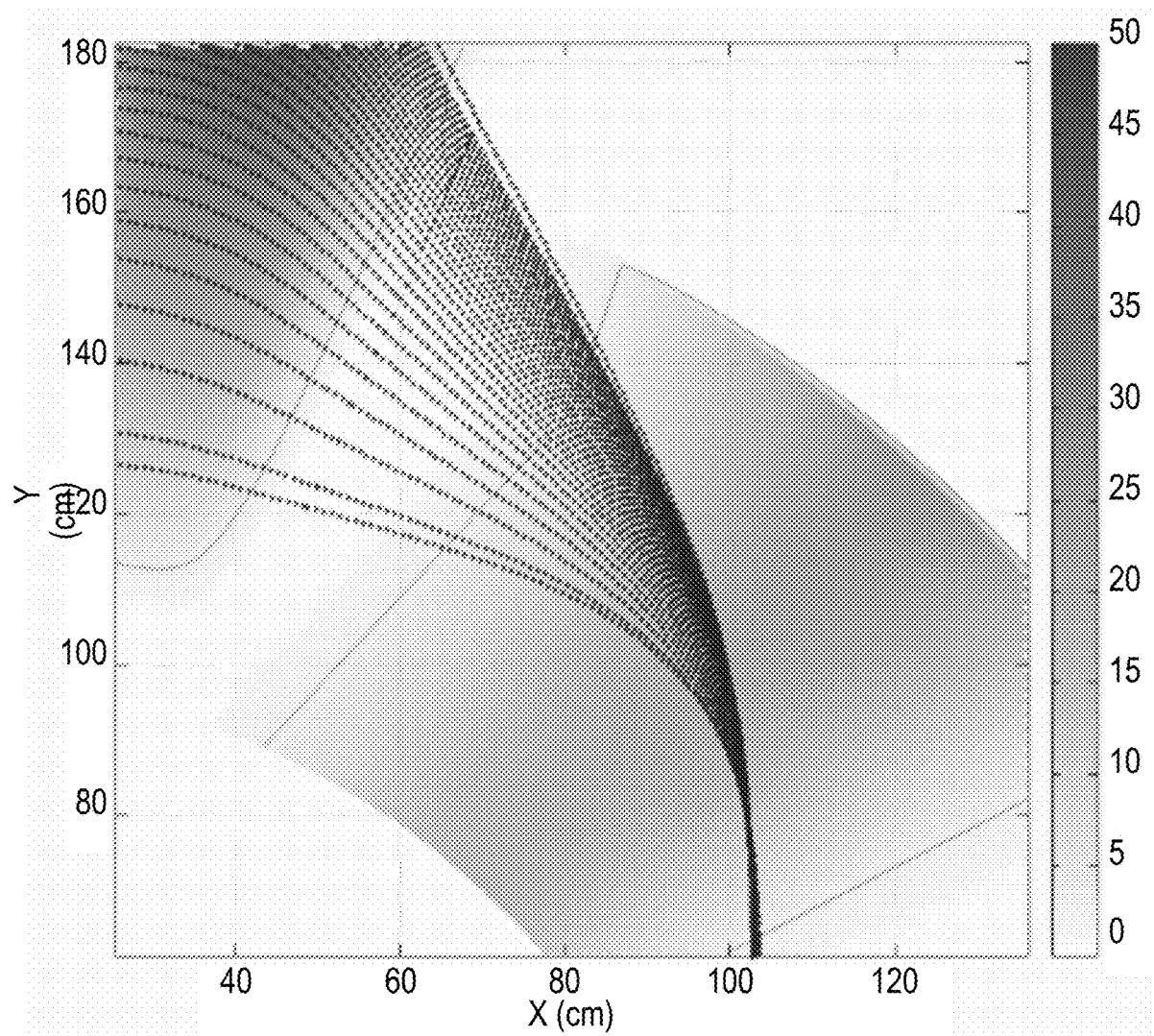
FIG. 9 is a diagram that illustrates shaping of a normal conducting magnet in a magnet assembly, according to an embodiment.

FIG. 9 is a diagram that illustrates shaping of a normal conducting magnet in a magnet assembly, according to an embodiment. In this embodiment, only the edge angle of the normal conducting magnet is modified to ensure no overlapping of the fringe fields. Simulations are performed to find an optimal shape. Two parameters are free in the simulation: the width of the magnet; and the edge angle of the magnet. In consequence, the field profile of the superconducting magnet is re-calculated using the fitting method in ZGOUBI in order to obtain the overlapping portions (also called drift or dispersion free sections), which simplifies both insertion and extraction for multiple different ions. As can be seen, the normal conducting magnet increases its width and edge angle with increasing radius of the orbit. Darker areas indicate stronger magnetic field strength, Bz.

The shaping is performed to help tune the orbits so that they are stable, e.g., remain closer to the design orbit. The quantities Qh and Qv are defined as the number of betatron oscillations around the design orbit, also called the beam center or closed orbit, per turn (e.g., per orbit) in the horizontal and vertical plane respectively. They are dimensionless quantities. For each given energy, the particle trajectory is tracked for one full turn (orbit) in the ring, and the number of times that such a particle crosses the optical axis (or the ideal or design trajectory orbit) represent the number of oscillations the particle performs around the ideal one. This number is therefore a measure of the focusing strength of the beam. The higher the value of Qh or Qv is, the more focusing there is.

Step six. The optics of the racetrack lattice are different from those of the ring lattice. Since the orbits do not scale, the chromaticity is no longer equal to zero, as expressed by Equation 6.

$$\frac{dq/q}{dp/p} \neq 0 \qquad (6)$$

Where q is the ring tune (number of oscillations per orbit) and p is the particle momentum. For this reason, one needs to ensure the stability of the particle trajectories. Thus the tunes are re-calculated and the edge angle of (m2) is adjusted as well as the gradient of (m1) in order to confine the tunes within one quadrant of the tune diagrams shown in FIG. 10A, therefore reducing or avoiding the crossing of integer and half-integer resonances. The optimized lattice is shown in FIG. 5. The corresponding tune diagram is shown in FIG. 10A.

Figure 10A:
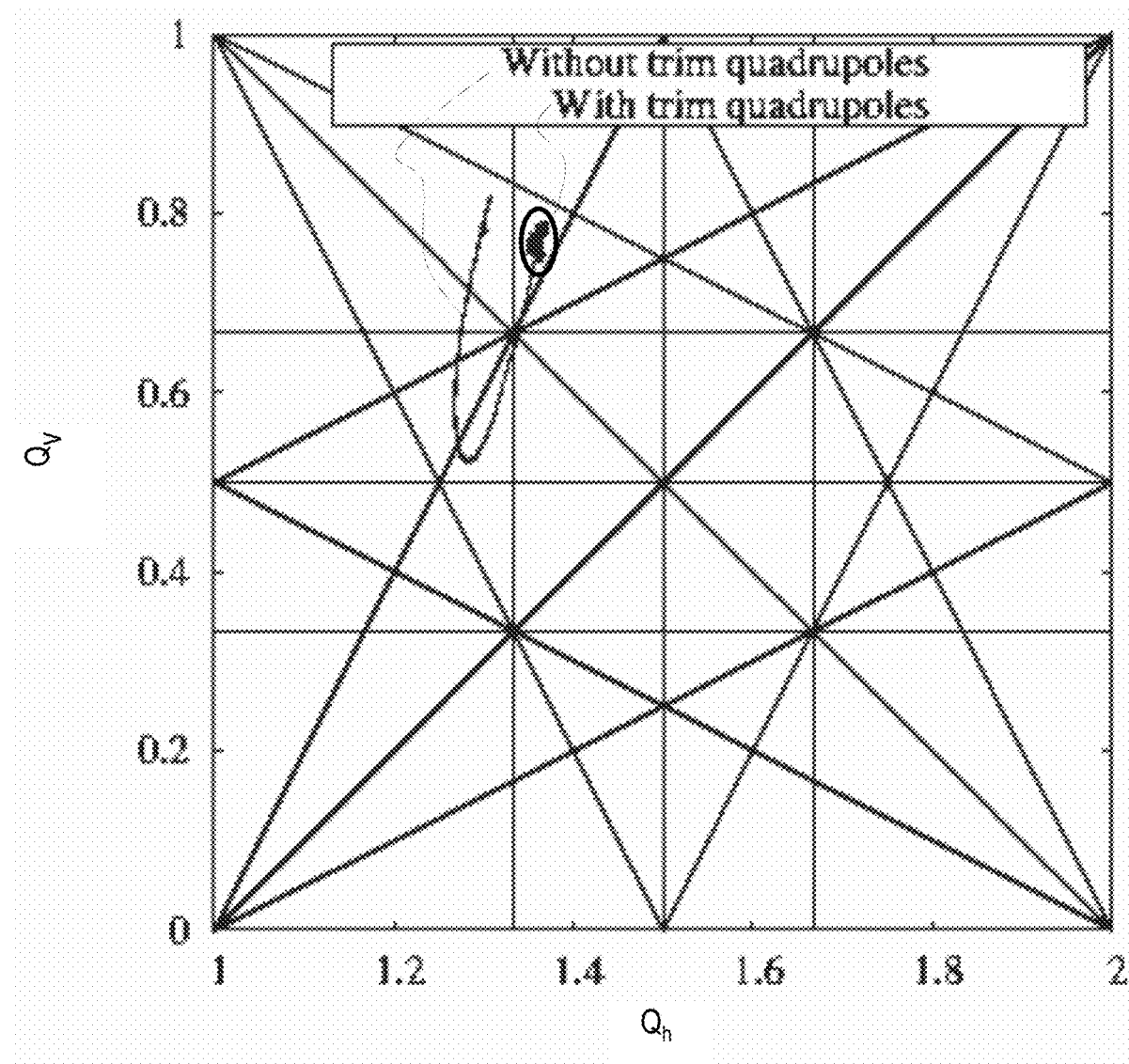
FIG. 10A and FIG. 10B are plots called tune diagrams that illustrate example focusing in devices with various shaped magnets, according to various embodiments.
Figure 10B:
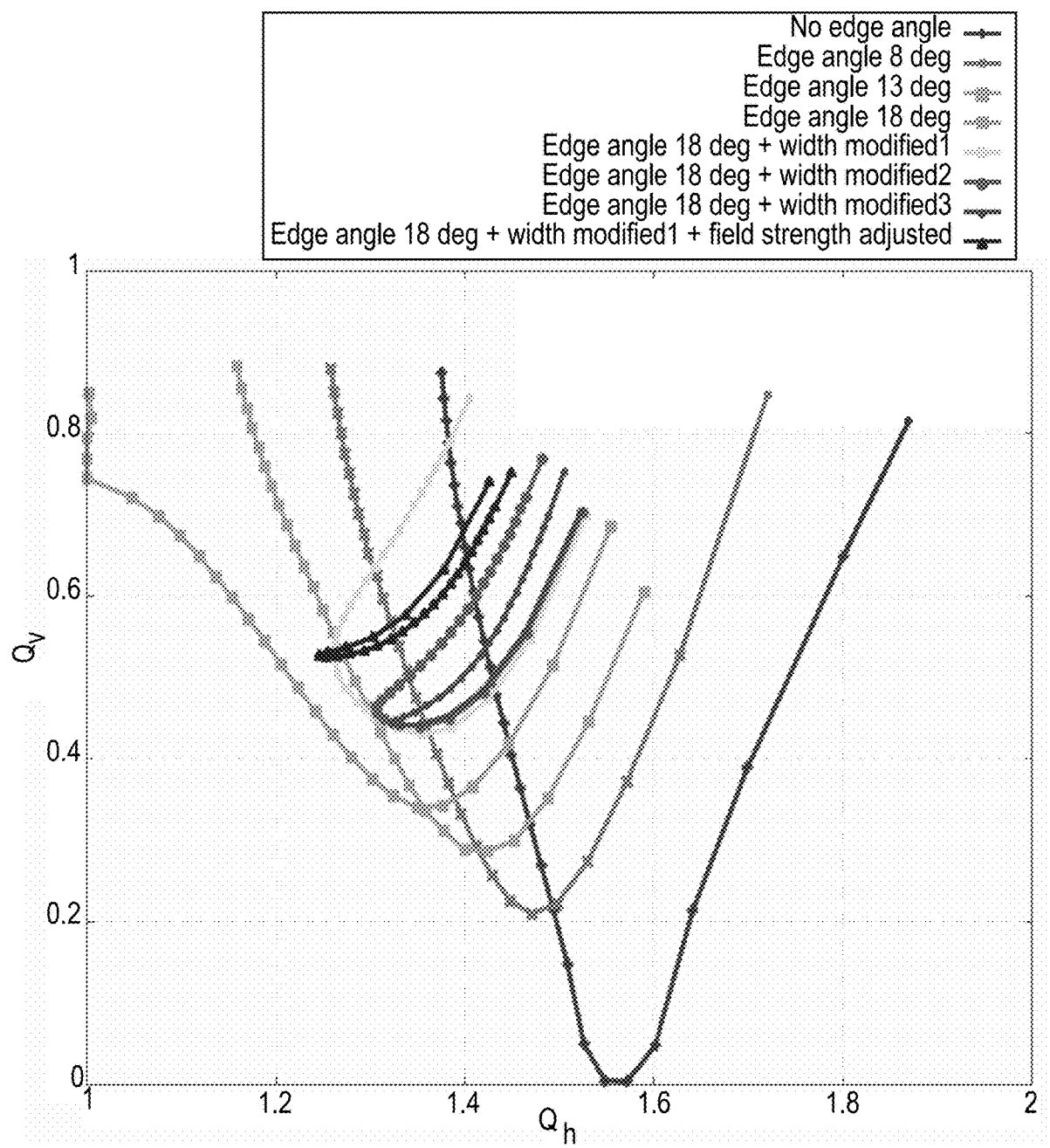

FIG. 10A and FIG. 10B are plots called tune diagrams that illustrate example focusing in devices with various shaped magnets, according to various embodiments. The horizontal axis indicates Qh and the vertical axis indicates Qv. Each point on a trace represents one given energy (there are 30 interpolated energies between injection and extraction depicted here); thus, each trace displays the results of the calculations for 30 different orbits. Each trace starts with the first orbit on the top right and ends with the last orbit on the top left. In practice, there will be on the order of 30,000 orbits by each particle in the accelerator. The shape of the eight traces would be exactly the same, each trace would simply have more points. Each line in the resonance diagram represents a resonance with different order (third order resonances lines connect ⅓ integer points in the tune diagram. Thus, each line represents a resonance satisfying the condition: aQh+bQv=c where a, b and c are integer constants and N=|a|+|b| is the order of the resonance. The lower N, the more detrimental the resonance can be. In general, the resonance crossing issue in accelerator physics is important up to third order. The Walkinshaw resonances are the ones that satisfy Qh−2Qv=integer; and, are known to be particularly detrimental to the beam. In FIG. 10A, one can see the crossing of several such resonances including a Walkinshaw resonance. The faster such a resonance is crossed, the fewer particles get caught up in the diverging beams that result.

FIG. 10B illustrates example focusing in devices with various shaped magnets, according to various embodiments. Each trace indicates a different configuration of magnets and shapes; and there are eight configurations designated by eight different point types: cross for no edge angle of the non-superconducting magnets; x for an edge angel of 8 degrees, three vertical bars for an edge angle of 13 degrees; large square for an edge angle of 18 degrees; small square for an edge angle of 18 degrees with a first modified width; circle for an edge angle of 18 degrees with a second modified width; diamond for an edge angle of 18 degrees with a third modified width; and triangle for an edge angle of 18 degrees with the first modified width and field strength adjusted. This last trace is for the optimized shape, which enables all three degrees of freedom: the width of the normal conducting magnet, its edge angle as well as its field strength. Essentially this provides a favorable k value in the equation of the field profile: $B=B_0 (R/R_0)^k$.

FIG. 10B shows that the vertical focusing is stronger, about 0.5 to about 0.7, for the more heavily modified magnet shapes and field strengths; and the average horizontal focusing falls between about 1.3 and about 1.5 for all modifications. It is found that the tunes are particularly sensitive to the edge angle of the normal-conducting magnet. A reduction of the tune space by at least one order of magnitude is achieved by shaping the non-superconducting magnets. This modeling considered 3 free parameters: field profile of the normal-conducting magnet; its width; and its edge angle. Even with such reduction in size, several resonances are still crossed.

Second order effects, such as dispersion or instabilities, e.g., remaining crossings of resonant oscillations, are corrected using trim coils in the superconducting magnet. However, the trim coils are envisioned, it is less useful to implement field correction in the normal conducting one since various energy orbits almost overlap in the normal conducting magnets.

Figure 10C:
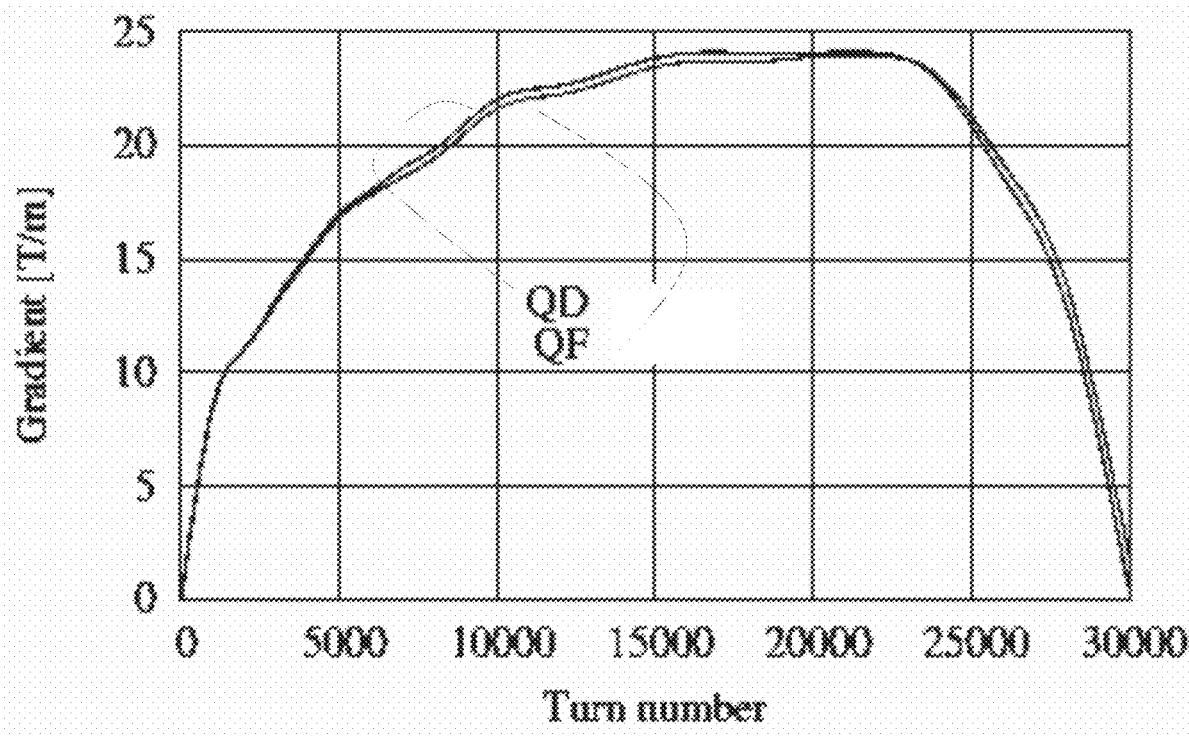
FIG. 10C is a plot that illustrates example temporal changes in spatial gradient of the magnetic field of focusing and defocusing trim quadrupole magnets, according to an embodiment.
Figure 10D:
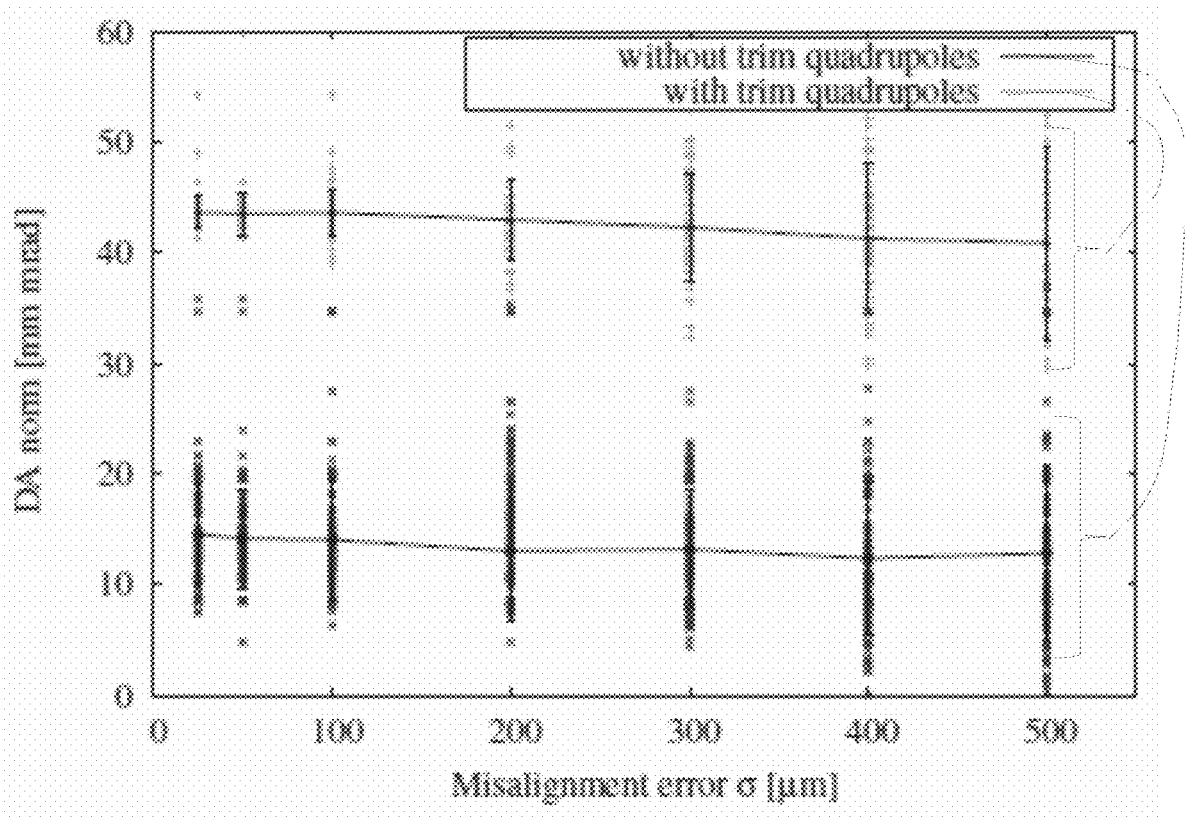
FIG. 10D is a plot that illustrates simulated dynamic aperture as a function of misalignment standard deviation, a, according to an embodiment.
Figure 10E:
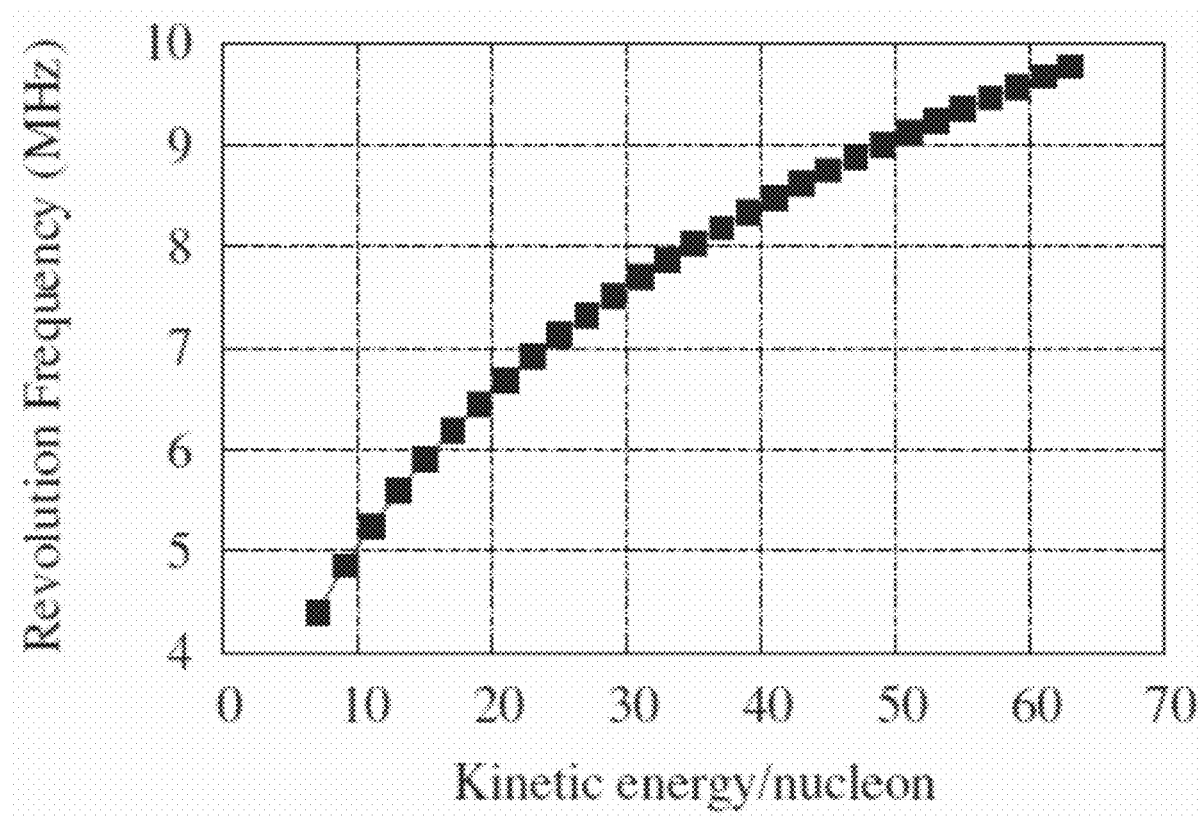
FIG. 10E is a plot that illustrates an example increase in revolution frequency with increasing particle kinetic energy, according to an embodiment.
Figure 10F:
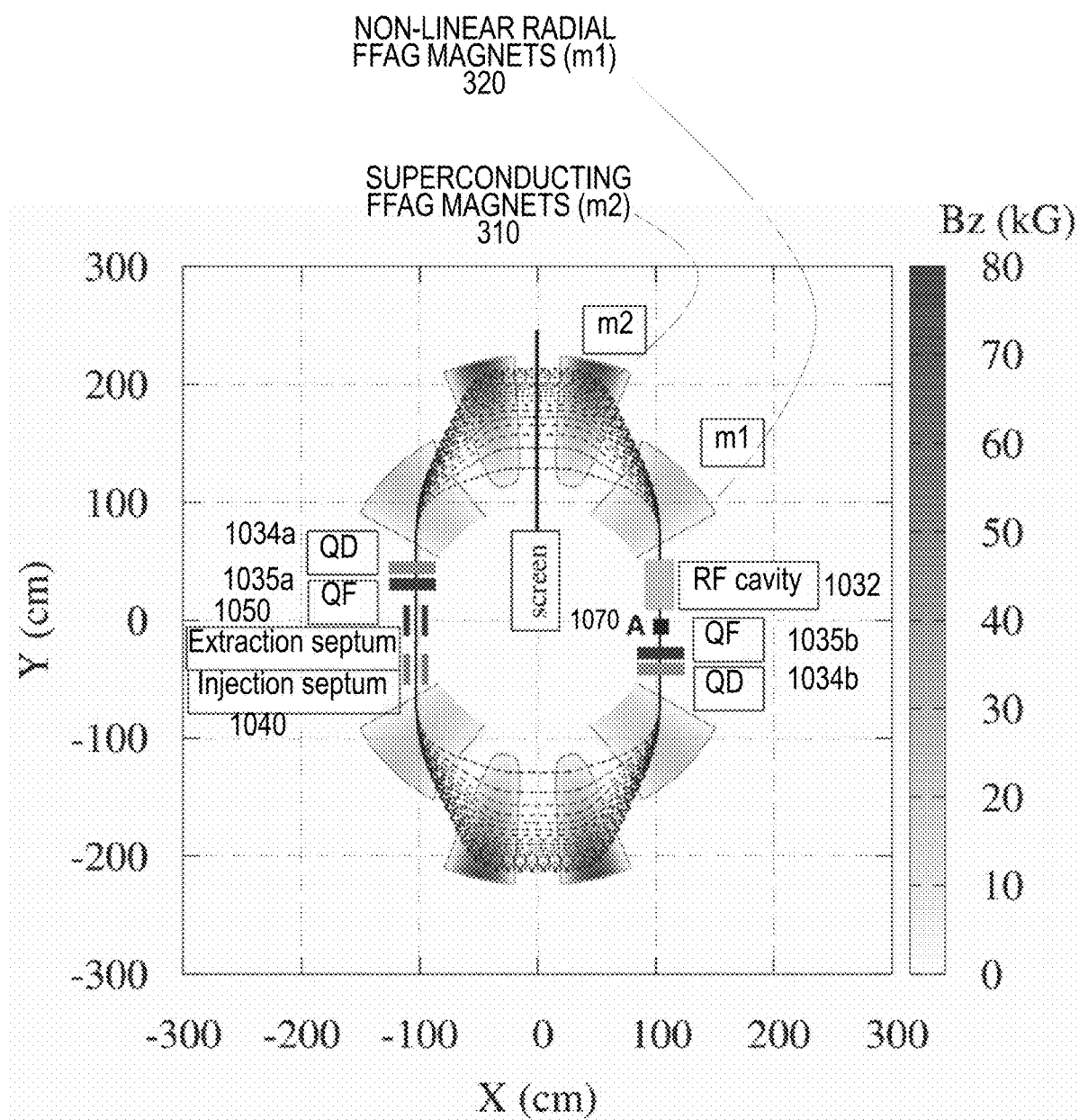
FIG. 10F is a block diagram that illustrates an orbital plane of an example double overlap racetrack superconducting magnet ion accelerator with 2-fold symmetry, according to another embodiment.

Step 7. As shown in FIG. 10A and FIG. 10B, several betatron resonances are crossed during the acceleration cycle of carbon ions from 8 MeV to 100 MeV/nucleon. This, combined with the designed imperfections will contribute to the increase of the amplitude of the betatron oscillation around the ideal closed orbit and thus to the beam losses. In order to remediate this problem, advantage is taken of the dispersion free long straight sections where one can place quadrupole magnets to modify the focusing and therefore to move away from the harmful resonances. Ideally, one would fix the number of betatron oscillations for all energies in order to avoid the crossing of any third order resonance. To achieve this, one constructs the one turn transfer map of the bare lattice. This is achieved by tracking particles with small displacements from each closed orbit, e.g., each different particle energy. Then, one adds the time varying focusing and defocusing trim quadrupoles, QF and QD respectively, (combined as trim quad 434 in FIG. 5) in a way that maintains the 2-fold symmetry of the accelerator as shown in FIG. 10F. This is of particular importance in order not to increase the number of betatron resonances that may be driven. The transfer map of the time-varying lattice is thus re-calculated using a MATHEMATICA code; and the gradients of the trim quadrupoles are determined for each particle energy in order to match the tunes of a chosen working point. The solution obtained is finally implemented in the tracking code ZGOUBI by adding the time-varying elements to the bare lattice. The results of the tune calculation from the accelerated orbit is shown in FIG. 10A by the trace with trim quadrupole magnets, which proves that the resonance crossing problem is overcome.

FIG. 10F is a block diagram that illustrates an orbital plane of an example double overlap racetrack superconducting magnet ion accelerator with 2-fold symmetry, according to another embodiment. In addition to the non-linear radial normal conducting FFAG magnets (m1) 320, and the superconducting FFAG magnets (m2) 310, this embodiment shows an embodiment 1032 of the RF cavity, as well as an injection septum 1040 and extraction septum 1050. The trim quad 434 of FIG. 4 is here replaced by two symmetrically placed focusing quadrupoles (QF) 1035a and 1035b on separate dispersion portions, respectively; and two symmetrically placed defocusing quadrupoles (QD) 1034a and 1034b on separate dispersion portions, respectively. In some embodiments, a stripping element 1070 is included.

In summary, the time varying field of the trim quadrupoles compensates for the monotonic behavior of the tunes in the bare lattice. For instance, increasing simultaneously the gradients of QF and QD allows one to increase both horizontal and vertical tunes. This applies to any bare lattice in the presence of field or misalignment errors of its main magnets. In addition, the working point of the lattice can be optimized in a way to heuristically maximize the overall beam transmission. The ramping rate of the magnets is shown in FIG. 10C. FIG. 10C is a plot that illustrates example temporal changes in the spatial gradient of the magnetic field of the focusing and defocusing trim quadrupole magnets as a function of the turn number, according to an embodiment. The acceleration cycle lasts about 3.5 milliseconds (ms, 1 ms=$10^{-3}$ seconds). QD is steeper at lower and higher energies due to fast variation of the tunes in the bare lattice. This real but small difference in the gradient of the QF and QD magnet overcomes the tune variations in both planes simultaneously.

Step 8. The sensitivity of the lattice to misalignment errors is determined. For this, one evaluates the Dynamic Aperture (DA) of the accelerator in presence of misalignment errors. The DA is defined here as the maximum initial horizontal normalized amplitude that the particle can have without any losses due to single particle dynamics effects over 30,000 orbits of the entire acceleration. This is a fundamental criterion in order to determine the tolerance of the lattice to imperfections. Each of the 12 magnets is transversely (horizontally and vertically) offset randomly using a Gaussian distribution with a standard deviation a and a cutoff at 3σ. For each error, 100 different patterns are tested and an initial normalized vertical displacement at 20 millimeters vertical times milliradians horizontal (mm·mrad) is chosen. The effect of the misalignment on the DA is shown in FIG. 10D. FIG. 10D is a plot that illustrates simulated DA as a function of misalignment standard deviation, a, according to an embodiment. One can see that with reasonable alignment errors (σ≈100 μm) the DA is essentially unchanged. However, the DA of the lattice with trim quadrupoles is almost 3 times larger than the DA of the bare lattice. This is mainly due to the third integer resonance crossing problem with the bare lattice, i.e. Qh=⅓. As expected, the lattice with the optimized working point has the largest DA and the maximum beam transmission.

In this double overlapping racetrack FFAG with trim quadrupoles embodiment, the synchronous particle orbit spirals outwards with increasing energy. Therefore, the time per orbit varies because of the increased speed of the particles and increased distance of the orbit. The RF phase of the cavity must evolve in such a way as to follow the change in the revolution frequency of the particle. FIG. 10E is a plot that illustrates an example increase in revolution frequency with increasing particle kinetic energy, according to an embodiment. FIG. 10E was calculated using the tracking in the fieldmap. The RF phase law is implemented accordingly.

In some embodiments trim quadrupole magnets are not used. The following figures demonstrate properties of beams in embodiments without such trimming: aside from the tune diagram with trim quadrupoles and the Dynamic Acceptance (DA), all plots demonstrate properties without trim quadrupoles.

Figure 11A:
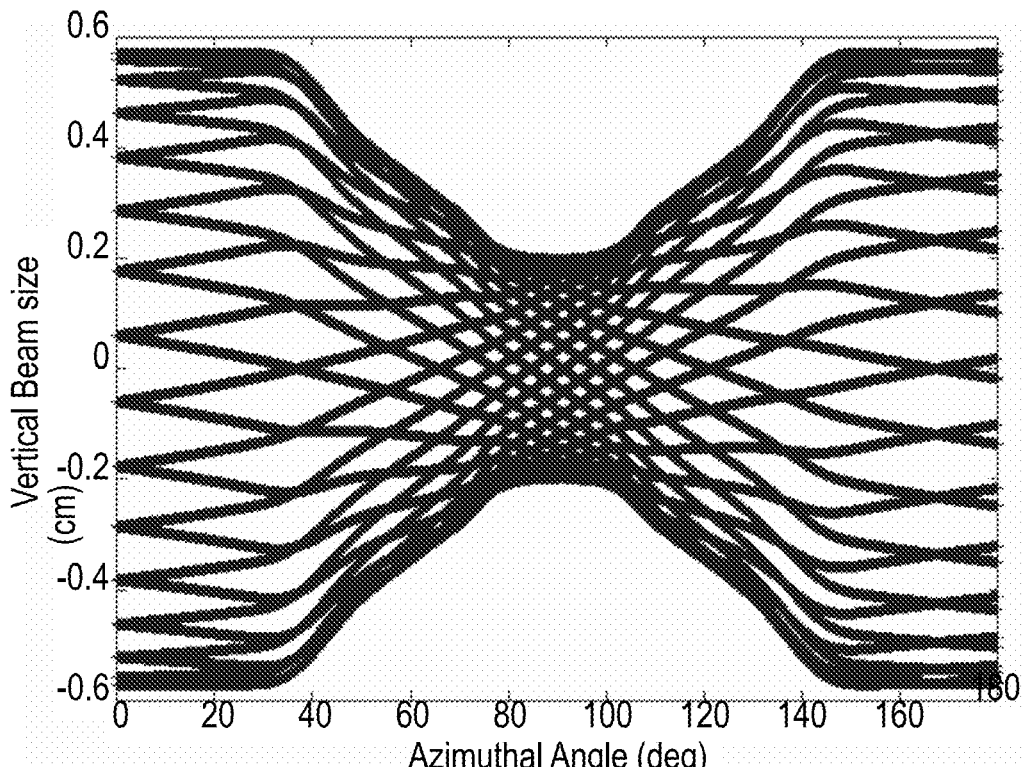
FIG. 11A is a plot that illustrates example vertical (perpendicular to the X,Y orbital plane) beam envelope as a function of azimuth through one magnet assembly, according to an embodiment.
Figure 11B:
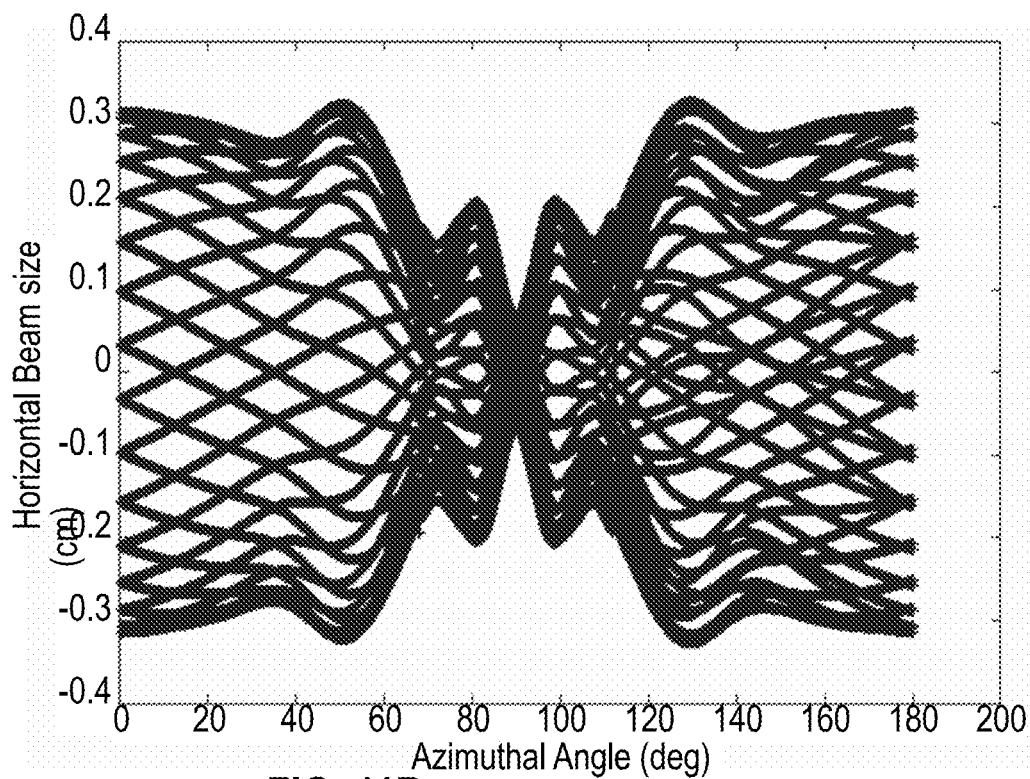
FIG. 11B is a plot that illustrates example horizontal (in the X,Y orbital plane) beam envelope as a function of azimuth through one magnet assembly, according to an embodiment.

Ray traces of Carbon ion trajectories for an envelope of Carbon ions about 1.2 cm wide in the vertical plane and about 0.6 cm wide in the horizontal plane were plotted to examining focusing and dispersion of various embodiments. FIG. 11A is a plot that illustrates example vertical (perpendicular to the X,Y orbital plane) beam envelope as a function of azimuth through one magnet assembly, according to an embodiment. FIG. 11B is a plot that illustrates example horizontal (in the X,Y orbital plane but perpendicular to the beam direction) beam envelope as a function of azimuth through one magnet assembly, according to an embodiment. As can be seen in both plots, beam envelope decreases due to focusing by one or more superconducting magnets in the center of each assembly, e.g., at azimuthal angles between about 80 degrees and about 100 degrees. This shows that computing the matching conditions allows a beam of particles to be injected with the right conditions (beam size, angles) and have the beam perform a periodic motion around each closed orbit, suitable for repeated acceleration. The periodic motion is ensured, with no slope in the drift space at 0 degrees where the RF cavity (e.g., 332) is placed, and at 180 degrees where the extraction septum (e.g., 450) is placed, given that the design ensures that the dispersion function vanishes at these locations.

Figure 12:
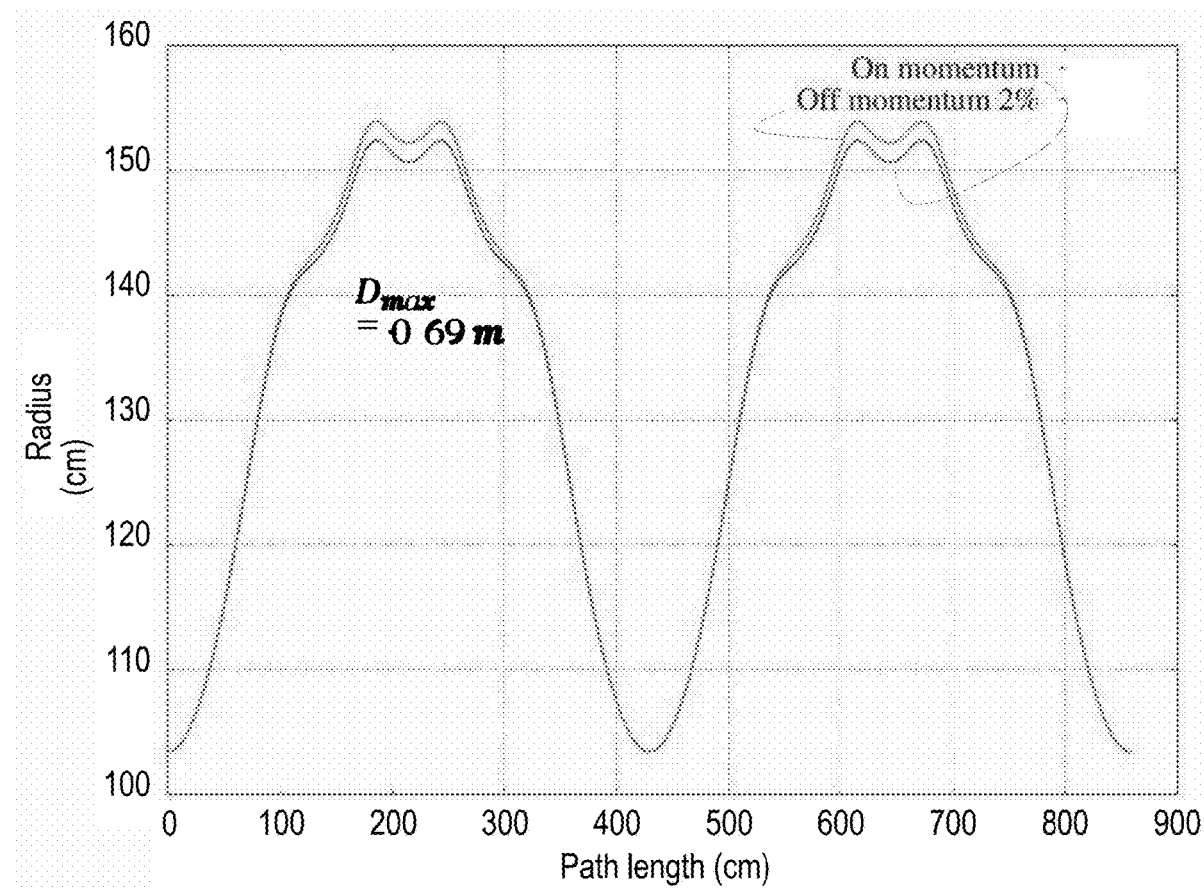
FIG. 12 is a plot that illustrates example radial distance as a function of orbital path distance through both magnet assemblies, according to an embodiment.

Ray traces of Carbon ion trajectories for Carbon ions with varying momentum (p) were plotted to examining focusing and dispersion. FIG. 12 is a plot that illustrates example radial distance (in cm) as a function of orbital path distance (in cm) through both magnet assemblies, according to an embodiment. As can be seen, particles of different momentum (about 2% difference) separate within each assembly, especially between normal-conducting magnets in each assembly at about 200 cm and about 650 cm of path length, but occupy the same radius between the two assemblies at about 400 and about 800 cm of path length. That is, the overlapping racetrack straightaway portions at about 400 cm and about 800 cm are dispersion free.

Figure 13:
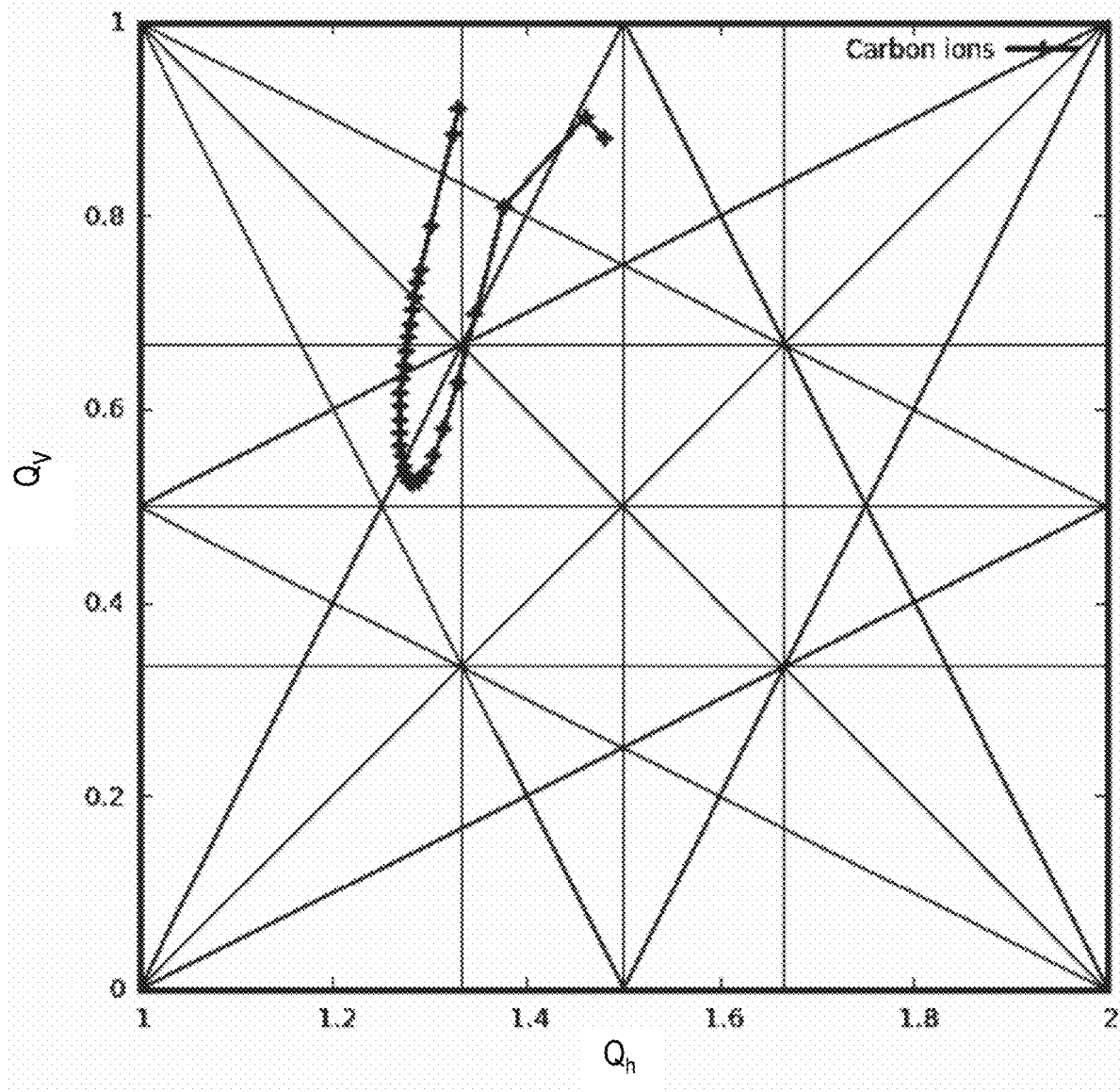
FIG. 13 is a tune diagram that illustrates example focusing for Carbon ions without trim magnets, according to an embodiment.

FIG. 13 is a tune diagram that illustrates example focusing for Carbon ions without trim quadrupole magnets, according to an embodiment. Even with shaping of normal magnet widths and edge angles, several resonances are crossed. At such resonances, some particles exit the beam and cannot be recovered, reducing output. For example, when crossing a third integer resonance, particles stream along a "resonance island" where a fraction of the particles become trapped. These islands carry the trapped particles away from the ideal orbit at ever increasing distance where the particles are lost to interactions with the sides of the accelerator. Even so, beams with a useful number of particles can be produced. Such beams have a spread of phases that survive the various resonance crossings at the extraction energy.

Figure 14A:
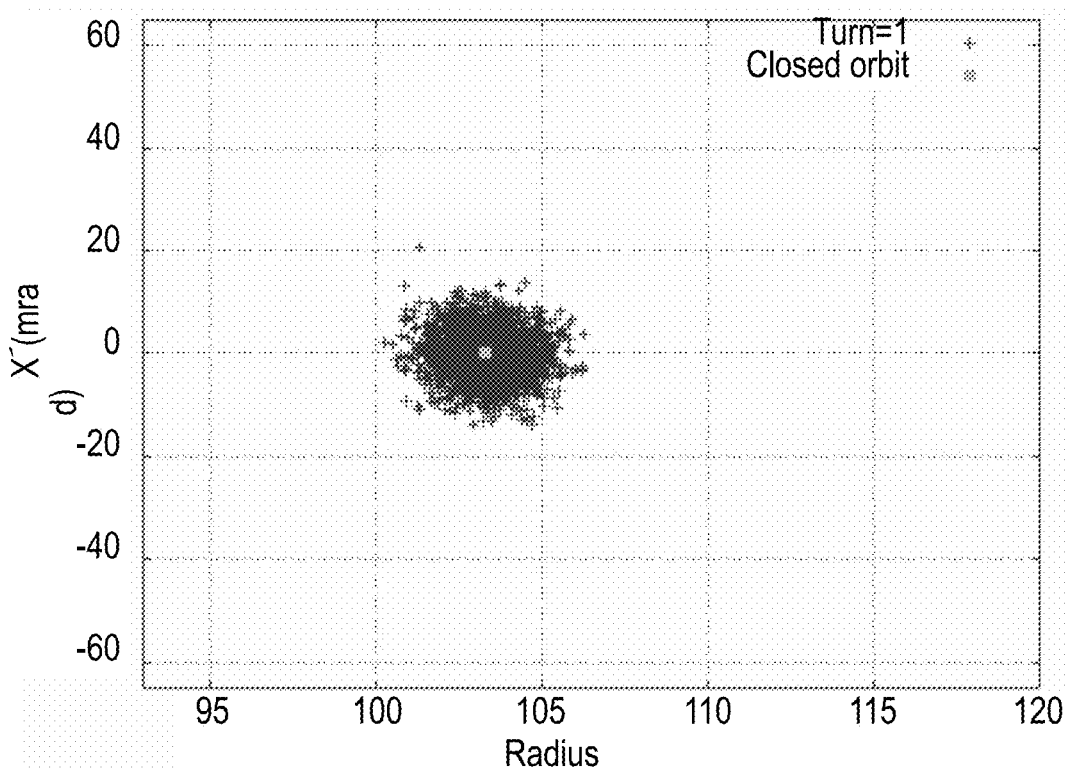
FIG. 14A and FIG. 14B are phase space diagrams that indicate the spatial displacement of particles that have a phase difference from the design orbit, in the horizontal plane and vertical plane, respectively, according to an embodiment.
Figure 14B:
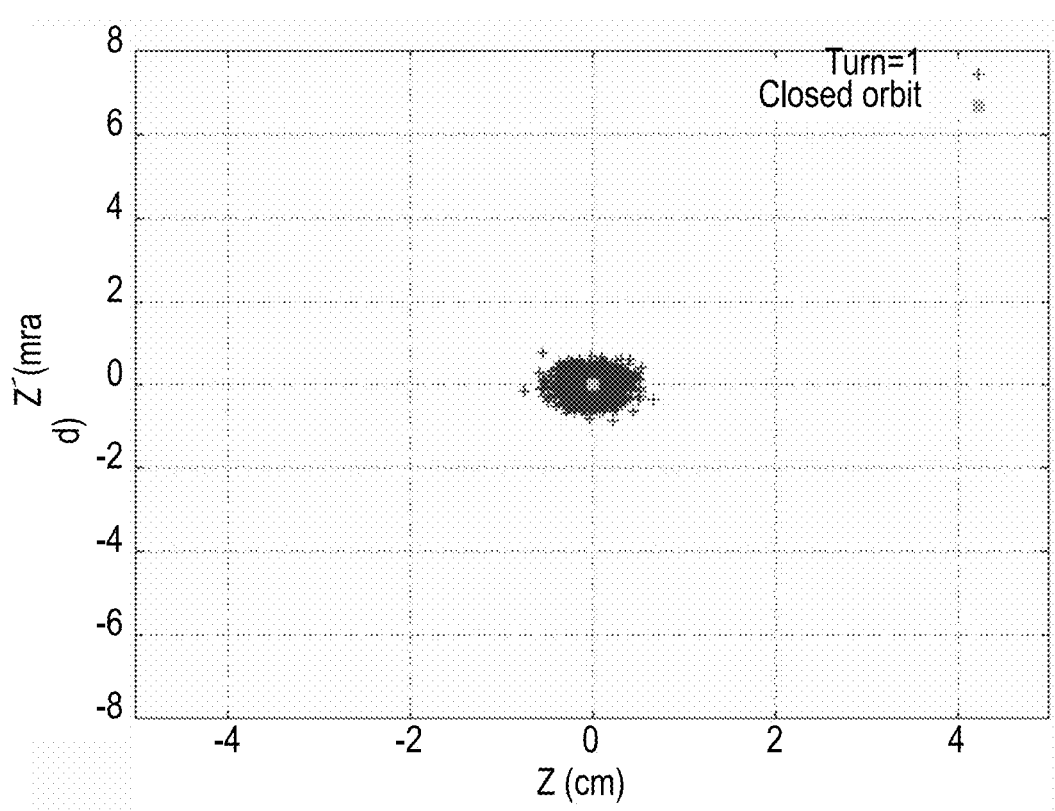

FIG. 14A and FIG. 14B are phase space diagrams that indicate the spatial displacement of particles that have a phase difference from the design orbit, in the horizontal plane and vertical plane, respectively, according to an embodiment. These depict initial spread of a beam accelerated at 50 keV. In FIG. 14A the horizontal coordinate indicates radius, in cm, in the overlapping orbits portion of the path; and the vertical axis indicates phase difference in the horizontal plane, in milliradians (mrad, 1 mrad=$10^{-3}$ radians). In FIG. 14B the horizontal coordinate indicates vertical distance over the orbital plane, in cm, in the overlapping orbits portion of the path; and the vertical axis indicates phase difference in the vertical plane, in mrad. For acceleration voltages of 500 keV and the same initial spread as depicted in FIGS. 14A and 14B, the beams evolve differently. The fraction of the beam captured in resonance islands and lost is 17% in the case where the RF voltage is 50 kV; and, much less, essentially 0%, for a fast acceleration with a RF voltage of 500 keV. Thus it is better to cross a resonance more rapidly; and, if the crossing is fast enough, very little of the beam is lost.

Figure 15:
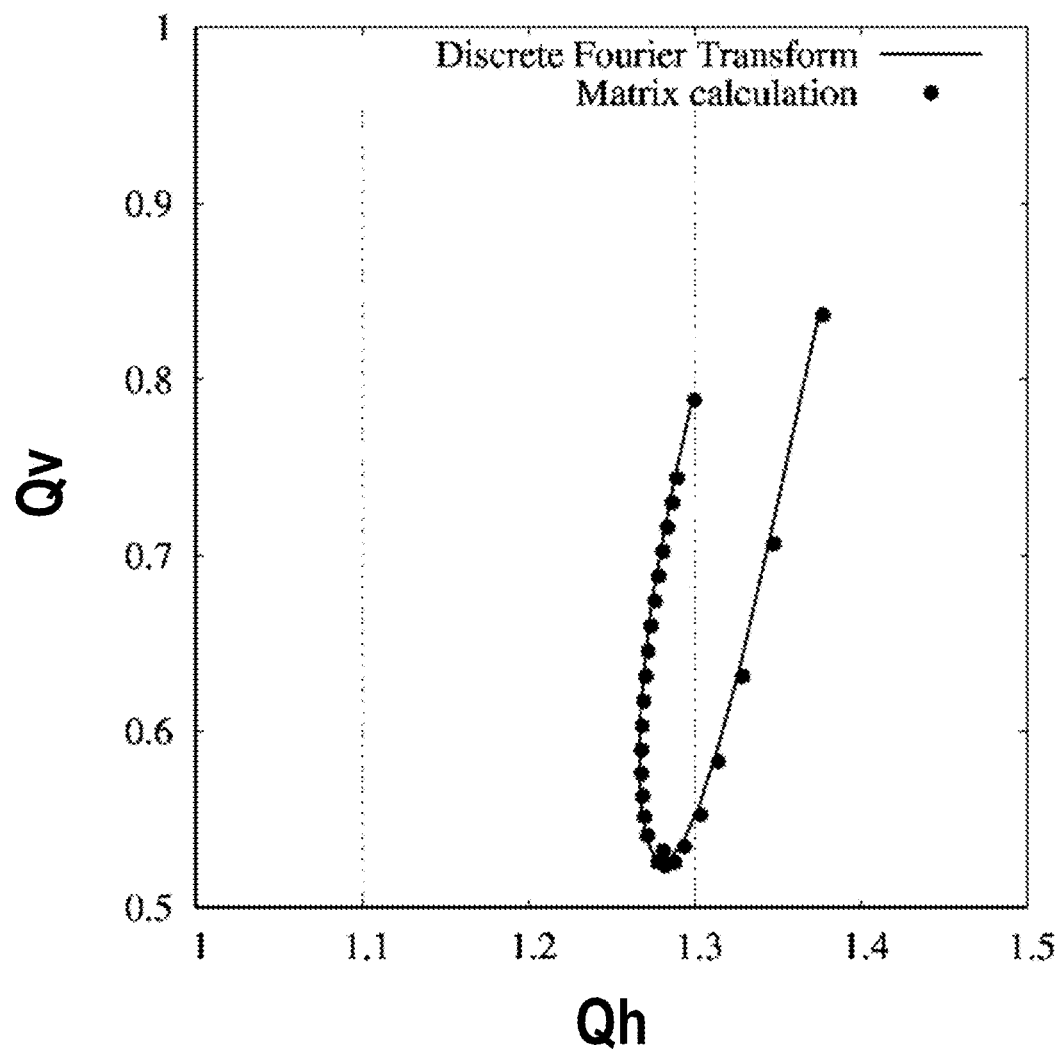
FIG. 15 is a tune diagram that illustrates a discrete Fourier transform can be used instead of the matrix computation to determine the trace of a particle with increasing kinetic energy, according to an embodiment.
Figure 16A:
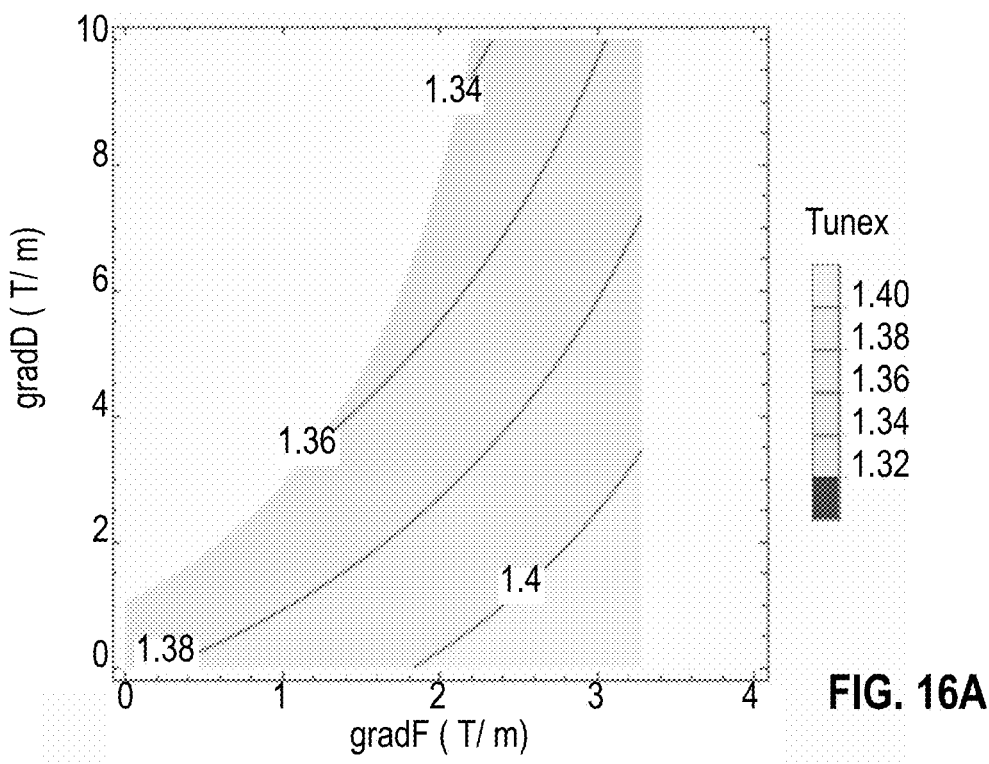
FIG. 16A through FIG. 16D are plots that illustrate example stability diagrams with at least 0.1 resolution in number of betatron oscillations (Qh and Qv) for horizontal and vertical trim quadrupole gradients at injection and extraction, according to an embodiment.
Figure 16B:
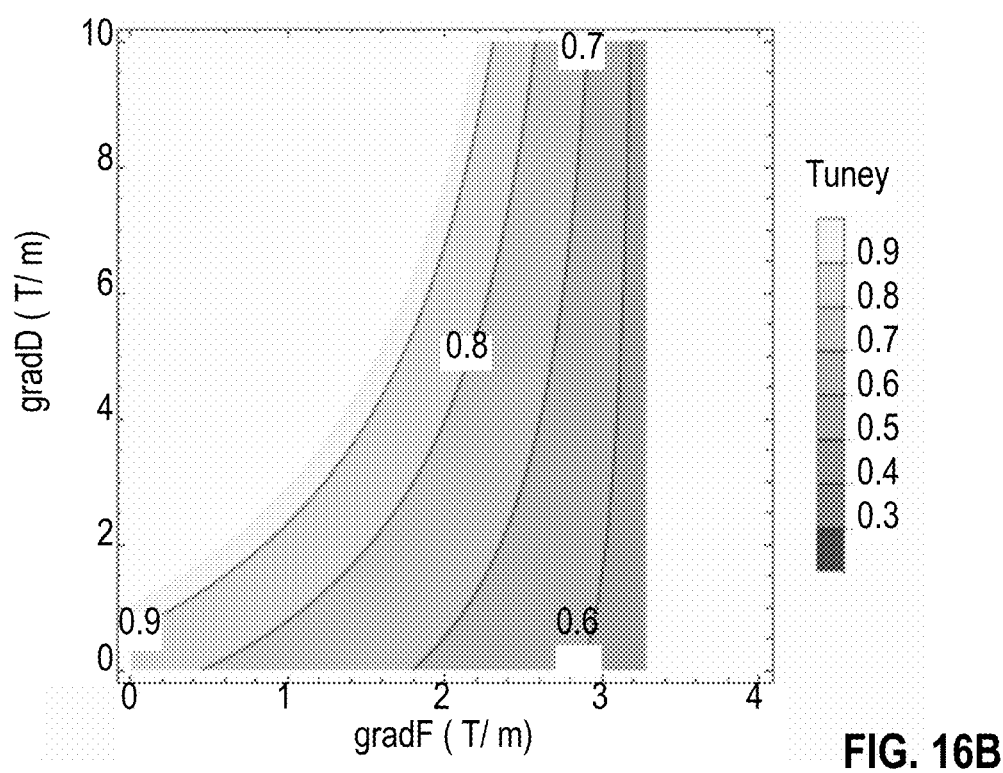
Figure 16C:
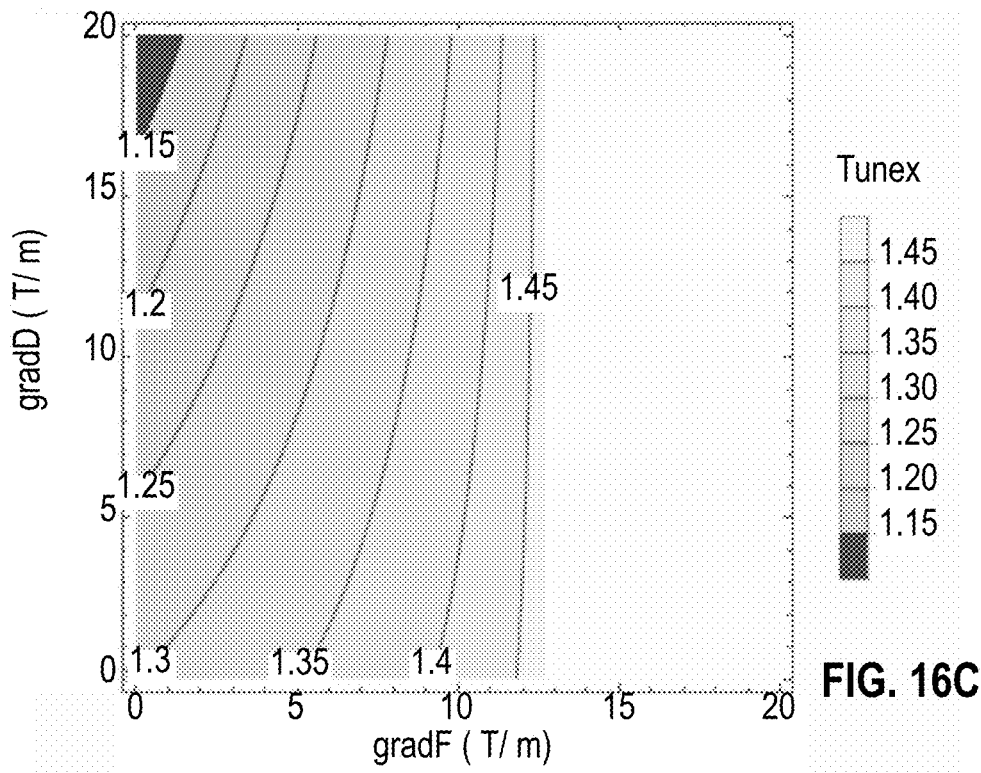
Figure 16D:
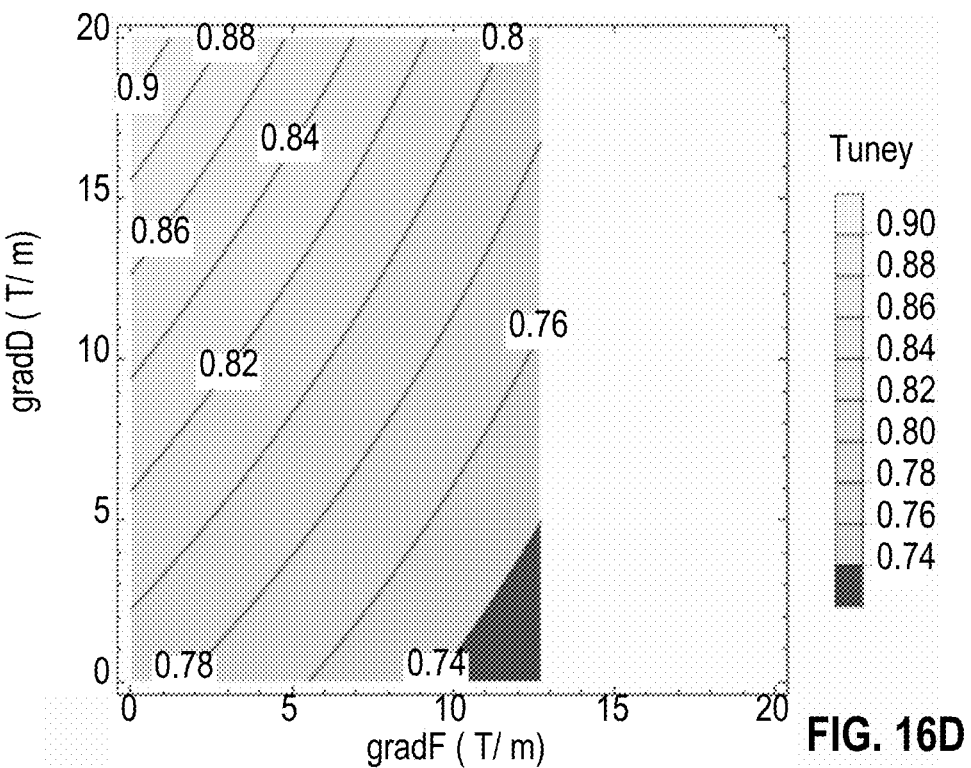

FIG. 15 is a tune diagram that illustrates a discrete Fourier transform can be used instead of the matrix computation to determine the trace of a particle with increasing kinetic energy, according to an embodiment. Both approaches produce essentially identical traces. Using the discrete Fourier transform, it is quick to model the effects of introducing and tuning trim quadrupole magnet gradients. FIG. 16A through FIG. 16D are plots that illustrate example stability diagrams with at least 0.1 resolution in Qh and Qv for horizontal and vertical trim quadrupole gradients at injection and extraction, according to an embodiment. In each plot, the horizontal axis indicates the spatial gradient in Tesla per meter (T/m) imposed by the time varying focusing trim quadrupole QF; and the vertical axis indicates the spatial gradient in T/m imposed by the time varying defocusing trim quadrupole QD (recall time varying trim quadrupoles QF and QD are combined as Trim Quad 434 in FIG. 4 and FIG. 5). The contours on the diagram indicated the resulting value for Qh (FIG. 16A and FIG. 16C for injection and ejection trim magnets, respectively), and the resulting values for Qv (FIG. 16B and FIG. 16D for injection and ejection trim magnets, respectively). By time varying the spatial gradients, a particle beam can be kept in the vicinity of an initial Qh,Qv value as the energy of the particle is increased with each orbit, thus reducing or eliminating resonance crossings.

Figure 17:
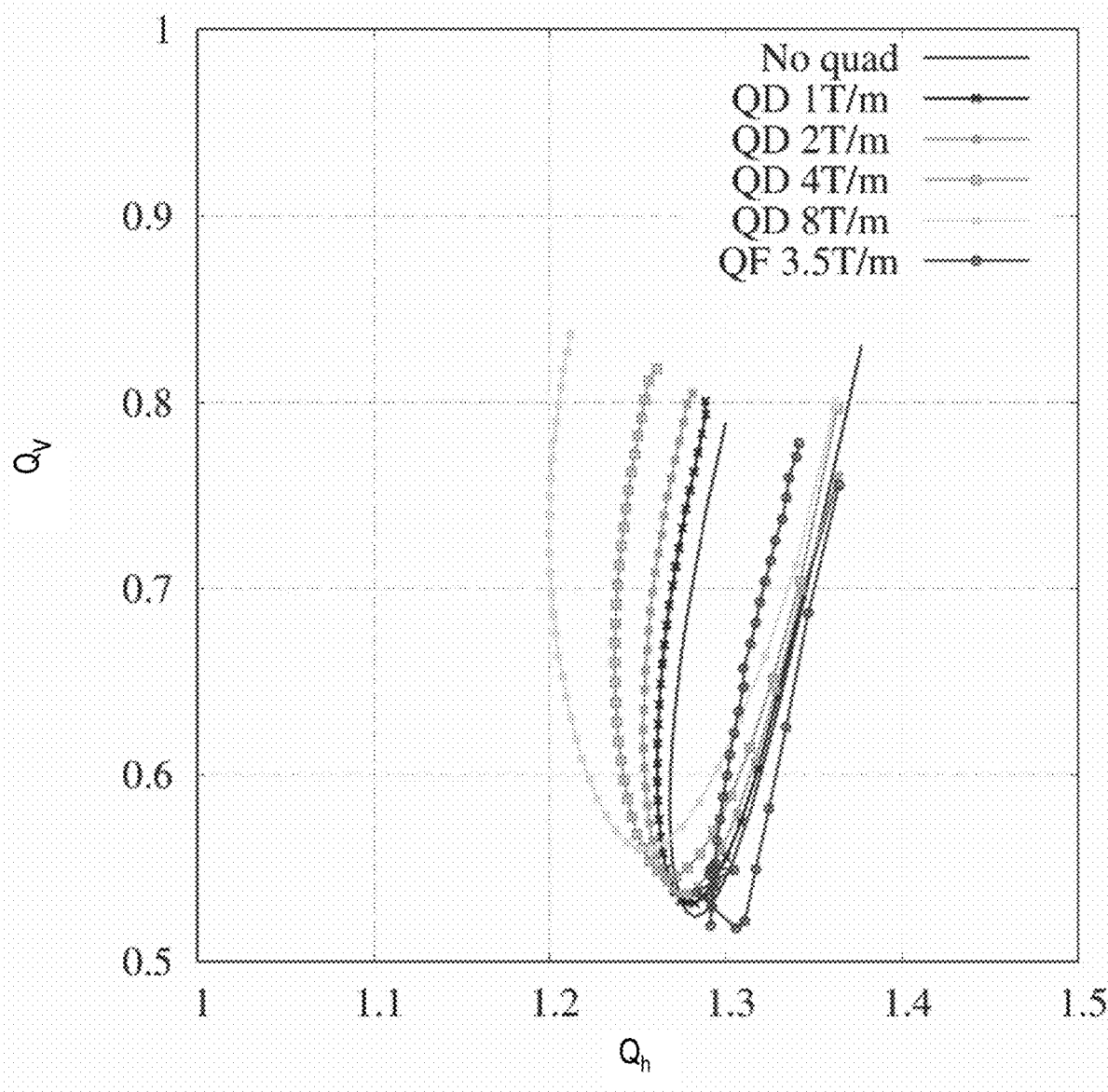
FIG. 17 is tune diagram that illustrates example changes in stability traces with changes in trim quad gradients, according to multiple embodiments.

FIG. 17 is tune diagram that illustrates example changes in stability traces with changes in trim quad gradients, according to multiple embodiments. This diagram is in one quadrant with Qh in the range 1 to 1.5 and Qv in the range 0.5 to 1.0. Trim quad gradients for QD from 0 to 8 T/m are depicted (solid line for no trim quad, X for 1 T/m, x for 2 T/m, open square for 4 T/m, closed square for 8 T/m) along with a trace (open circle) for QF gradient of 3.5 T/m. This shows that horizontal plane tune variations can be reduced using only one trim quadrupole (QF). Time variations of the field allows the modification of the starting conditions, while the RF cavity allows the modification of the crossing speed. The faster a resonance is crossed, between successive energies on successive passes, the fewer particles are captured in the resonance islands and lost from the beam.

Figure 18:
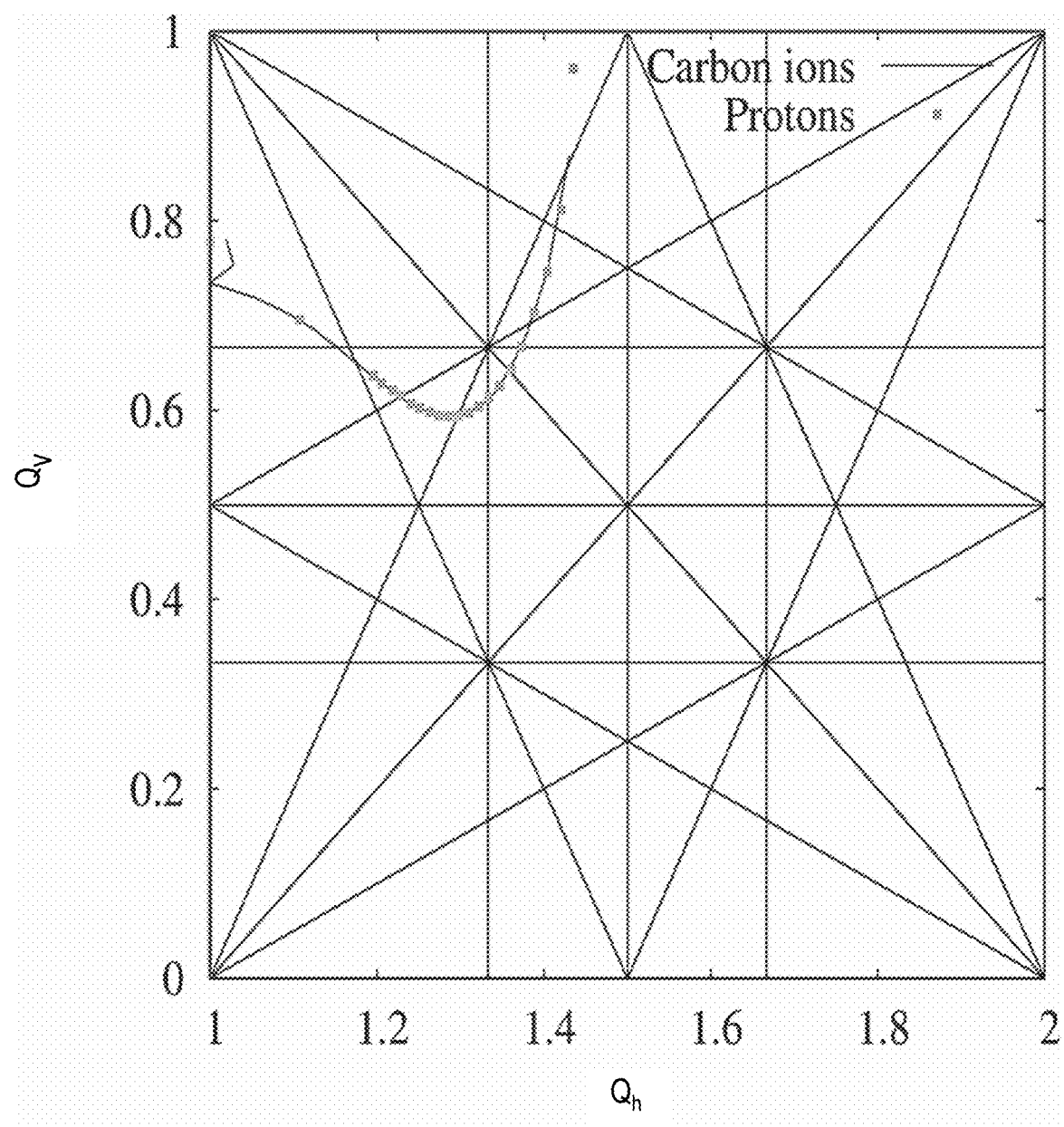
FIG. 18 is a tune diagram that illustrates similar traces for carbon ions (solid line) and protons (dots), according to an embodiment.

This Carbon ion accelerator is also suitable for protons from 22 MeV to 250 MeV. It is advantageous to inject protons at the same injection energy per nucleon as the carbon ions. This can be done in some embodiments, by using the same injector and introducing H2+ ions (two protons and one shared electron), which have the same charge to mass ratio as C6+. At the top energy, e.g., 60 MeV/nucleon, a stripper is used to remove the electron to produce two protons that can then be accelerated to a top energy of 250 MeV. FIG. 18 is a tune diagram that illustrates similar traces for carbon ions (solid line) and protons (dots), according to an embodiment.

This embodiment has very large dynamic acceptance, which means a beam with large transverse dimensions can be accommodated and accelerated without being lost. This is particularly interesting for high intensity applications. and is one of the major advantages compared to the reverse bend racetrack configuration. Taking into account the misalignment errors, the dynamic acceptance for this embodiment is about 50 mm·mrad normalized emittance that can be accepted, which is comparable to what other FFA can achieve. The highly non-linear field profile of the magnets provides the high beam current.

Figure 19A:
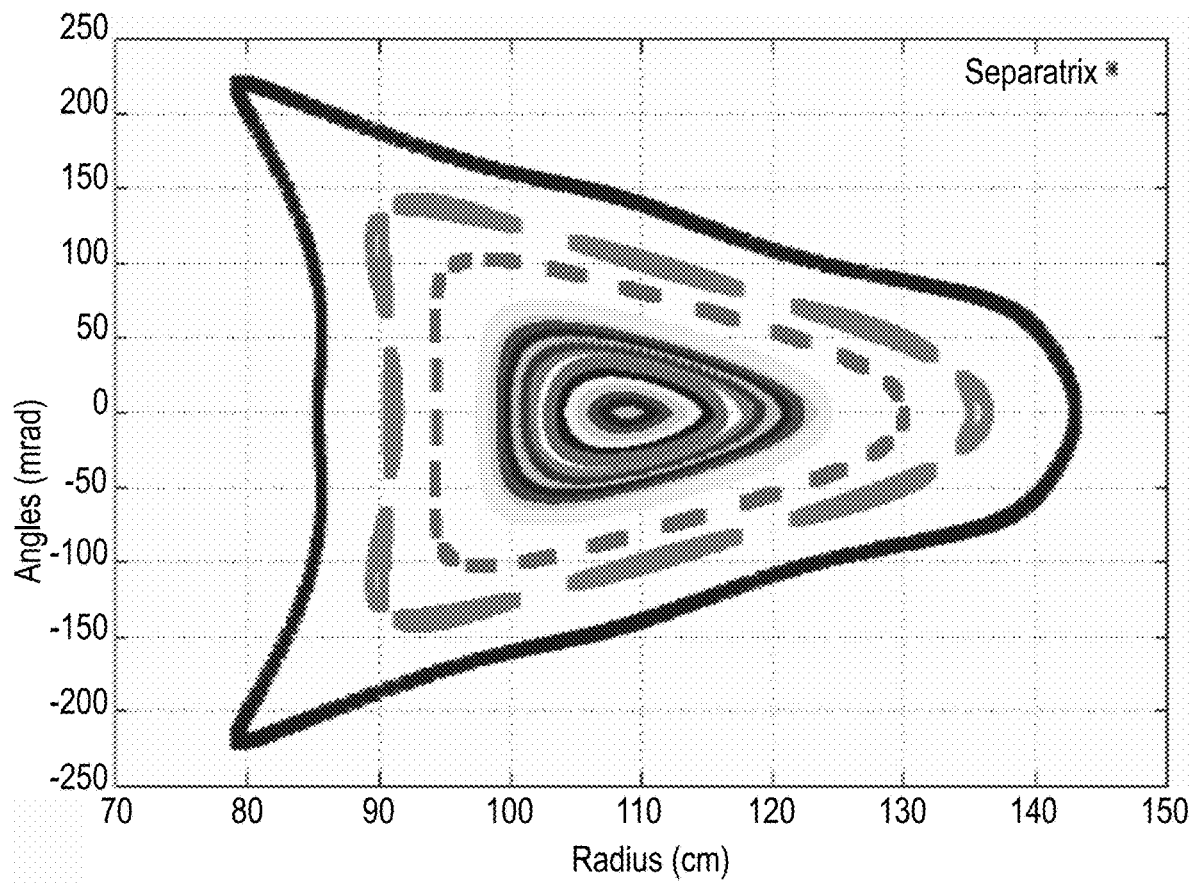
FIG. 19A and FIG. 19B are a horizontal phase diagram and a vertical phase diagram, respectively, that illustrates example particles that are stably accelerated, according to an embodiment.
Figure 19B:
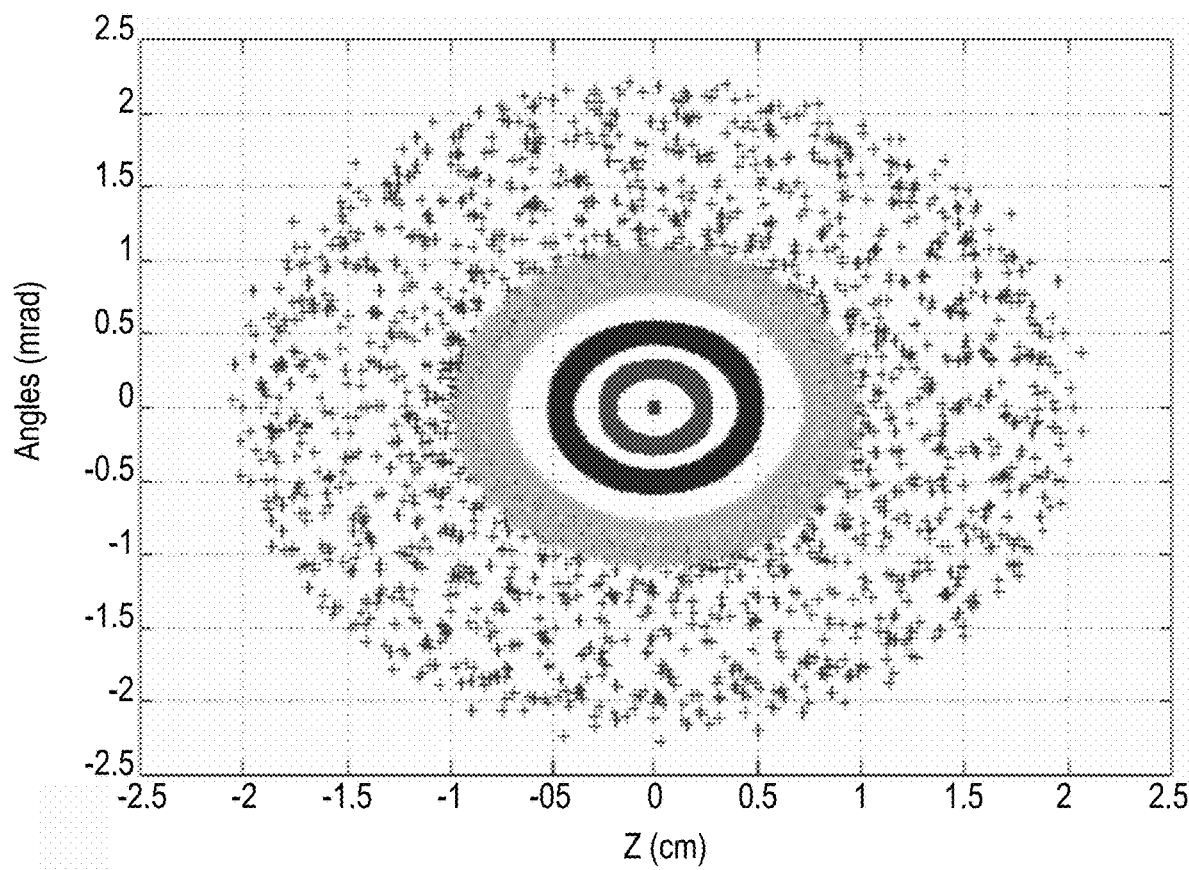

For this simulation, a particle is stable if it survives 1000 turns at injection energy with original displacement from the closed orbit. FIG. 19A is a horizontal phase diagram that illustrates example beam lengths that are stably accelerated for 1000 turns, according to an embodiment. The design orbit (e.g., the closed orbit) is at the center (angle of 0 and radius of about 110 cm). The outermost contour is the separatrix, which is the limit of the stable trajectories. FIG. 19B is a vertical phase diagram that illustrates example beam widths that are stably accelerated, according to an embodiment. Beams over +/−2 mrad from the closed orbit are stably accelerated. In this case, no resonance crossing problem occurs which explain the large beam acceptance that can be achieved.

Figure 20:
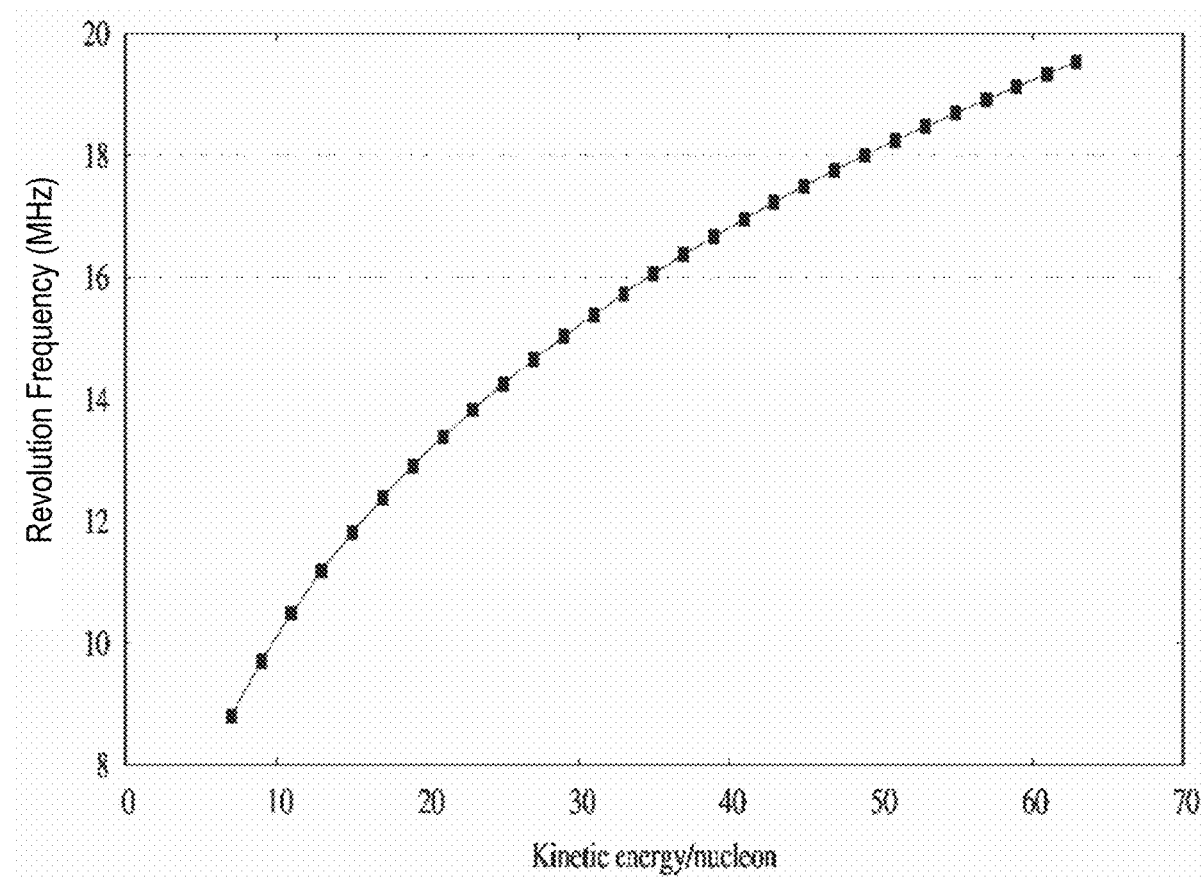
FIG. 20 is a plot that illustrates an example RF cavity frequency during acceleration of particles, according to an embodiment.

FIG. 20 is a plot that illustrates an example particle revolution frequency during acceleration of particles, according to an embodiment. The horizontal axis indicates kinetic energy in MeV per nucleon; and the vertical axis indicates particle revolution frequency f, the rate at which the RF cavity must accelerate a particle. This shows that the RF frequency needs to be adjusted in order to be synchronous with the particle motion in the longitudinal plane (the RF frequency must be an integral number of f). An RF cavity can be designed following this principle within current capabilities.

Figure 21:
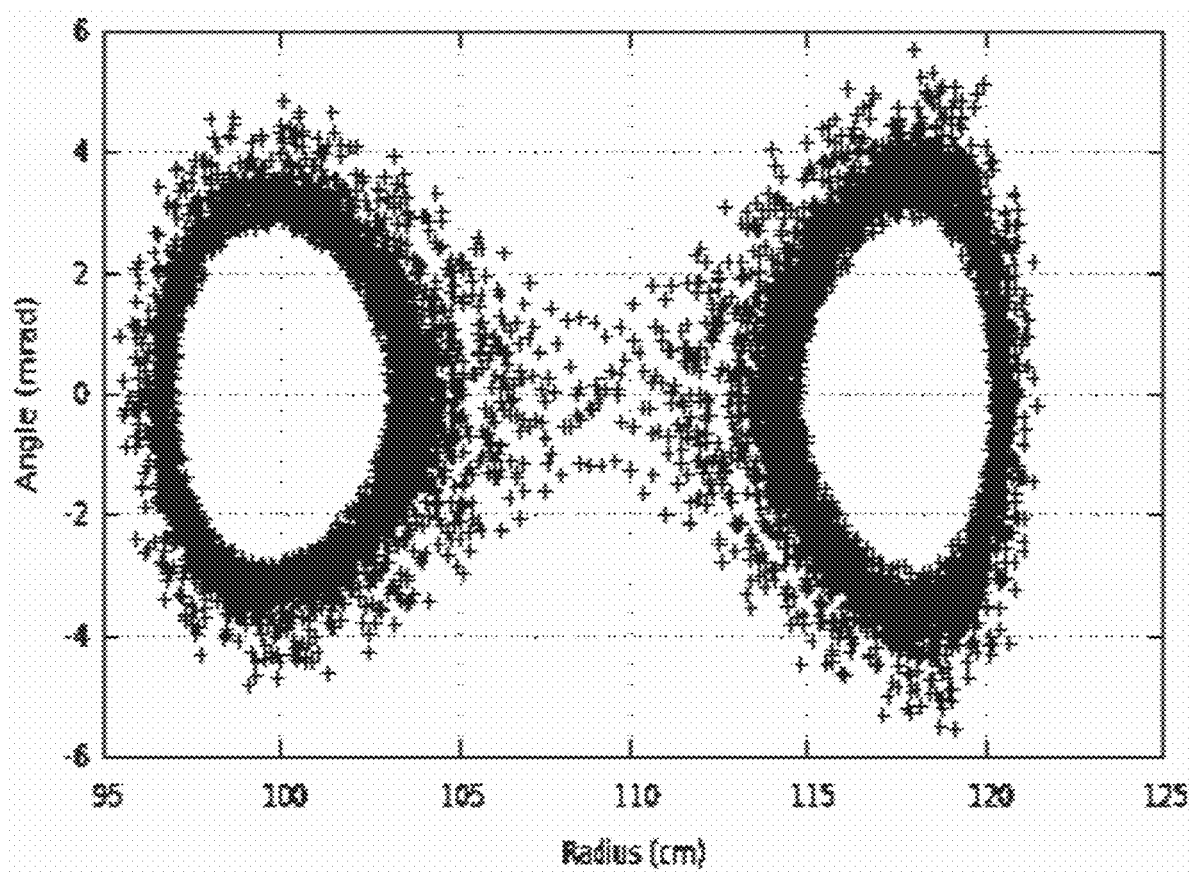
FIG. 21 is a horizontal phase diagram that illustrates divergence of particles due to crossing resonances, according to an embodiment.

FIG. 21 is a horizontal phase diagram that illustrates divergence of the particles due to crossing resonances, according to an embodiment. These particles are split into two hollow beams and are moving away from the design orbit at a radius of about 110 cm. These particles will eventually be lost; and unavailable for extraction. As stated above, stabilizing the accelerator at lower energies requires adjusting the gradient of the normal-conducting magnet to avoid crossing such resonances. The limiting factor is the vertical plane. As described above, adjusting the edge angles and width of the normal-conducting magnet will help. As shown in FIG. 10B, there is a benefit to control the tune variations mainly in the vertical plane, reducing the range of Qv from about 1.0 to less than 0.5. The horizontal plane (Qh) is acceptably stable.

Figure 22A:
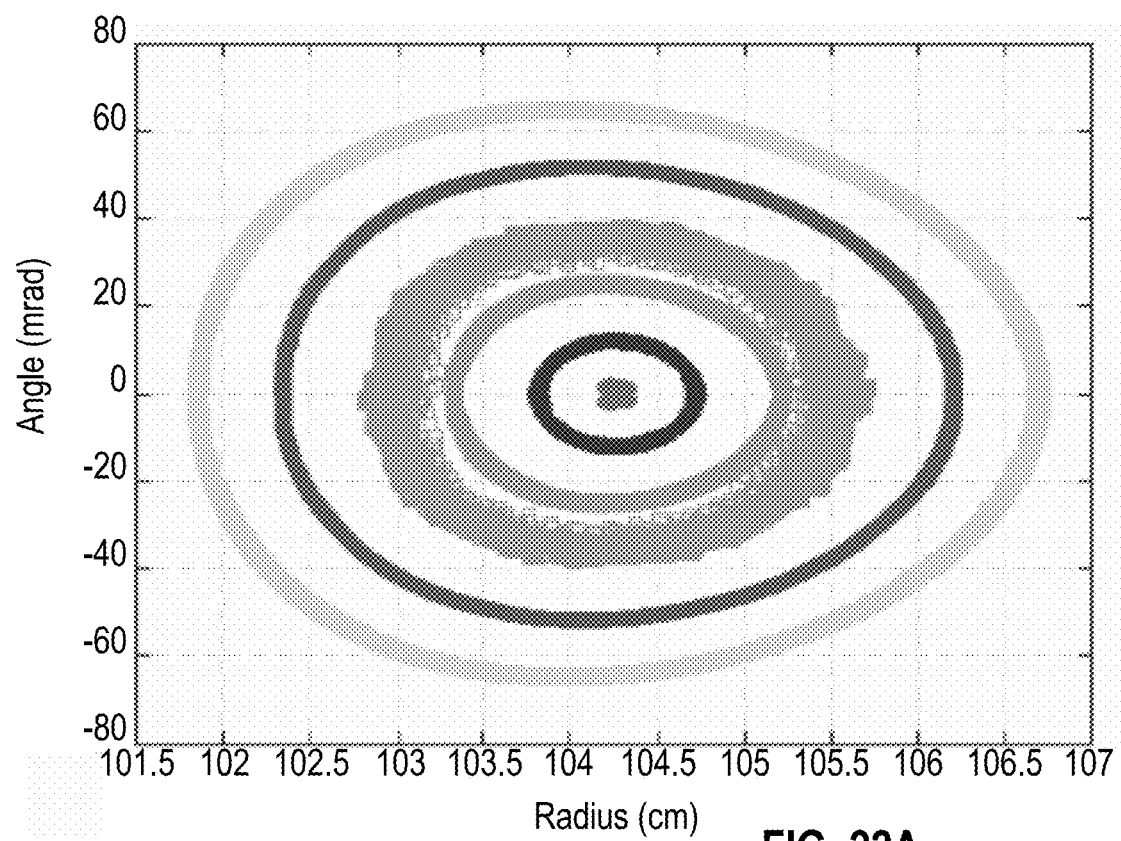
FIG. 22A and FIG. 22B are plots that illustrate an example horizontal phase space diagram and an example vertical space diagram, respectively, for a 6.5 MeV/nucleon beam, according to an embodiment.
Figure 22B:
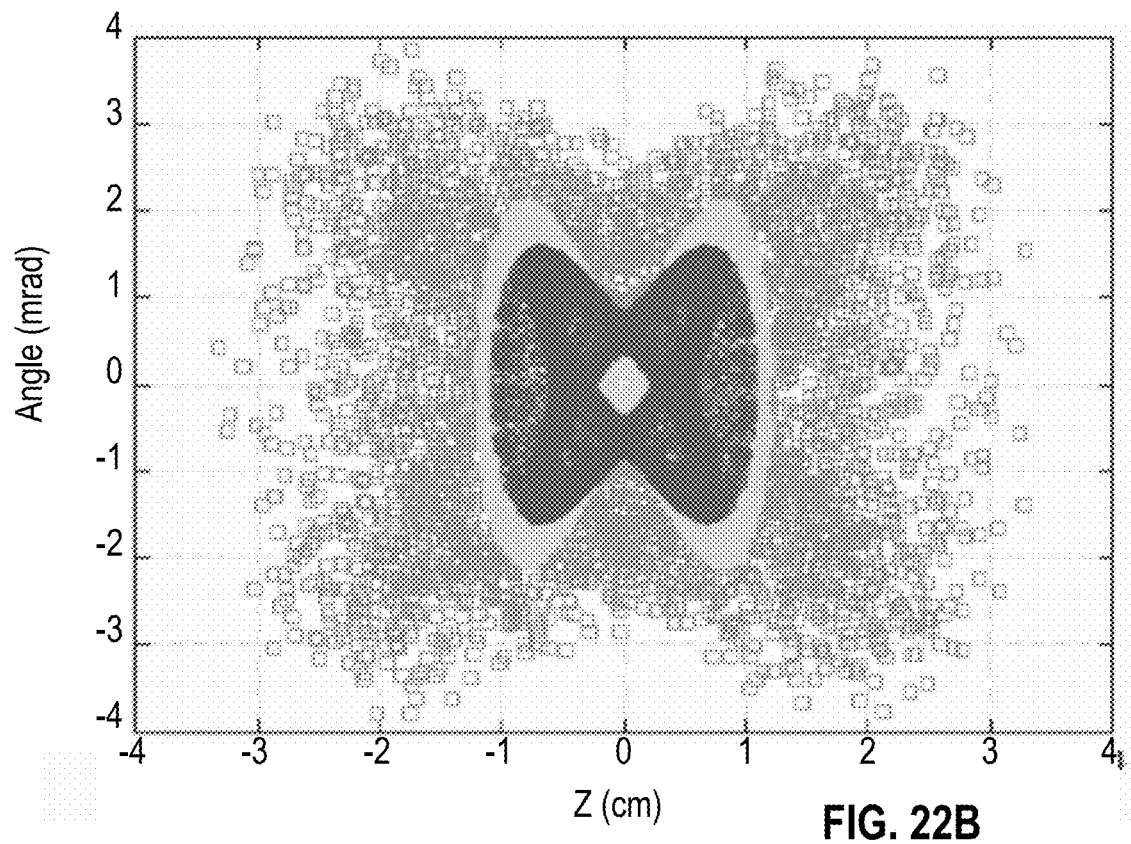
Figure 23A:
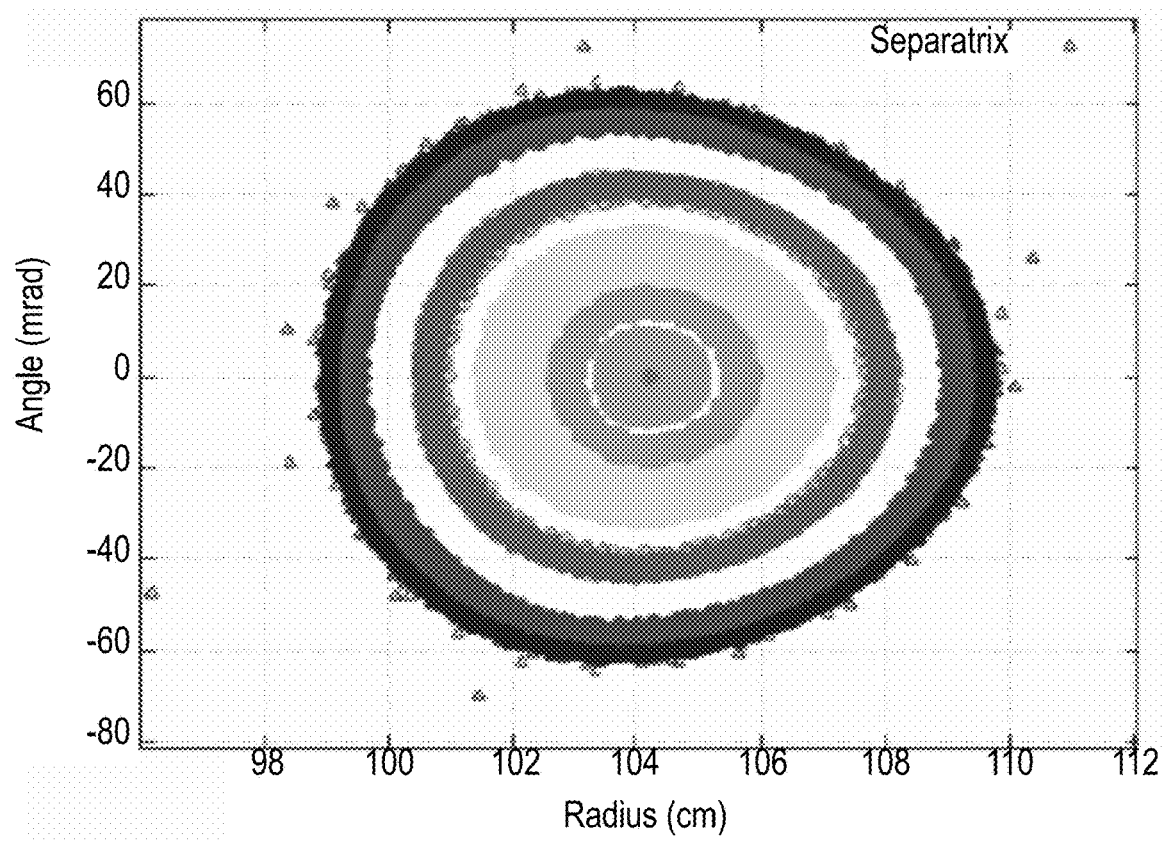
FIG. 23A and FIG. 23B are plots that illustrate an example horizontal phase space diagram and an example vertical space diagram, respectively, for a 12 MeV/nucleon beam, according to an embodiment.
Figure 23B:
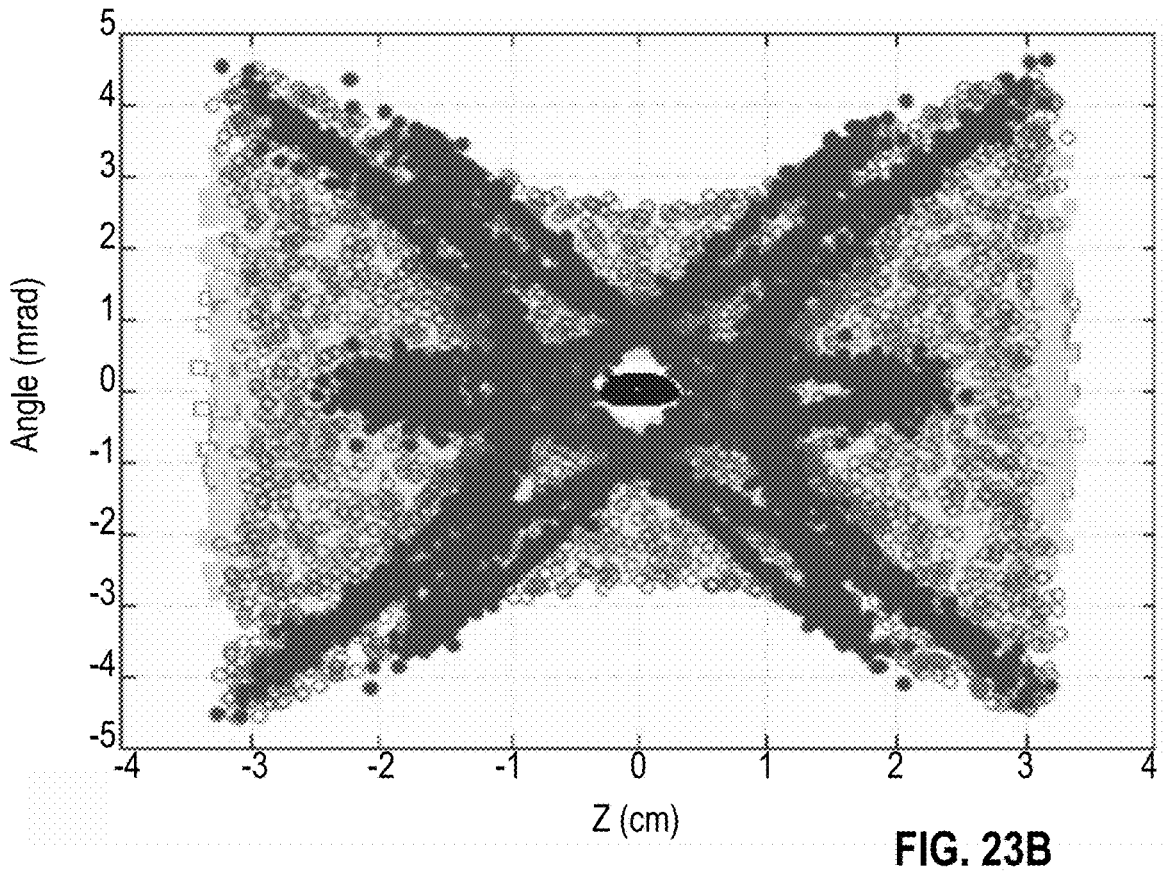
Figure 24A:
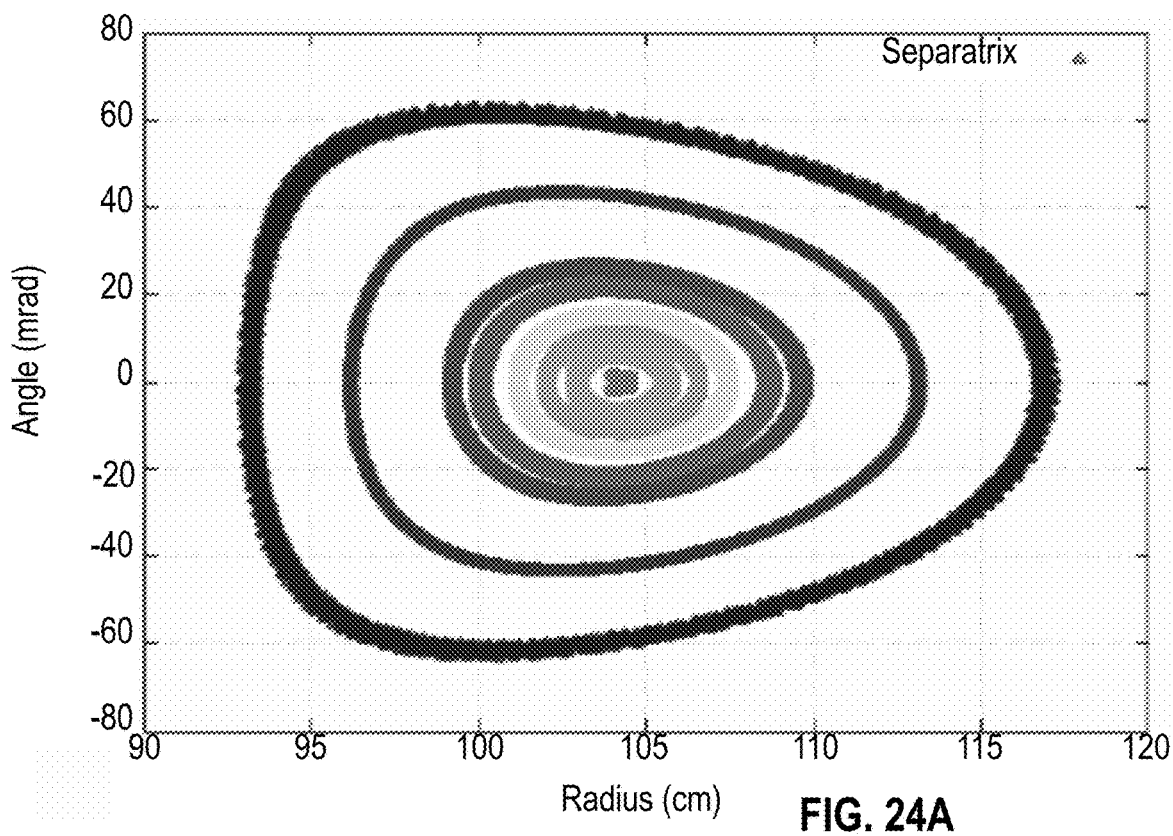
FIG. 24A and FIG. 24B are plots that illustrate an example horizontal phase space diagram and an example vertical space diagram, respectively, for a 33 MeV/nucleon beam, according to an embodiment.
Figure 24B:
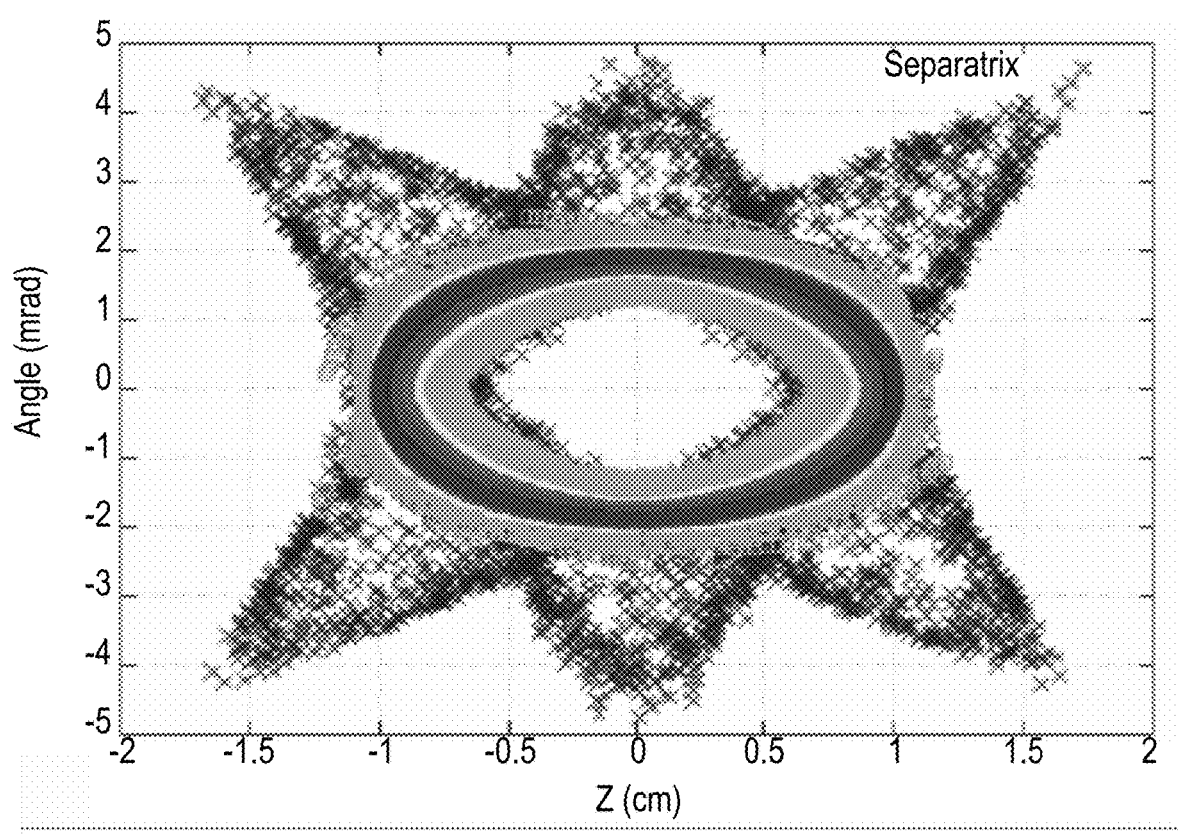
Figure 25A:
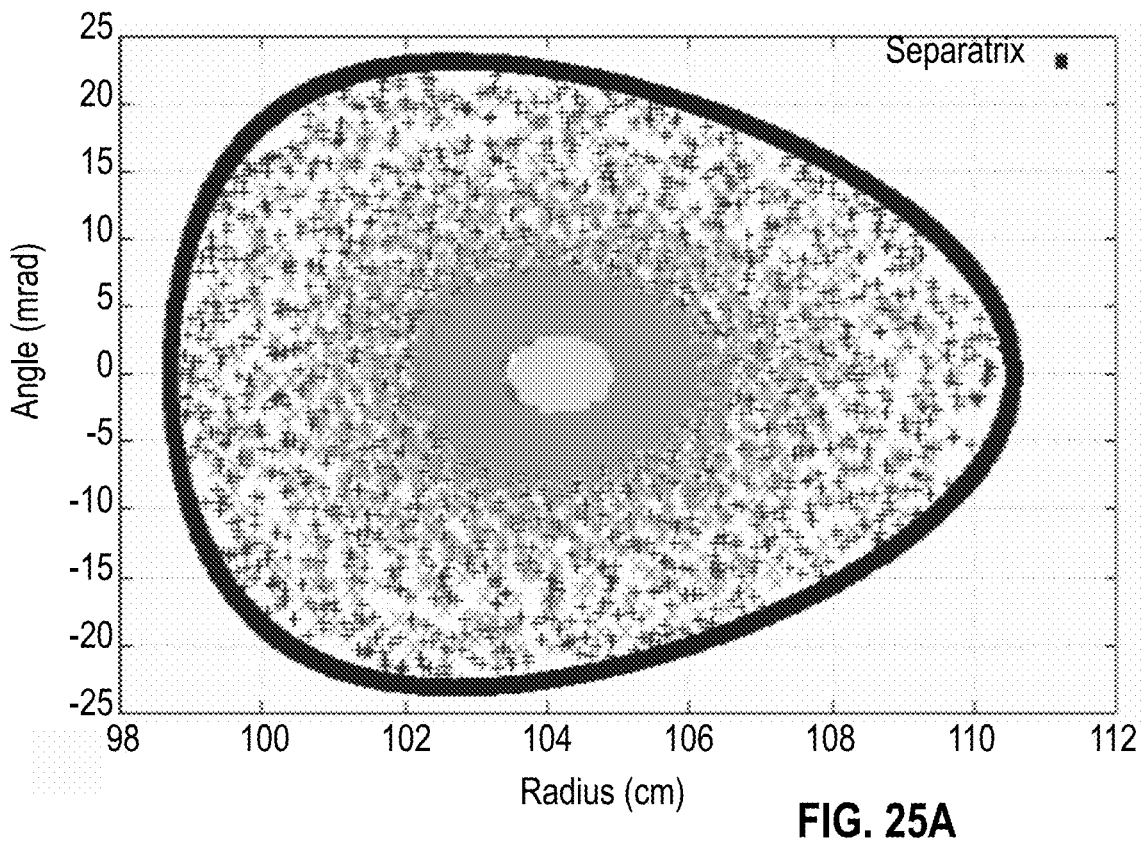
FIG. 25A and FIG. 25B are plots that illustrate an example horizontal phase space diagram and an example vertical space diagram, respectively, for a 53 MeV/nucleon beam, according to an embodiment.
Figure 25B:
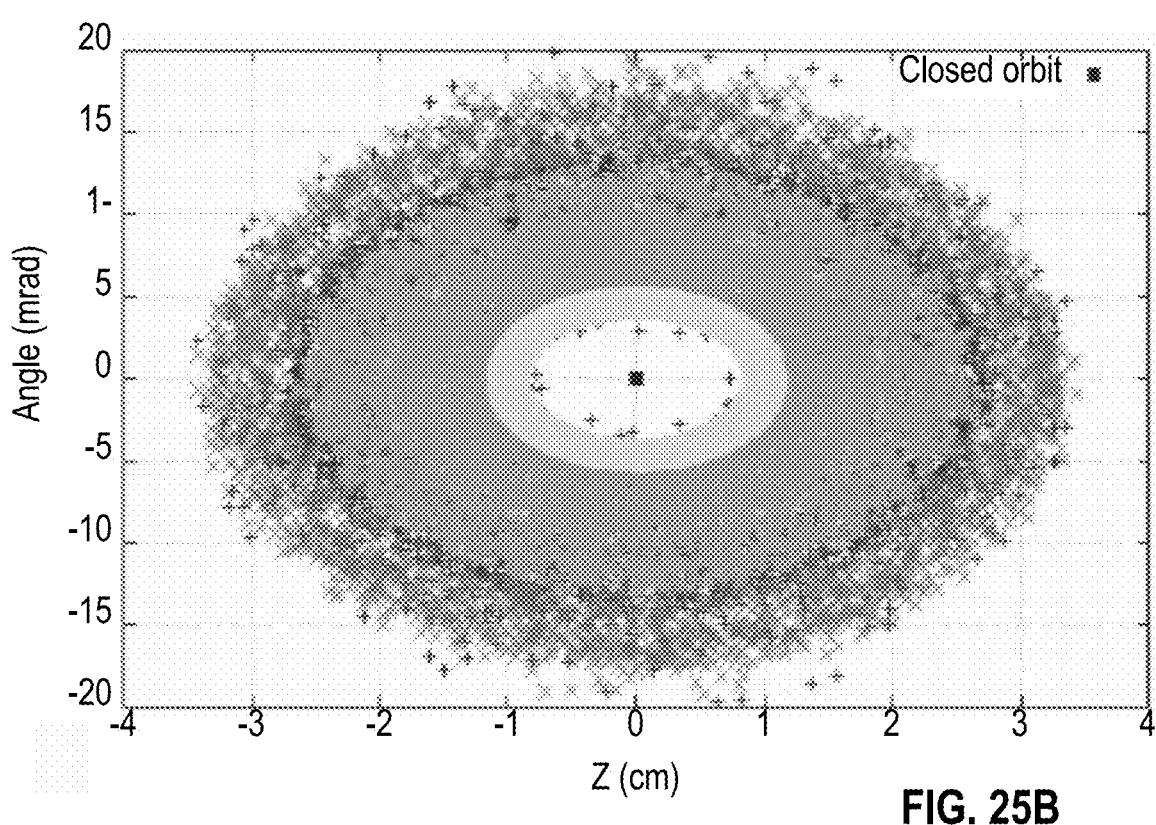

In the following embodiments, a particle is considered stable in orbit if it survives 2000 orbits for any given energy with its original displacement from the design orbit (closed orbit). A 1 cm vertical displacement was introduced for all particles to see the coupling between the horizontal and vertical plane. FIG. 22A and FIG. 22B are plots that illustrate an example horizontal phase space diagram and an example vertical space diagram, respectively, for a 6.5 MeV/nucleon beam, according to an embodiment. FIG. 23A and FIG. 23B are plots that illustrate an example horizontal phase space diagram and an example vertical space diagram, respectively, for a 12 MeV/nucleon beam, according to an embodiment FIG. 24A and FIG. 24B are plots that illustrate an example horizontal phase space diagram and an example vertical space diagram, respectively, for a 33 MeV/nucleon beam, according to an embodiment. FIG. 25A and FIG. 25B are plots that illustrate an example horizontal phase space diagram and an example vertical space diagram, respectively, for a 53 MeV/nucleon beam, according to an embodiment. Different plots show stable particles with different initial transverse coordinates.

Figure 26A:
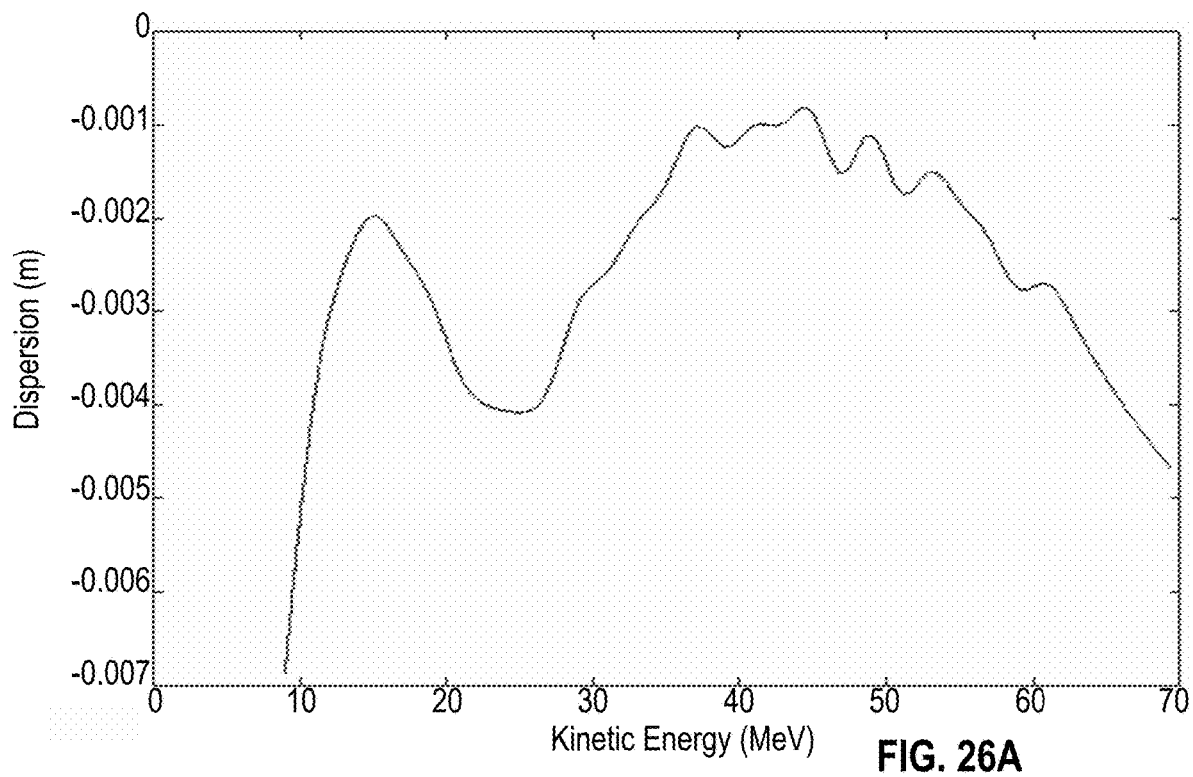
FIG. 26A and FIG. 26B are plots that illustrate an example periodic dispersion function and an example periodic betatron function, respectively, in the drift region of overlapping orbits, according to an embodiment.
Figure 26B:
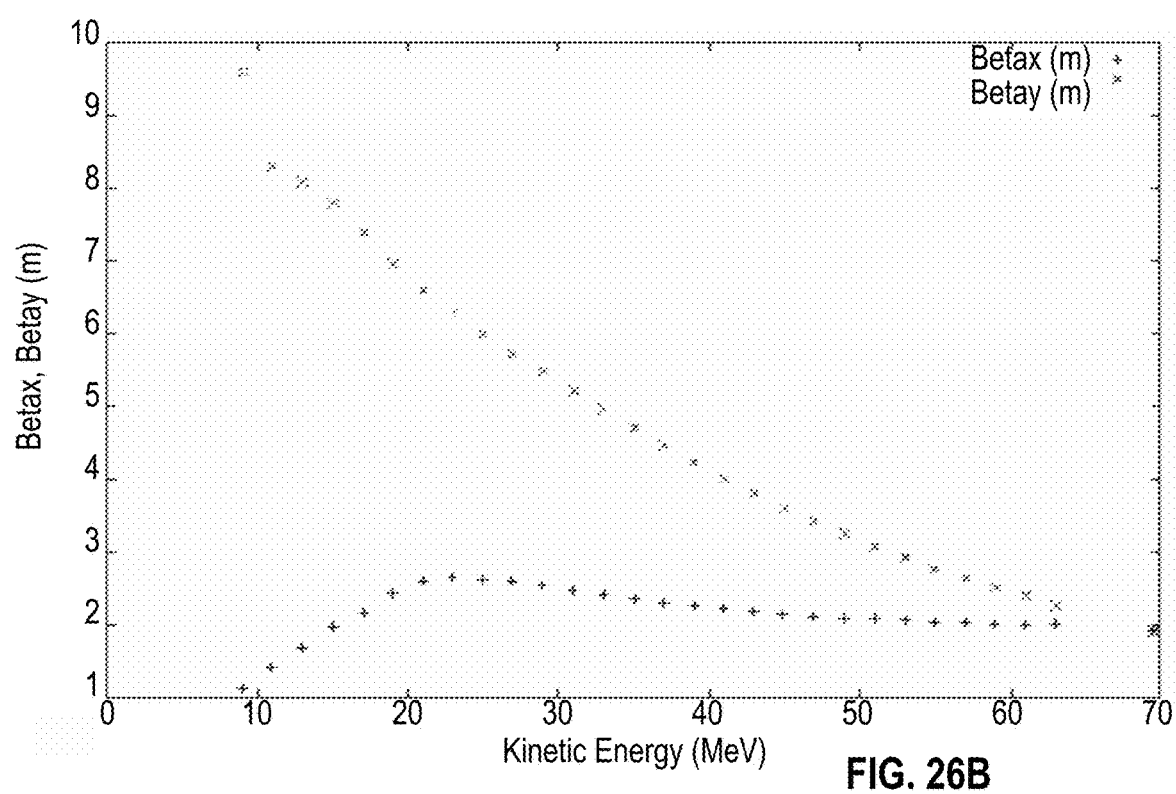

For any magnet assembly configuration embodiment, one can compute the matching conditions that allow injecting a beam of particles with the right conditions (beam size, angles) suitable for stable acceleration. The dispersion is a measure of the change of the particle position due to the momentum change. So called betatron functions, $\beta$, represent the way the beam oscillates around the closed orbit. If x denotes the transverse (radial or vertical) coordinate of the particle with respect to the closed orbit, then $x \propto \sqrt{\beta}$. In order to minimize the beam sizes, the idea is to minimize the betatron functions which also means increasing the tunes (stronger focusing). The smoother these functions are, the better it is for the extraction system, since then the beam sizes do not change much with the energy FIG. 26A and FIG. 26B are plots that illustrate an example periodic dispersion function and an example periodic betatron function, respectively, in the drift region of overlapping orbits, according to an embodiment. The horizontal axis in each is kinetic energy in MeV. It is desired that the dispersion be zero, ideally, in order to extract the beam for various energies at the same location. The dispersion functions obtained are quite small and can be further reduced to a dispersion of about 0.004 meter. This implies that a 100% change of the particle momentum induces a 4 mm change of the particle position in the drift space where the particles are to be extracted. The obtained results are excellent.

The sensitivity to injection errors is examined for several embodiments. The voltage of the RF cavity is modified in the following examples to obtain an energy gain per turn between 4 keV (very easy to achieve) to 400 keV, which is beyond current capacity. The idea is to track a particle throughout the acceleration process and record its location turn after turn in the overlapping drift space where the extraction element is placed. Ideally, the particle should come back to the original point where it will be extracted, corresponding to a radius of 103.36 cm in this embodiment.

Figure 27:
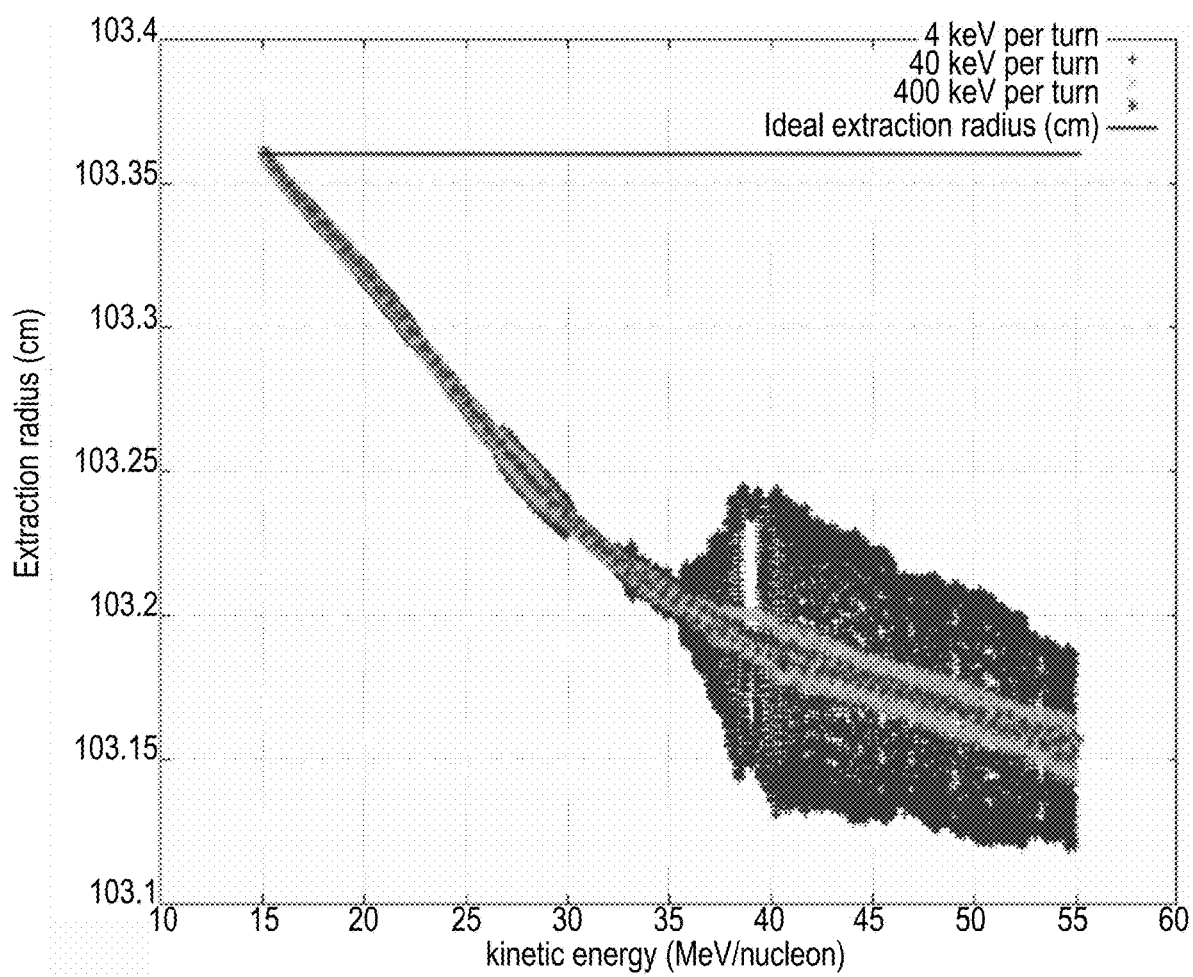
FIG. 27 is a plot that illustrates an example extraction radius as a function of particle kinetic energy in MeV/nucleon, according to an embodiment.

Instead, one does observe that the particle drifts away from the reference radius where it will be extracted (due to the dispersive effects). FIG. 27 is a plot that illustrates an example extraction radius as a function of particle kinetic energy in MeV/nucleon, according to an embodiment. However, the deviation is within 2 mm which is acceptable and does not pose a problem for extraction. Around 35 MeV, the particle starts to oscillate to larger amplitudes. This is due to resonance crossing problem and is less and less obvious when increasing the RF voltage since the time spent in the neighborhood of the resonance is significantly reduced. A few tens of keV energy gain per turn is desirable to avoid resonance crossing problems without the trim quadrupole magnets. Note that these particle oscillations reduce dramatically when using the time varying trim quadrupoles. This is because, with the trim quadrupoles, no resonance crossing occurs. In addition, by finely tuning the field of the superconducting magnets (by using trim coils implemented along the radius), this small orbit change at extraction can be further reduced.

Figure 28:
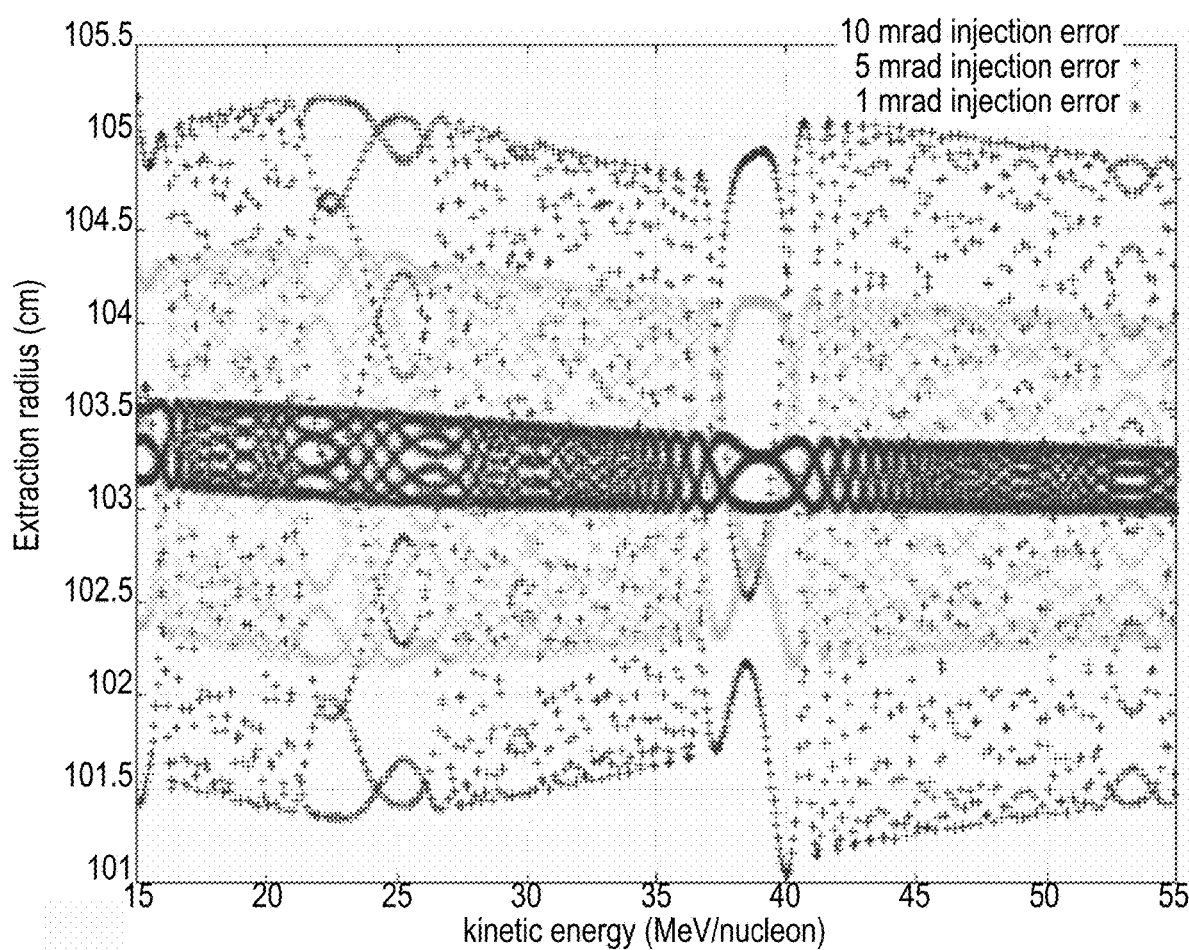
FIG. 28 is a plot that illustrates example extraction radius as a function of kinetic energy for three different injection angle errors, according to an embodiment.

The next example embodiments investigate the sensitivity to injection errors, e.g., a non-zero injection angle with respect to the closed orbit. By varying the injection angle in the horizontal plane, one can observe that the oscillation of the particle around the closed orbit increases considerably. FIG. 28 is a plot that illustrates example extraction radius as a function of kinetic energy for three different injection angle errors, according to an embodiment. The horizontal axis indicates kinetic energy in MeV/nucleon; and, the vertical axis indicate extraction radius in cm. The design orbit (closed orbit) is at 103.5 cm. Data are shown for 1 mrad error (*), 5 mrad error (X) and 10 mrad error (+). For 1 mrad injection error, the orbit radius varies by only 3 mm, which is acceptable. However, for a 10 mrad injection error, the orbit radius varies by about 4 cm. This can pose a problem for extraction at various energies. Obviously the injection errors can be mitigated and readily reduced to a few mrad. The results look promising as the matching conditions show a smooth and small dispersion functions.

The calculated transition energy for this design is 942 MeV/nucleon. This means at up to 250 MeV/nucleon for protons, the accelerator runs below transition which is very advantageous from the point of view of longitudinal beam dynamics.

3. COMPUTATIONAL HARDWARE OVERVIEW

Figure 6:
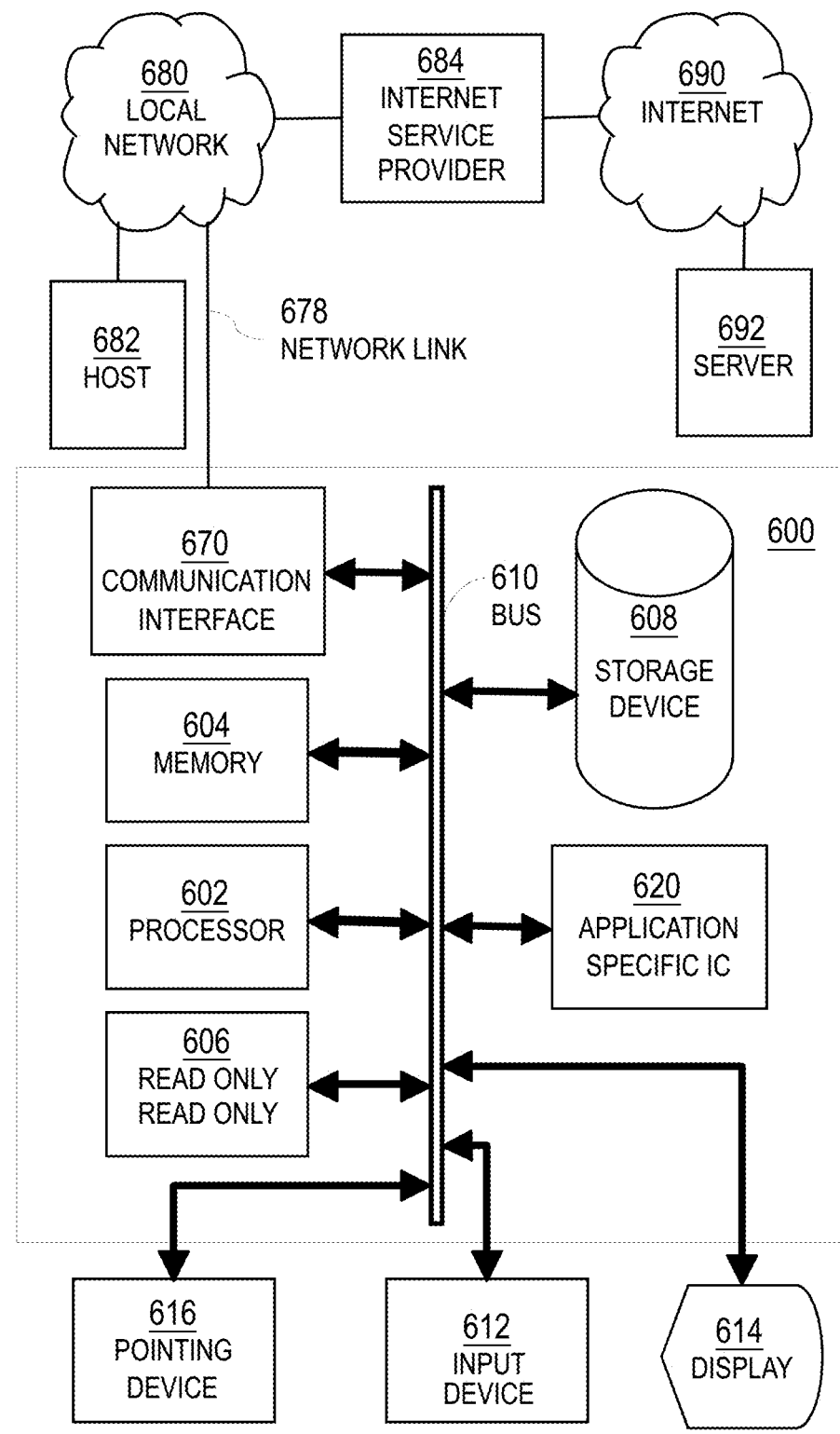
FIG. 6 is a block diagram that illustrates a computer system upon which a control system for an embodiment of the invention may be implemented.

FIG. 6 is a block diagram that illustrates a computer system 600 upon which an embodiment for operating the various components of the invention, such as the RF cavity, trim quadrupole magnets, and ejection septum, may be implemented. Computer system 600 includes a communication mechanism such as a bus 610 for passing information between other internal and external components of the computer system 600. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 600, or a portion thereof, constitutes a means for performing one or more steps of one or more methods described herein.

A sequence of binary digits constitutes digital data that is used to represent a number or code for a character. A bus 610 includes many parallel conductors of information so that information is transferred quickly among devices coupled to the bus 610. One or more processors 602 for processing information are coupled with the bus 610. A processor 602 performs a set of operations on information. The set of operations include bringing information in from the bus 610 and placing information on the bus 610. The set of operations also typically include comparing two or more units of information, shifting positions of units of information, and combining two or more units of information, such as by addition or multiplication. A sequence of operations to be executed by the processor 602 constitutes computer instructions.

Computer system 600 also includes a memory 604 coupled to bus 610. The memory 604, such as a random access memory (RAM) or other dynamic storage device, stores information including computer instructions. Dynamic memory allows information stored therein to be changed by the computer system 600. RAM allows a unit of information stored at a location called a memory address to be stored and retrieved independently of information at neighboring addresses. The memory 604 is also used by the processor 602 to store temporary values during execution of computer instructions. The computer system 600 also includes a read only memory (ROM) 606 or other static storage device coupled to the bus 610 for storing static information, including instructions, that is not changed by the computer system 600. Also coupled to bus 610 is a non-volatile (persistent) storage device 608, such as a magnetic disk or optical disk, for storing information, including instructions, that persists even when the computer system 600 is turned off or otherwise loses power.

Information, including instructions, is provided to the bus 610 for use by the processor from an external input device 612, such as a keyboard containing alphanumeric keys operated by a human user, or a sensor. A sensor detects conditions in its vicinity and transforms those detections into signals compatible with the signals used to represent information in computer system 600. Other external devices coupled to bus 610, used primarily for interacting with humans, include a display device 614, such as a cathode ray tube (CRT) or a liquid crystal display (LCD), for presenting images, and a pointing device 616, such as a mouse or a trackball or cursor direction keys, for controlling a position of a small cursor image presented on the display 614 and issuing commands associated with graphical elements presented on the display 614.

In the illustrated embodiment, special purpose hardware, such as an application specific integrated circuit (IC) 620, is coupled to bus 610. The special purpose hardware is configured to perform operations not performed by processor 602 quickly enough for special purposes. Examples of application specific ICs include graphics accelerator cards for generating images for display 614, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 600 also includes one or more instances of a communications interface 670 coupled to bus 610. Communication interface 670 provides a two-way communication coupling to a variety of external devices that operate with their own processors, such as printers, scanners and external disks. In general the coupling is with a network link 678 that is connected to a local network 680 to which a variety of external devices with their own processors are connected. For example, communication interface 670 may be a parallel port or a serial port or a universal serial bus (USB) port on a personal computer. In some embodiments, communications interface 670 is an integrated services digital network (ISDN) card or a digital subscriber line (DSL) card or a telephone modem that provides an information communication connection to a corresponding type of telephone line. In some embodiments, a communication interface 670 is a cable modem that converts signals on bus 610 into signals for a communication connection over a coaxial cable or into optical signals for a communication connection over a fiber optic cable. As another example, communications interface 670 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 670 sends and receives electrical, acoustic or electromagnetic signals, including infrared and optical signals, that carry information streams, such as digital data.

The term computer-readable medium is used herein to refer to any medium that participates in providing information to processor 602, including instructions for execution. Such a medium may take many forms, including, but not limited to, non-volatile media, volatile media and transmission media. Non-volatile media include, for example, optical or magnetic disks, such as storage device 608. Volatile media include, for example, dynamic memory 604. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 602, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 602, except for carrier waves and other signals.

Logic encoded in one or more tangible media includes one or both of processor instructions on a computer-readable storage media and special purpose hardware, such as ASIC*620.

Network link 678 typically provides information communication through one or more networks to other devices that use or process the information. For example, network link 678 may provide a connection through local network 680 to a host computer 682 or to equipment 684 operated by an Internet Service Provider (ISP). ISP equipment 684 in turn provides data communication services through the public, world-wide packet-switching communication network of networks now commonly referred to as the Internet 690. A computer called a server 692 connected to the Internet provides a service in response to information received over the Internet. For example, server 692 provides information representing video data for presentation at display 614.

The invention is related to the use of computer system 600 for implementing the techniques described herein. According to one embodiment of the invention, those techniques are performed by computer system 600 in response to processor 602 executing one or more sequences of one or more instructions contained in memory 604. Such instructions, also called software and program code, may be read into memory 604 from another computer-readable medium such as storage device 608. Execution of the sequences of instructions contained in memory 604 causes processor 602 to perform the method steps described herein. In alternative embodiments, hardware, such as application specific integrated circuit 620, may be used in place of or in combination with software to implement the invention. Thus, embodiments of the invention are not limited to any specific combination of hardware and software.

The signals transmitted over network link 678 and other networks through communications interface 670, carry information to and from computer system 600. Computer system 600 can send and receive information, including program code, through the networks 680, 690 among others, through network link 678 and communications interface 670. In an example using the Internet 690, a server 692 transmits program code for a particular application, requested by a message sent from computer 600, through Internet 690, ISP equipment 684, local network 680 and communications interface 670. The received code may be executed by processor 602 as it is received, or may be stored in storage device 608 or other non-volatile storage for later execution, or both. In this manner, computer system 600 may obtain application program code in the form of a signal on a carrier wave.

Various forms of computer readable media may be involved in carrying one or more sequence of instructions or data or both to processor 602 for execution. For example, instructions and data may initially be carried on a magnetic disk of a remote computer such as host 682. The remote computer loads the instructions and data into its dynamic memory and sends the instructions and data over a telephone line using a modem. A modem local to the computer system 600 receives the instructions and data on a telephone line and uses an infra-red transmitter to convert the instructions and data to a signal on an infra-red a carrier wave serving as the network link 678. An infrared detector serving as communications interface 670 receives the instructions and data carried in the infrared signal and places information representing the instructions and data onto bus 610. Bus 610 carries the information to memory 604 from which processor 602 retrieves and executes the instructions using some of the data sent with the instructions. The instructions and data received in memory 604 may optionally be stored on storage device 608, either before or after execution by the processor 602.

Figure 7:
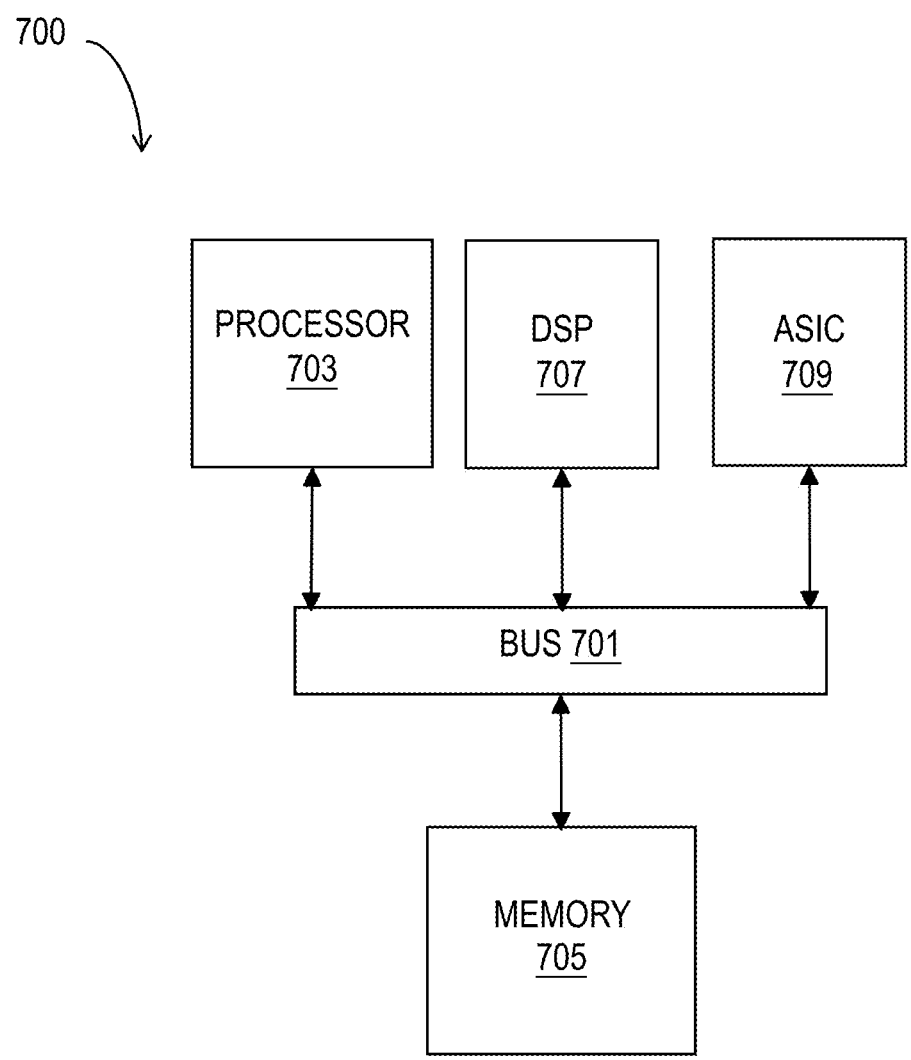
FIG. 7 is a block diagram that illustrates a chip set upon which a control system for an embodiment of the invention may be implemented.

FIG. 7 illustrates a chip set 700 upon which an embodiment of the invention may be implemented. Chip set 700 is programmed to perform one or more steps of a method described herein and includes, for instance, the processor and memory components described with respect to FIG. *6 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 700, or a portion thereof, constitutes a means for performing one or more steps of a method described herein.

In one embodiment, the chip set 700 includes a communication mechanism such as a bus 701 for passing information among the components of the chip set 700. A processor 703 has connectivity to the bus 701 to execute instructions and process information stored in, for example, a memory 705. The processor 703 may include one or more processing cores with each core configured to perform independently. A multi-core processor enables multiprocessing within a single physical package. Examples of a multi-core processor include two, four, eight, or greater numbers of processing cores. Alternatively or in addition, the processor 703 may include one or more microprocessors configured in tandem via the bus 701 to enable independent execution of instructions, pipelining, and multithreading. The processor 703 may also be accompanied with one or more specialized components to perform certain processing functions and tasks such as one or more digital signal processors (DSP) 707, or one or more application-specific integrated circuits (ASIC) 709. A DSP 707 typically is configured to process real-world signals (e.g., sound) in real time independently of the processor 703. Similarly, an ASIC 709 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 703 and accompanying components have connectivity to the memory 705 via the bus 701. The memory 705 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 705 also stores the data associated with or generated by the execution of one or more steps of the methods described herein.

4. ALTERNATIONS, DEVIATIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

5. ALTERNATIONS, DEVIATIONS AND MODIFICATIONS

[1] K. R. Symon, D. W. Kerst, L. W. Jones, L. J. Laslett and K. M. Terwilliger, \Fixed-Field Alternating-Gradient Particle Accelerators", Phys. Rev. 103, 1837 (1956).

[2] C. Villani, Landau damping. Notes for a course given in Cotonou, Benin, and in CIRM, Luminy (2010), available online

[3] A. A. Kolomensky and A. N. Lebedev, \THEORY OF CYCLIC ACCELERATORS", North-Holland publishing company, Amsterdam, pp 77-81 (1966).

[4] T. Misu, Y. Iwata, A. Sugiura, S. Hojo, N. Miyahara, M. Kanazawa, T. Murakami, and S. Yamada, \Design study of compact medical fixed-field alternating-gradient accelerators", Phys. Rev. ST Accel. Beams 7, 094701 (2004).

[5] J. M. Garland, R. B. Appleby, H. Owen, and S. Tygier, \Normal-conducting scaling fixed field alternating gradient acceler-ator for proton therapy", Phys. Rev. ST Accel. Beams 18, 094701 (2015).

[6] S. Tygier, K. B. Marinov, R. B. Appleby, J. A. Clarke, J. M. Garland, H. L. Owen, and B. J. A. Shepherd, \Medical therapy and imaging fixed-field alternating-gradient accelerator with realistic magnets", Phys. Rev. Accel. Beams 20, 104702 (2017).

[7] S. Machida, \Scaling Fixed-Field Alternating-Gradient Accelerators with Reverse Bend and Spiral Edge Angle", Phys. Rev. Lett. 119, 064802 (2017).

[8] J. S. Berg, S. A. Bogacz, S. Caspi, J. Cobb, R. C. Fernow, J. C. Gallardo, S. Kahn, H. Kirk, D. Neuffer, R. Palmer, K. Paul, H. Witte, and M. Zisman, \Cost-effective design for a neutrino factory", Phys. Rev. ST Accel. Beams 9, 011001 (2006).

[9] M. Haj Tahar and F. Meot, \Tune compensation in non-linear Fixed Field Alternating Gradient accelerators", https://arxiv.org/pdf/1710.08772.pdf

[10] J. M. Schippers, \Beam Transport Systems for Particle Therapy", CERN Yellow Reports: School Proceedings, 1, 241. doi:http://dx.doi.org/10.23730/CYRSP-2017-001.241 (2017)

[11] F. Meot, \Zgoubi Users Guide", Report CA/AP/470, BNL C-AD (2012)

[12] H. A. Enge, Focusing of Charged Particles, edited by A. Spetier (Academic Press, New York, 1967), Vol. 2, p. 203.

[13] S. Machida, Y. Mori, A. Muto, J. Nakano, C. Ohmori, I. Sakai, Y. Sato, A. Takagi, T. Yokoi, M. Yoshii, M. Yoshimoto, Y. Yuasa, M. Matoba, Y. Yonemura, A. Yamazaki, T. Uesugi, M. Aiba, M. Sugaya, Proc. of EPAC2004, Lucerne, p. 2643, 2004.

[14] C. H. Pyeon, et al., \First Injection of Spallation Neutrons Generated by High-Energy Protons into the Kyoto University Critical Assembly", J. Nucl. Scie. Technol. Vol. 46 (2009), No. 12 pp. 1091-1093

[15] Y. Ishi, \Status of KURRI Facility", presented at the FFAG 2016 workshop, Imperial college, London, UK (September 2016).

[16] S. L. Sheehy, D. J. Kelliher, S. Machida, C. Rogers, C. R. Prior, L. Volat, M. Haj Tahar, Y. Ishi, Y. Kuriyama, M. 9 Sakamoto, T. Uesugi and Y. Mori, \Characterization techniques for fixed field alternating gradient accelerators and beam studies using the 150 MeV proton FFAG", Progress of Theoretical and Experimental Physics (July 2016).

[17] S. L. Sheehy et al., \CHARACTERISATION OF THE KURRI 150 MeV FFAG AND PLANS FOR HIGH INTENSITY EXPERIMENTS", presented at the 57th ICFA Advanced Beam Dynamics Workshop on High Intensity, High Brightness and High Power Hadron Beams (HB2014), Michigan, USA, November 2014, paper MOPAB27, pp 89{93.

[18] N. N. Bogoliubov and Y. A. Mitropolskii, \Asymptotic methods in the theory of nonlinear oscillations", Gordon and Breach, New York (1961).

[19] S. Machida, \Scaling Fixed-Field Alternating Gradient Accelerators with a Small Orbit Excursion", Phys. Rev. Lett. 103, 164801 (2009).

[20] S. L. Sheehy et al, \Progress on simulation of fixed field alternating gradient accelerators", MOPJE077, IPAC'15, Virginia, USA (2015).

[21] One will show later that the focusing can be further increased by placing alternating gradient elements in the drift space which are essentially focusing and defocusing quadrupoles.

[22] At this point, one has to start from the simplest solution that is guaranteed to yield a stable lattice. However, after several iterations, the final solution will not resemble the initial one.

[23] The merit of the field maps is that, once the magnets are built, the simulated field maps can be replaced with the measured ones to yield a realistic representation of the accelerator model.

What is claimed is:

1. A system comprising:
    a charged particle linear accelerator module configured to accelerate a pulse of charged particles as a beam aligned along a first ray; and
    a pair of fixed field magnet assemblies configured to turn a moving charged particle 360 degrees within a first plane, wherein the fixed field magnet assemblies are disposed on opposite sides of the linear accelerator along the first ray and the pair of fixed field magnet assemblies is arranged with mirrored symmetry relative to a line perpendicular to the first ray and through a reference point in the first plane not on the first ray, each assembly comprising:
        a pair of magnets for which a strength on the first plane of a magnetic field perpendicular to the first plane varies non-linearly along a radial direction from the reference point; wherein the pair of magnets are disposed in the first plane with mirror symmetry about a line parallel to the first ray and through the reference point, and
        a superconducting magnet for which a strength on the first plane of a field perpendicular to the first plane varies along a radial direction from the reference point, the superconducting magnet disposed between the pair of magnets on the first plane.

2. A system as recited in claim 1, wherein a fixed magnetic field of each assembly is configured so that a beam of charged particles having particle energies within first range of energies that enters a first assembly of the pair of fixed field magnet assemblies along the first ray exits the first assembly along a different second ray opposite in direction to the first ray and displaced in a direction perpendicular to the second ray, enters a different second assembly of the pair of fixed field magnet assemblies along the second ray, and exits the second assembly along the first ray.

3. A system as recited in claim 2, wherein the second ray is coincident for all beams of the same charged particle type within the first range of energies.

4. A system as recited in claim 2, wherein the beam of charged particles is a beam of protons and the first range of energies for each proton is from about 22 million electron volts (MeV) to about 250 MeV.

5. A system as recited in claim 2 or claim 4, wherein the beam of charged particles is a beam of Carbon ions and the first range of energies for each Carbon ion is from about 5 million electron volts (MeV) to about 64 MeV.

6. A system as recited in claim 1, wherein:
in at least one fixed field magnet assembly, the superconducting magnet comprises a pair of superconducting magnets;
a first superconducting magnet of the pair of superconducting magnets and a first magnet of the pair of magnets for which strength varies non-linearly comprises a first subassembly second superconducting magnet of the pair of superconducting magnets and a second magnet of the pair of magnets for which strength varies non-linearly comprises a second subassembly configured to turn the beam of particles 90 degrees; and
the first sub-assembly and the second sub-assembly are arranged with mirrored symmetry to each other relative to a line parallel to the first ray and through the reference point.

7. A system as recited in claim 1, wherein a circumference of the system in the horizontal plane is less than about 15 meters.

8. A system as recited in claim 1, further comprising an injection septum disposed along the first ray and an extraction septum disposed along the second ray.

9. A system as recited in claim 1, further comprising a quadrupole magnet disposed along the first ray or the second ray to reduce resonant displacements from the first ray or the second ray.

10. A system as recited in claim 1, further comprising an electron stripping device disposed along the first ray or the second ray to increase charge of the charged particle whereby a maximum energy of the first range of energies increases.

11. A system as recited in claim 1, further comprising a stripping device disposed along the first ray or the second ray to dissociate particles in a molecular hydrogen beam into protons.

* * * * *